United States Patent
Kerem et al.

(10) Patent No.: US 12,351,803 B2
(45) Date of Patent: *Jul. 8, 2025

(54) RESTORATION OF THE CFTR FUNCTION BY SPLICING MODULATION

(71) Applicants: YISSUM RESEARCH DEVELOPMENT COMPANY OF THE HEBREW UNIVERSITY OF JERUSALEM LTD., Jerusalem (IL); SpliSense Ltd., Jerusalem (IL)

(72) Inventors: Bat Sheva Kerem, Mevaseret Zion (IL); Efrat Ozeri-Galai, Jerusalem (IL); Yifat Oren, Jerusalem (IL); Ofra Barchad-Avitzur, Jerusalem (IL)

(73) Assignees: YISSUM RESEARCH DEVELOPMENT COMPANY OF THE HEBREW UNIVERSITY OF JERUSALEM LTD., Jerusalem (IL); SpliSense Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/765,286

(22) Filed: Jul. 7, 2024

(65) Prior Publication Data

US 2024/0352461 A1 Oct. 24, 2024

Related U.S. Application Data

(63) Continuation of application No. 17/607,908, filed as application No. PCT/IL2020/050495 on May 5, 2020.

(60) Provisional application No. 62/843,469, filed on May 5, 2019.

(51) Int. Cl.
*C12N 15/113* (2010.01)
*A61K 31/7088* (2006.01)
*A61K 45/06* (2006.01)
*A61P 11/00* (2006.01)

(52) U.S. Cl.
CPC ........ *C12N 15/113* (2013.01); *A61K 31/7088* (2013.01); *A61K 45/06* (2013.01); *A61P 11/00* (2018.01); *C12N 2310/11* (2013.01); *C12N 2320/31* (2013.01)

(58) Field of Classification Search
CPC .............. C12N 15/113; C12N 2310/11; C12N 2320/31; A61K 31/7088; A61K 45/06; A61P 11/00
See application file for complete search history.

(56) References Cited

U.S. PATENT DOCUMENTS

| | | | |
|---|---|---|---|
| 6,730,777 B1 * | 5/2004 | Tsui | C07K 16/18 530/350 |
| 6,902,907 B1 * | 6/2005 | Tsui | C12N 15/8509 435/325 |
| 6,984,487 B1 * | 1/2006 | Tsui | B82Y 5/00 536/23.1 |
| 9,840,709 B2 | 12/2017 | Hastings | |
| 9,976,143 B2 | 5/2018 | Krainer | |
| 10,179,106 B2 * | 1/2019 | Yedgar | A61K 9/1271 |
| 10,233,499 B2 | 3/2019 | Rohlfs | |
| 10,428,328 B2 * | 10/2019 | Kerem | A61K 45/06 |
| 10,525,076 B2 | 1/2020 | Hastings | |
| 10,544,417 B2 | 1/2020 | Hastings | |
| 10,624,851 B2 * | 4/2020 | Yedgar | A61K 9/127 |
| 10,647,983 B2 | 5/2020 | Krainer | |
| 10,696,969 B2 | 6/2020 | Krainer | |
| 10,731,156 B2 * | 8/2020 | Kerem | C12N 15/1138 |
| 11,096,956 B2 | 8/2021 | Aznarez | |
| 11,116,785 B2 | 9/2021 | Hastings | |
| 11,352,624 B2 | 6/2022 | Krainer | |
| 2013/0122493 A1 * | 5/2013 | Xu | C12Q 1/6827 435/6.12 |
| 2014/0011977 A1 | 1/2014 | Krainer | |
| 2015/0211010 A1 * | 7/2015 | Kerem | C12N 15/1138 514/44 A |
| 2018/0117073 A1 | 5/2018 | Hastings | |
| 2019/0038701 A1 * | 2/2019 | Hayouka | A61K 38/03 |
| 2021/0401869 A1 | 12/2021 | Hastings | |
| 2022/0040219 A1 * | 2/2022 | Bear | A61K 31/7115 |
| 2022/0054526 A1 | 2/2022 | Hastings | |
| 2022/0064647 A1 * | 3/2022 | Oren | A61K 31/7105 |
| 2022/0213479 A1 * | 7/2022 | Kerem | A61K 45/06 |
| 2022/0220486 A1 * | 7/2022 | Kerem | A61P 11/00 |

(Continued)

FOREIGN PATENT DOCUMENTS

WO WO 2004/045543 A2 6/2004
WO WO 2014/045283 A1 3/2014

(Continued)

OTHER PUBLICATIONS

West/Cystic Fibrosis Foundation (2008. Pulmonary Exacerbations Clinical Care Guidelines. Available online at cff.org. Accessed on Oct. 3, 2024 (Year: 2008).*
Turnbull (and Davies. 2016. New drug developments in the management of cystic fibrosis lung disease. Expert Opinion on Pharmacotherapy vol. 17[8]:1103-1112) (Year: 2016).*
Kreda (2022. Oligonucleotide-based therapies for cystic fibrosis. Current Opin. Pharmacol. 66:102271) (Year: 2022).*
Spelier (et al. 2023. Readthrough compounds for nonsense mutations: bridging the translational gap. Trends Molec. Med. 29[4]:297-314) (Year: 2023).*
U.S. Appl. No. 18/574,025, filed Dec. 2023.*
Wikipedia (2024. "antibiotic", "corticosteroid", "lumacaftor-ivacaftor", and "lung". Available online at Wikipedia.org. Accessed Oct. 3, 2024) (Year: 2024).*

(Continued)

*Primary Examiner* — Nancy J Leith
*Assistant Examiner* — Ruth Sophia Arieti
(74) *Attorney, Agent, or Firm* — Mark S. Cohen; PEARL COHEN ZEDEK LATZER BARATZ LLP

(57) ABSTRACT

The present invention provides oligonucleotides capable of binding to and modulating the splicing of the pre-mRNA of the CFTR gene, including compositions comprising the oligonucleotides, and uses thereof, such as for suppressing the inclusion of a cryptic exon between exon 22 and 23 as a result of the mutation 3849+10Kb C-to-T, optionally in combination with additional CF therapeutics.

13 Claims, 23 Drawing Sheets

Specification includes a Sequence Listing.

(56) References Cited

U.S. PATENT DOCUMENTS

2022/0339236 A1* 10/2022 Karni ............... A61K 31/55
2023/0142669 A1* 5/2023 Oren ............... C12N 15/1138
514/44 A

FOREIGN PATENT DOCUMENTS

WO    WO 2015/157070 A2    10/2015
WO    WO 2016/134021 A1    8/2016

OTHER PUBLICATIONS

Vickers (et al. 2000. Effects of RNA secondary structure on cellular antisense activity. Nuc. Acid Res. 28[6]:1340-1347) (Year: 2000).*
Crooke (et al. 2008. Mechanisms of Antisense Drug Action, an Introduction. Chapter 1 in Antisense Drug Technology, Second Edition, Crooke, ed. Taylor & Francis: Florida) (Year: 2008).*
Cirak et al. "Exon skipping and dystrophin restoration in patients with Duchenne muscular dystrophy after systemic phosphorodiamidate morpholino oligomer treatment: an open-label, phase 2, dose-escalation study" The Lancet. Aug. 13, 2011;378(9791):595-605.
Friedman et al. "Correction of aberrant splicing of the cystic fibrosis transmembrane conductance regulator (CFTR) gene by antisense oligonucleotides" Journal of Biological Chemistry. Dec. 17, 1999;274(51):36193-9.
Gebski et al. "Morpholino antisense oligonucleotide induced dystrophin exon 23 skipping in mdx mouse muscle" Human molecular genetics. Aug. 1, 2003;12(15):1801-11.
Gentzsch et al. "Ion channel modulators in cystic fibrosis" Chest. Aug. 1, 2018;154(2):383-93.
Goemans et al. "Systemic administration of PRO051 in Duchenne's muscular dystrophy" New England Journal of Medicine. Apr. 21, 2011;364(16):1513-22.
Goyenvalle et al. "Prevention of dystrophic pathology in severely affected dystrophin/utrophin-deficient mice by morpholino-oligomer-medlated exon-skipping" Molecular Therapy. Jan. 1, 2010;18(1):198-205.
Hua et al. "Antisense correction of SMN2 splicing in the CNS rescues necrosis in a type III SMA mouse model" Genes & development. Aug. 1, 2010;24(15):1634-44.
International Search Report for PCT Application No. PCT/IL2020/050495 dated Aug. 6, 2020.
Kim et al. Exon-skipping antisense oligonucleotides for cystic fibrosis therapy. Proc Natl Acad Sci U S A. 2022;119(3):e2114858118.
Kinali et al. "Local restoration of dystrophin expression with the morpholino oligomer AVI-4658 in Duchenne muscular dystrophy: a single-blind, placebo-controlled, dose-escalation, proof-of-concept study" The Lancet Neurology. Oct. 1, 2009;8(10):918-28.
Mendell et al. "Eteplirsen for the treatment of Duchenne muscular dystrophy" Annals of neurology. Nov. 2013;74(5):637-47.
Porensky et al. "A single administration of morpholino antisense oligomer rescues spinal muscular atrophy in mouse" Human molecular genetics. Apr. 1, 2012;21(7):1625-38.
Van Deutekom et al. "Local dystrophin restoration with antisense oligonucleotide PRO051" New England Journal of Medicine. Dec. 27, 2007;357(26):2677-86.
Williams et al. "Oligonucleotide-mediated survival of motor neuron protein expression in CNS improves phenotype in a mouse model of spinal muscular atrophy" Journal of Neuroscience. Jun. 17, 2009;29(24):7633-8.
Dugueperoux, I., & De Braekeleer, M. (2005). The CFTR 3849+10kbC-> T and 2789+ 5G-> A alleles are associated with a mild CF phenotype. *European Respiratory Journal*, 25(3), 468-473.
Highsmith, W. E., Burch, L. H., Zhou, Z., Olsen, J. C., Boat, T. E., Spock, A., . . . & Knowles, M. R. (1994). A novel mutation in the cystic fibrosis gene in patients with pulmonary disease but normal sweat chloride concentrations. *New England Journal of Medicine*, 331(15), 974-980.

Kerem, E., Rave-Harel, N., Augarten, A., Madgar, I., Nissim-Rafinia, M., Yahav, Y., . . . & Kerem, B. (1997). A cystic fibrosis transmembrane conductance regulator splice variant with partial penetrance associated with variable cystic fibrosis presentations. *American journal of respiratory and critical care medicine*, 155(6), 1914-1920.
Kerem, B., Chiba-Falek, O., & Kerem, E. (1997). Cystic fibrosis in Jews: frequency and mutation distribution. *Genetic testing*, 1(1), 35-39.
Pranke, I. M., Hatton, A., Simonin, J., Jais, J. P., Le Pimpec-Barthes, F., Carsin, A., . . . & Sermet-Gaudelus, I. (2017). Correction of CFTR function in nasal epithelial cells from cystic fibrosis patients predicts improvement of respiratory function by CFTR modulators. *Scientific reports*, 7(1), 7375.
Cano Megías M, Guisado Vasco P, González Albarrán O, Lamas Ferreiro A, Máiz Carro L. Association of the relative change in weight and body mass index with lung function in teenagers and adults with cystic fibrosis: Influence of gender and diabetes. Endocrinol Nutr. Nov. 2015;62(9):422-9.
Chmiel JF, Konstan MW, Elborn JS. Antibiotic and anti-inflammatory therapies for cystic fibrosis. Cold Spring Harb Perspect Med. Oct. 1, 2013;3(10):a009779. doi: 10.1101/cshperspect.a009779. PMID: 23880054; PMCID: PMC3784810.
Crosby Jr, C Zhao, C Jiang, D Bai, M Katz, S Greenlee, H Kawabe, M McCaleb, D Rotin, S Guo, et al. (2017). Inhaled ENaC antisense oligonucleotide ameliorates cystic fibrosis-like lung disease in mice. J Cyst Fibros 16:671-680.
Debley JS, Barrow KA, Rich LM, Singh P, McKone EF, Nichols DP. Correlation between Ivacaftor-induced CFTR Activation in Airway Epithelial Cells and Improved Lung Function: A Proof-of-Concept Study. Ann Am Thorac Soc. Aug. 2020;17(8):1024-1027.
Deletang K, Taulan-Cadars M. Splicing mutations in the CFTR gene as therapeutic targets. Gene Ther. Aug. 2022;29(7-8):399-406. doi: 10.1038/s41434-022-00347-0. Epub Jun. 2, 2022. PMID: 35650428; PMCID: PMC9385490.
Durmowicz AG, Lim R, Rogers H, Rosebraugh CJ, Chowdhury BA. The U.S. Food and Drug Administration's Experience with Ivacaftor in Cystic Fibrosis. Establishing Efficacy Using In Vitro Data in Lieu of a Clinical Trial. Ann Am Thorac Soc. Jan. 2018;15(1):1-2.
Fey RA, MV Templin, JD McDonald, RZ Yu, JA Hutt, AP Gigliotti, SP Henry and MD Reed. (2014). Local and systemic tolerability of a 2¢O-methoxyethyl antisense oligonucleotide targeting interleukin-4 receptor-a delivery by inhalation in mouse and monkey. Inhal Toxicol 26:452-463.
Karras JC, JR Crosby, M Guha, D Tung, DA Miller, WA Gaarde, RS Geary, BP Monia and SA Gregory. (2007).Anti-inflammatory activity of inhaled IL-4 receptor-aantisense oligonucleotide in mice. Am J Respir Cell Mol Biol 36:276-285.
Ozeri-Galai E, Friedman L, Barchad-Avitzur O, Markovetz MR, Boone W, Rouillard KR, Stampfer CD, Oren YS, Hill DB, Kerem B, Hart G. Delivery Characterization of SPL84 Inhaled Antisense Oligonucleotide Drug for 3849 + 10 kb C- > T Cystic Fibrosis Patients. Nucleic Acid Ther. Oct. 2023;33(5):306-318.
Roda J, Pinto-Silva C, Silva IAI, Maia C, Almeida S, Ferreira R, Oliveira G. New drugs in cystic fibrosis: what has changed in the last decade? Ther Adv Chronic Dis. May 21, 2022;13:20406223221098136. doi: 10.1177/20406223221098136. PMID: 35620188; PMCID: PMC9128052.
Sequeiros IM, Jarad N. Factors associated with a shorter time until the next pulmonary exacerbation in adult patients with cystic fibrosis. Chron Respir Dis. Feb. 2012;9(1):9-16.
Chen et al. "Splice-modulating antisense oligonucleotides as therapeutics for inherited metabolic diseases" BioDrugs. Mar. 2024;38(2):177-203.
Cystic Fibrosis Foundation "Cystic Fibrosis Foundation Therapeutics Lab" 2025 Available online at: https://www.cff.org/research-clinical-trials/cystic-fibrosis-foundation-therapeutics-lab.; Accessed on Apr. 30, 2025.
Echigoya et al. "In silico screening based on predictive algorithms as a design tool for exon skipping oligonucleotides in Duchenne muscular dystrophy" PLoS One. Mar. 27, 2015;10(3):e0120058.

(56) References Cited

OTHER PUBLICATIONS

Martin et al. "Exon identity influences splicing induced by exonic variants and in silico prediction efficacy" Journal of Cystic Fibrosis. May 1, 2021;20(3):464-72.
Roche "New era of antibiotics potentially in sight after more than 50 years" 2024; Available online at: https://www.roche.com/stories/new-era-of-antibiotics; accessed on Apr. 30, 2025.
Wikipedia (2024. "lumacaftor-ivacaftor" AND "antibiotic", "corticosteroid" and "lung". Available online. Accessed Oct. 3, 2024.

* cited by examiner

SEQUENCE LISTING

```
Sequence total quantity: 71
SEQ ID NO: 1         moltype = RNA   length = 20
FEATURE              Location/Qualifiers
misc_feature         1..20
                     note = Synthetic
source               1..20
                     mol_type = other RNA
                     organism = synthetic construct
```

```
SEQUENCE: 1
ctgcaacaga tggaagactc                                                  20

SEQ ID NO: 2            moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 2
caacagatgg aagactctt                                                   19

SEQ ID NO: 3            moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 3
ctccagaaat caagatgac                                                   19

SEQ ID NO: 4            moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 4
tactgcaaca gatggaaga                                                   19

SEQ ID NO: 5            moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 5
atcaagatga caagtcaact                                                  20

SEQ ID NO: 6            moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 6
gtggtctcca gaaatcaag                                                   19

SEQ ID NO: 7            moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 7
gatggaagac tcttgtaat                                                   19

SEQ ID NO: 8            moltype = RNA   length = 21
FEATURE                 Location/Qualifiers
misc_feature            1..21
                        note = Synthetic
source                  1..21
                        mol_type = other RNA
                        organism = synthetic construct
SEQUENCE: 8
caagatgaca agtcaactga a                                                21

SEQ ID NO: 9            moltype = RNA   length = 22
FEATURE                 Location/Qualifiers
misc_feature            1..22
                        note = Synthetic
```

```
source                  1..22
                        mol_type = other RNA
                        organism = synthetic construct
SEQUENCE: 9
gaaatcaaga tgacaagtca ac                                              22

SEQ ID NO: 10           moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 10
accttgtggt ctccagaaa                                                  19

SEQ ID NO: 11           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 11
ccagaaatca agatgacaag                                                 20

SEQ ID NO: 12           moltype = RNA   length = 21
FEATURE                 Location/Qualifiers
misc_feature            1..21
                        note = Synthetic
source                  1..21
                        mol_type = other RNA
                        organism = synthetic construct
SEQUENCE: 12
caccatttta atactgcaac a                                               21

SEQ ID NO: 13           moltype = RNA   length = 21
FEATURE                 Location/Qualifiers
misc_feature            1..21
                        note = Synthetic
source                  1..21
                        mol_type = other RNA
                        organism = synthetic construct
SEQUENCE: 13
tggaagactc ttgtaattat t                                               21

SEQ ID NO: 14           moltype = RNA   length = 21
FEATURE                 Location/Qualifiers
misc_feature            1..21
                        note = Synthetic
source                  1..21
                        mol_type = other RNA
                        organism = synthetic construct
SEQUENCE: 14
gatgacaagt caactgaaat t                                               21

SEQ ID NO: 15           moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 15
ctttcagggt gtcttactc                                                  19

SEQ ID NO: 16           moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 16
tcagggtgtc ttactcacc                                                  19

SEQ ID NO: 17           moltype = RNA   length = 20
FEATURE                 Location/Qualifiers
```

```
misc_feature             1..20
                         note = Synthetic
source                   1..20
                         mol_type = other RNA
                         organism = synthetic construct
SEQUENCE: 17
attaccttgt ggtctccaga                                                    20

SEQ ID NO: 18            moltype = RNA   length = 21
FEATURE                  Location/Qualifiers
misc_feature             1..21
                         note = Synthetic
source                   1..21
                         mol_type = other RNA
                         organism = synthetic construct
SEQUENCE: 18
gacaagtcaa ctgaaattta g                                                  21

SEQ ID NO: 19            moltype = RNA   length = 21
FEATURE                  Location/Qualifiers
misc_feature             1..21
                         note = Synthetic
source                   1..21
                         mol_type = other RNA
                         organism = synthetic construct
SEQUENCE: 19
caactgaaat ttagatccac a                                                  21

SEQ ID NO: 20            moltype = RNA   length = 21
FEATURE                  Location/Qualifiers
misc_feature             1..21
                         note = Synthetic
source                   1..21
                         mol_type = other RNA
                         organism = synthetic construct
SEQUENCE: 20
agtcaactga aatttagatc c                                                  21

SEQ ID NO: 21            moltype = RNA   length = 21
FEATURE                  Location/Qualifiers
misc_feature             1..21
                         note = Synthetic
source                   1..21
                         mol_type = other RNA
                         organism = synthetic construct
SEQUENCE: 21
gtgtcttact caccatttta a                                                  21

SEQ ID NO: 22            moltype = RNA   length = 18
FEATURE                  Location/Qualifiers
misc_feature             1..18
                         note = Synthetic
source                   1..18
                         mol_type = other RNA
                         organism = synthetic construct
SEQUENCE: 22
gtgtcttact caccattt                                                      18

SEQ ID NO: 23            moltype = RNA   length = 19
FEATURE                  Location/Qualifiers
misc_feature             1..19
                         note = Synthetic
source                   1..19
                         mol_type = other RNA
                         organism = synthetic construct
SEQUENCE: 23
ctcaccattt taatactgc                                                     19

SEQ ID NO: 24            moltype = RNA   length = 18
FEATURE                  Location/Qualifiers
misc_feature             1..18
                         note = Synthetic
source                   1..18
                         mol_type = other RNA
                         organism = synthetic construct
SEQUENCE: 24
gacaagtcaa ctgaaatt                                                      18

SEQ ID NO: 25            moltype = RNA   length = 20
```

```
FEATURE              Location/Qualifiers
misc_feature         1..20
                     note = Synthetic
source               1..20
                     mol_type = other RNA
                     organism = synthetic construct
SEQUENCE: 25
cttactcacc attttaatac                                                20

SEQ ID NO: 26        moltype = RNA   length = 18
FEATURE              Location/Qualifiers
misc_feature         1..18
                     note = Synthetic
source               1..18
                     mol_type = other RNA
                     organism = synthetic construct
SEQUENCE: 26
gtcttactca ccatttta                                                  18

SEQ ID NO: 27        moltype = RNA   length = 19
FEATURE              Location/Qualifiers
misc_feature         1..19
                     note = Synthetic
source               1..19
                     mol_type = other RNA
                     organism = synthetic construct
SEQUENCE: 27
caagtcaact gaaatttag                                                 19

SEQ ID NO: 28        moltype = RNA   length = 19
FEATURE              Location/Qualifiers
misc_feature         1..19
                     note = Synthetic
source               1..19
                     mol_type = other RNA
                     organism = synthetic construct
SEQUENCE: 28
cttgtaatta tttttacat                                                 19

SEQ ID NO: 29        moltype = RNA   length = 25
FEATURE              Location/Qualifiers
misc_feature         1..25
                     note = Synthetic
source               1..25
                     mol_type = other RNA
                     organism = synthetic construct
SEQUENCE: 29
aaatcaagat gacaagtcaa ctgaa                                          25

SEQ ID NO: 30        moltype = RNA   length = 25
FEATURE              Location/Qualifiers
misc_feature         1..25
                     note = Synthetic
source               1..25
                     mol_type = other RNA
                     organism = synthetic construct
SEQUENCE: 30
cttgtggtct ccagaaatca agatg                                          25

SEQ ID NO: 31        moltype = RNA   length = 25
FEATURE              Location/Qualifiers
misc_feature         1..25
                     note = Synthetic
source               1..25
                     mol_type = other RNA
                     organism = synthetic construct
SEQUENCE: 31
aacagatgga agactcttgt aatta                                          25

SEQ ID NO: 32        moltype = RNA   length = 25
FEATURE              Location/Qualifiers
misc_feature         1..25
                     note = Synthetic
source               1..25
                     mol_type = other RNA
                     organism = synthetic construct
SEQUENCE: 32
tcagggtgtc ttactcacca tttta                                          25
```

-continued

```
SEQ ID NO: 33           moltype = RNA   length = 18
FEATURE                 Location/Qualifiers
misc_feature            1..18
                        note = Synthetic
source                  1..18
                        mol_type = other RNA
                        organism = synthetic construct
SEQUENCE: 33
gaccacttgc cacccatc                                                 18

SEQ ID NO: 34           moltype = RNA   length = 6130
FEATURE                 Location/Qualifiers
source                  1..6130
                        mol_type = mRNA
                        organism = Homo sapiens
SEQUENCE: 34
aattggaagc aaatgacatc acagcaggtc agagaaaaag ggttgagcgg caggcaccca    60
gagtagtagg tctttggcat taggagcttg agcccagacg gccctagcag ggaccccagc   120
gcccgagaga ccatgcagag gtcgcctctg gaaaaggcca gcgttgtctc caaacttttt   180
ttcagctgga ccagaccaat tttgaggaaa ggatacagac agcgcctgga attgtcagac   240
atataccaaa tcccttctgt tgattctgct gacaatctat ctgaaaaatt gaaagagaat   300
gggatagaga gctggcttca aagaaaaatc ctaaactaat taatgccctt cggcgatgtt   360
ttttctggag atttatgttc tatggaatct ttttatattt aggggaagtc accaaagcag   420
tacagcctct cttactggga agaatcatag cttcctatga cccggataac aaggaggaac   480
gctctatcgc gatttatcta ggcataggct tatgccttct ctttattgtg aggacactgc   540
tcctacaccc agccattttt ggccttcatc acattggaat cagatgagaa atagctatgt   600
ttagtttgat ttataagaag actttaaagc tgtcaagccg tgttctagat aaaataagta   660
ttggacaact tgttagtctc cttttccaaca acctgaacaa atttgatgaa ggacttgcat   720
tggcacattt cgtgtggatc gctcctttgc aagtggcact cctcatgggg ctaatctggg   780
agttgttaca ggcgtctgcc ttctgtggac ttggttttca gatagtcctt gccctttttc   840
aggctgggct agggagaatg atgatgaagt acagagatca gagagctggg aagatcagtg   900
aaagactgt gattacctca gaaatgattg aaaatatcca atctgttaag gcatactgct   960
gggaagaagc aatggaaaaa atgattgaaa acttaagaca aacagaactg aaactgactc  1020
ggaaggcagc ctatgtgaga tacttcaata gctcagcctt cttcttctca gggttcttg   1080
tggtgttttt atctgtgctt ccctatgcac taatcaaagg aatcatcctc cggaaaatat  1140
tcaccaccat ctcattctgc attgttctgc gcatggcgt cactcggcaa tttccctggg  1200
ctgtacaaac atggtatgac tctcttggag caataaacaa atacaggat ttcttacaaa  1260
agcaagaata taagacattg gaatataact taacgactac agaagtagtg atggagaatg  1320
taacagcctt ctgggaggag ggatttgggg aattatttga gaaagcaaaa caaaacaata  1380
acaatagaaa aacttctaat ggtgatgaca gcctcttctt cagtaatttc tcacttcttg  1440
gtactcctgt cctgaaagat attaattca agatagaaag gaacagttg ttggcggttg  1500
ctggatccac tggagcaggc aagacttcac ttcaatggt gattatggga gaactggagc  1560
cttcagaggg taaaattaag cacagtggaa gaatttcatt ctgttctcag ttttcctgga  1620
ttatgcctgg caccattaaa gaaaatatca tctttggtgt ttcctatgat gaatatagat  1680
acagaagcgt catcaaagca tgccaactag aagaggacat ctccaagttt gcagagaaag  1740
acaatatagt tcttggagaa ggtggaatca cactgagtgg aggtcaacga gcaagaattt  1800
ctttagcaag agcagtatac aaagatgctg atttgtattt attagactct ccttttggat  1860
acctagatgt tttaacagaa aaagaaata ttgaaagctg tgtctgtaaa ctgatggcta  1920
acaaaactag gatttttggtc acttctaaaa tggaacattt aaagaaagct gacaaaatat  1980
taatttttgca tgaaggtagc agctattttt atgggacatt ttcagaactc caaaatctac  2040
agcagcactt tagctcaaaa ctcatggat gtgattctt cgaccaattt agtgcagaaa  2100
gaagaaattc aatcctaact gagaccttac accgtttctc attagaagga gatgctcctg  2160
tctcctggac agaaacaaa aaacaatctt taaacagac tggagagttt ggggaaaaaa  2220
ggaagaattc tattctcaat ccaatcaact ctatacgaaa attttccatt gtgcaaaaga  2280
ctcccttaca atgaatggc atcgaagagg atttctgatga gccttttagag agaaggctgt  2340
ccttagtacc agattctgag cagggagagg cgatactgcc tcgcatcagc gtgatcagca  2400
ctggccccac gcttcaggca cgaaggaggc agtctgtcct gaacctgatg acacactcag  2460
ttaaccaagg tcagaacatt caccgaaaga acagcatc cacacgaaaa gtgtcactgg  2520
cccctcaggc aaacttgact gaactggata tatattcaag aaggttatct caagaaactg  2580
gcttggaaat aagtgaagaa attaacgaag aagactaaaa ggagtgcttt tttgatgata  2640
tggagagcat accagcagtg actacatgga acacatacct tcgatatatt actgtccaca  2700
agagcttaat ttttgtgcta atttggtgct tagtaatttt tctggcagag gtggctgctt  2760
ctttggttgt gctgtggctc cttggaaaca ctcctcttca agacaaaggg aatagtactc  2820
atagtagaaa taacagctat gcagtgatta tcaccagcac cagttcgtat tatgtgttta  2880
acatttacgt gggagtagcc gacacttgc ttgctatggg attcttcaga ggtctaccac  2940
tggtgcatac tctaatcaca gtgtcgaaaa ttttacacca caaatgttta cattctgttc  3000
ttcaagcacc tatgtcaacc ctcaacacgt gaaagcagg tgggattctt aatagattct  3060
ccaaagatat agcaattttg gatgaccttc tgcctcttca catatttgac ttcatccagt  3120
tgttattaat tgtgattgga gctatagcag ttgtcgcagt tttacaaccc tacatctgtt  3180
ttgcaacagt gccagtgata gtggctttta tttgttgag agcatatttc ctccaaacct  3240
cacagcaact caaacaactg gaatctgaag caggagtcc aatttcact catcttgtta  3300
caagcttaaa aggactatgg acacttcgtg ccttcggacg gcagccttac tttgaaactc  3360
tgttccacaa agctctgaat ttacatactg ccaactggtt cttgtacctg tcaacactgc  3420
gctggttcca aatgagaata gaatgattt ttgtcatctt cttcattgct gttacctca  3480
ttttccattt aacaacagga gaaggagaag gaagagttgg tattatcctg acttagcca  3540
tgaatatcat gagtacattg cagtgggctg taaactccag catagatgtg gatagcttga  3600
tgcgatctgt gagccgagtc tttaagttca ttgacatgcc aacagaaggt aaacctacca  3660
agtcaaccaa accatacaag aatggccaac tctcgaaagt tatgattatt gagaaattcac  3720
acgtgaagaa agatgacatc tggcccctcag ggggccaaat gactgtcaaa gatctcacag  3780
```

```
caaaatacac agaaggtgga aatgccatat tagagaacat ttccttctca ataagtcctg  3840
gccagagggt gggcctcttg ggaagaactg gatcagggaa gagtactttg ttatcagctt  3900
ttttgagact actgaacact gaaggagaaa tccagatcga tggtgtgtct tgggattcaa  3960
taactttgca acagtggagg aaagcctttg gagtgatacc acagaaagta tttatttttt  4020
ctggaacatt tagaaaaaac ttggatccct atgaacagtg gagtgatcaa gaaatatgga  4080
aagttgcaga tgaggttggg ctcagatctg tgatagaaca gtttcctggg aagcttgact  4140
ttgtccttgt ggatggggc tgtgtcctaa gccatggcca caagcagttg atgtgcttgg   4200
ctagatctgt tctcagtaag gcgaagatct tgctgcttga tgaacccagt gctcatttgg  4260
atccagtaac ataccaaata attagaagaa ctctaaaaca agcatttgct gattgcacag  4320
taattctctg tgaacacagg ataagaagcaa tgctggaatg ccaacaattt ttggtcatag  4380
aagagaacaa agtgcggcag tacgattcca tccagaaact gctgaacgag aggagcctct  4440
tccggcaagc catcagcccc tccgacaggg tgaagctctt tccccaccgg aactcaagca  4500
agtgcaagtc taagccccag attgctgctc tgaaagagga gacagaagaa gaggtgcaag  4560
atacaaggct ttagagagca gcataaatgt tgacatggga catttgctca tggaattgga  4620
gctcgtggga cagtcacctc atggaattgg agctcgtgga acagttacct ctgcctcaga  4680
aaacaaggat gaattaagtt tttttttaaa aagaaacat ttggtaaggg aattgaggac   4740
actgatatgg gtcttgataa atggcttcct ggcaatagtc aaattgtgtg aaaggtactt  4800
caaatccttg aagatttacc acttgtgttt tgcaagccga attttcctga aaaccctgc   4860
catgtgctag taattggaaa ggcagctcta aatgtcaatc agcctagttg atcagcttat  4920
tgtcagtgag actcgttaa tttgtagtgt tggagaagaa ctgaaatcat acttcttagg   4980
gttatgatta agtaatgata actggaaact tcagcggtt ataagctt gtattccttt    5040
ttctctcctc tccccatgat gtttagaaac acaactatat tgtttgctaa gcattccaac  5100
tatctcattt ccaagcaagt attagaatac cacaggaacc acaagactgc acatcaaaat  5160
atgcccccatt caacatctag tgagcagtca ggaaagagaa cttccagatc ctggaaatca  5220
gggttagtat tgtccaggtc taccaaaaat ctcaatattt cagataatca caatacatcc  5280
cttacctggg aaagggctgt tataatcttt cacagggaca aggatggttc ccttgatgaa  5340
gaagttgata tgccttttcc caactccaga aagtgacaag ctcacagacc tttgaactag  5400
agtttagctg gaaaagtatg ttagtgcaaa ttgtcacagg acagcccttc tttccacaga  5460
agctccaggt gagggtgtg taagtagata ggccatgggc actgtgggta gacacacatg   5520
aagtccaagc atttagatgt ataggttgat ggtggtagct tttcaggcta gatgtatgta  5580
cttcatgctg tctacactaa gagagaatga gagacacact gaagaagcac caatcatgaa  5640
ttagtttat atgcttctgt tttataattt tgtgaagcaa aatttttct ctaggaaata    5700
tttatttaaa taatgtttca aacatatata acaatgctgt atttttaaaag aatgattatg  5760
aattacattt gtataaaata atttttat ttgaaatatt gactttttat ggcactagta    5820
tttctatgaa atattatgtt aaaactggga caggggagaa cctagggtga tattaaccag  5880
gggccatgaa tcacctttg gtctggaggg aagccttggg gctgatgcag ttgttgccca   5940
cagctgtatg attcccagcc agcacagcct cttagatgca gttctgaaga agatggtacc  6000
accagtctga ctgtttccat caagggtaca ctgccttctc aactccaaac tgactcttaa  6060
gaagactgca ttatatttat tactgtaaga aaatatcact tgtcaataaa atccatacat  6120
ttgtgtgaaa                                                         6130

SEQ ID NO: 35          moltype = DNA   length = 84
FEATURE                Location/Qualifiers
source                 1..84
                       mol_type = genomic DNA
                       organism = Homo sapiens
SEQUENCE: 35
ttgacttgtc atcttgattt ctggagacca caaggtaatg aaaaataatt acaagagtct    60
tccatctgtt gcagtattaa aatg                                           84

SEQ ID NO: 36          moltype = RNA   length = 6216
FEATURE                Location/Qualifiers
source                 1..6216
                       mol_type = mRNA
                       organism = Homo sapiens
SEQUENCE: 36
aattggaagc aaatgacatc acagcaggtc agagaaaaag ggttgagcgg caggcaccca    60
gagtagtagg tctttggcat taggagcttg agcccagacg gccctagcag ggaccccagc   120
gcccgagaga ccatgcagag gtcgcctctg gaaaaggcca gcgttgtctc caaactttg    180
ttcagctgga ccagaccaat tttgaggaaa ggatacagac agcgcctgga attgtcagac   240
atataccaaa tcccttctgt tgattctgct gacaatctat ctgaaaaatt ggaaagagaa   300
tgggatagag agctggcttc aaagaaaaat cctaaactca ttaatgccct tcggcgatgt   360
ttttctgga gatttatgtt ctatggaatc tttttatatt taggggaagt caccaaaagca  420
gtacagcctc tcttactggg aagaatcata gcttcctatg acccgataa caaggaggaa   480
cgctctatcg cgatttatct aggcataggc ttatgccttc tctttattgt gaggacactg   540
ctcctacacc cagccatttt tggccttcat cacattggaa tgcagatgag aatagctatg   600
tttagtttga tttataagaa gactttaaag ctgtcaagcc gtgttctaga taaaataagt   660
attggacaac ttgttagtct ccttccaac aacctgaaca aatttgatga aggactttgca   720
ttggcacatt tcgtgtggat cgctcctttg caagtggcac tcctcatgag gctaatctgg   780
gagttgttac aggcgtctgc cttctgtgga cttggtttcc tgatagtcct tgccctttt   840
caggctgggc tagggagaat gatgatgaag tacagagatc agagagctgg gaagatcagt   900
gaaagacttg tgattacctc agaaatgatt gaaaatatcc aatctgttaa ggcatactgc  960
tgggaagaag caatggaaaa aatgattgaa aacttaagac aaacagaact gaaactgact  1020
cggaaggcag cctatgtgag atacttcaat agctcagcct tcttcttctc agggttcttt  1080
gtggtgtttt tatctgtgct tcccatgca ctaatcaaag gaatcatcct ccggaaaata   1140
ttcaccacca tctcattctg cattgttctg cgcatggcgg tcactcggca atttcctgg   1200
gctgtacaaa catggtatga ctctcttgga gcaataaaca aaatacagga ttcttacaa   1260
aagcaagat ataagacatt ggaatataac ttaacgacta cagaagtagt gatggagaat   1320
gtaacagcct tctgggagga gggatttggg gaattatttg agaaagcaaa acaaaacaat  1380
```

```
aacaatagaa aaacttctaa tggtgatgac agcctcttct tcagtaattt ctcacttctt 1440
ggtactcctg tcctgaaaga tattaatttc aagatagaaa gaggacagtt gttggcggtt 1500
gctggatcca ctggagcagg caagacttca cttctaatgg tgattatggg agaactggag 1560
ccttcagagg gtaaaattaa gcacagtgga agaatttcat tctgttctca gttttcctgg 1620
attatgcctg gcaccattaa agaaaatatc atctttggtg tttcctatga tgaatataga 1680
tacagaagcg tcatcaaagc atgccaacta gaagaggaca tctccaagtt tgcagagaaa 1740
gacaatatag ttcttggaga aggtggaatc acactgagtg gaggtcaacg agcaagaatt 1800
tctttagcaa gagcagtata caaagatgct gatttgtatt tattagactc tccttttgga 1860
tacctagatg ttttaacaga aaaagaaata tttgaaagct gtgtctgtaa actgatggct 1920
aacaaaacta ggattttggt cacttctaaa atggaaacat taaagaaagc tgacaaaata 1980
ttaattttgc atgaaggtag cagctatttt tatgggacat tttcagaact ccaaaatcta 2040
cagccagact ttagctcaaa actcatggga tgtgattctt tcgaccaatt tagtgcagaa 2100
agaagaaatt caatcctaac tgagaccttA caccgtttct cattagaagg agatgctcct 2160
gtctcctgga cagaaacaaa aaaacaatct tttaaacaga ctggagagtt tggggaaaaa 2220
aggaagaatt ctattctcaa tccaatcaac tctatacgaa aattttccat tgtgcaaaag 2280
actcccttac aaatgaatgg catcgaagag gattctgatg agcctttaga gagaaggctg 2340
tccttagtac cagattctga gcaggagag gcgatactgc ctcgcatcag cgtgatcagc 2400
actggcccca cgcttcaggc acgaaggagg cagtctgtcc tgaacctgat gacacactca 2460
gttaaccaag gtcagaacat tcaccgaaaa acaacagcat ccacacgaaa agtgtcactg 2520
gcccctcagg caaacttgac tgaactggat atatattcaa gaaggttatc tcaagaaact 2580
ggcttggaaa taagtgaaga aattaacgaa gaagacttaa aggagtgctt ttttgatgat 2640
atggagagca taccagcagt gactacatgg aacacatacc ttcgatatat tactgtccac 2700
aagagcttaa tttttgtgct aatttggtgc ttagtaattt ttctggcaga ggtggctgct 2760
tctttggttg tgctgtggct cctttggaaac actcctcttc aagacaaagg gaatagtact 2820
catagtagaa ataacagcta tgcagtgatt atcaccagca ccagttcgta ttatgtgttt 2880
tacatttacg tgggagtagc cgacactttg cttgctatgg gattcttcag aggtctacca 2940
ctggtgcata ctctaatcac agtgtcgaaa attttacacc acaaaatgtt acattctgtt 3000
cttcaagcac ctatgtcaac cctcaacacg ttgaaagcag gtgggattct taatagattc 3060
tccaaagata tagcaatttt ggatgacctt ctgcctctta ccatatttga cttcatccag 3120
ttgttattaa ttgtgattgg agctatagca gttgtcgcag tttacaaacc ctacatcttt 3180
gttgcaacag tgccagtgat agtggctttt attatgttga gagcatattt cctccaaacc 3240
tcacagcaac tcaaacaact ggaatctgaa ggcaggagtc caattttcac tcatcttgtt 3300
acaagcttaa aaggactatg gacacttcgt gccttcggac ggcagcctta ctttgaaact 3360
ctgttccaca aagctctgaa tttacatact gccaactggt tcttgtacct gtcaacactg 3420
cgctggttcc aaatgagaat agaaatgatt tttgtcatct tcttcattgc tgttaccttc 3480
atttccattt taacaacagg agaaggagaa ggaagagttg gtattatcct gacttttagcc 3540
atgaatatca tgagtacatt gcagtgggct gtaaactcca gcatagatgt ggatagcttg 3600
atgcgatctg tgagccgagt ctttaagttc attgacatgc caacagaagg taaacctacc 3660
aagtcaacca aaccatacaa gaatggccaa ctctcgaaca ttatgattat tgagaattca 3720
cacgtgaaga aagatgacat ctggccctca gggggccaaa tgactgtcaa agatctcaca 3780
gcaaaataca cagaaggtgg aaatgccata ttagagaaca tttccttctc aataagtcct 3840
ggccagaggt tgacttgtca tcttgatttc tggagaccaa aggtaatga aaaataatta 3900
caagagtctt ccatctgttg cagtattaaa atggtgggac tcttgggaag aactggatca 3960
gggaagagta ctttgttatc agcttttttg agactactga acactgaagg agaaatccag 4020
atcgatggtg tgtcttggga ttcaataact ttgcaacagt ggaggaaagc ctttggagtg 4080
ataccacaga aagtatttat tttttctgga acatttagaa aaaacttgga tccctatgaa 4140
cagtggagtg atcaagaaat atggaaagtt gcagatgagg ttgggctcag atctgtgata 4200
gaacagtttc ctgggaagct tgactttgtc cttgtggatg ggggctgtgt cctaagccat 4260
ggccacaagc agttgatgtg cttggctaga tctgttctca gtaaggcgaa gatcttgctg 4320
cttgatgaac ccagtgctca tttggatcca gtaacatacc aaataattag aagaactcta 4380
aaacaagcat ttgctgattg cacagtaatt tctgtgaac acaggataga agcaatgctg 4440
gaatgccaac aattttttggt catagaagag aacaaagtgc ggcagtacga ttccatccag 4500
aaaactgctga acgagaggag cctcttccgg caagccatca gcccctccga cagggtgaag 4560
ctcttttcccc accggaactc aagcaagtgc aagtctaagc cccagattgc tgctctgaaa 4620
gaggagacag aagaagaggt gcaagataca aggcttttaga gagcagcata aatgttgaca 4680
tgggacattt gctcatgaa ttggagctcg tgggacagtc acctcatgga attggagctc 4740
gtggaacagt tacctctgcc tcagaaaaca aggatgaatt aagtttttt ttaaaaaga 4800
aacatttggt aaggggaatt gaggacactg atatgggtct tgataaatgg cttcctggca 4860
atagtcaaat tgtgtgaaag gtacttcaaa tccttgaaga tttaccactt gtgttttgca 4920
agccagattt tcctgaaaac ccttgccatg tgctagtaat tggaaaggca gctctaaatg 4980
tcaatcagcc tagttgatca gcttattgtc tagtgaaact cgttaatttg tagtgttgga 5040
gaagaactga aatcatactt cttagggtta tgattaagta atgataactg gaaacttcag 5100
cggtttatat aagcttgtat tccttttcct ctcctctccc catgatgttt agaaacacaa 5160
ctatattgtt tgctaagcat tccaactatc tcatttccaa gcaagtatta gaataccaca 5220
ggaaccacaa gactgcacat caaaatatgc cccattcaac atctagtgag cagtcaggaa 5280
agagaacttc cagatcctgg aaatcagggt tagtattgtc caggtctacc aaaaatctca 5340
atatttcaga taatcacaat acatccctta cctgggaaag ggctgttata atctttcaca 5400
ggggacagga tggttccctt gatgaagaag ttgatatgcc ttttcccaac tccagaaagt 5460
gacaagctca cagacctttg aactagagtt tagctgaaga agtatgttag tgcaaattgt 5520
cacaggacag ccccttctttc cacagaagct ccaggtagag ggtgttaag tagataggcc 5580
atgggcactg tgggtagaca cacatgaagt ccaagcattt agatgtatag gttgatggtg 5640
gtatgttttc aggctagatg tatgtacttc atgctgtcta cactaagaga gaatgagaga 5700
cacactgaag aagcaccaat catgaattag ttttatatgc ttctgttta taattttgtg 5760
aagcaaaatt tttctctag gaaatattta tttaaatagt gtttcaaaca tataacaa 5820
tgctgtattt taaagaatg attatgaatt acatttgtat aaaataattt ttatatttga 5880
aatattgact tttatggca ctagtatttc tatgaaatat tatgttaaaa ctgggacagg 5940
ggagaaccta gggtgatatt aaccaggggc catgaatcac ttttggtct ggagggaagc 6000
cttggggctg atgcagttgt tgcccacagc tgtatgattc ccagccagca cagcctctta 6060
gatgcagttc tgaagaagat ggtaccacca gtctgactgt ttccatcaag ggtacactgc 6120
```

```
cttctcaact ccaaactgac tcttaagaag actgcattat atttattact gtaagaaaat    6180
atcacttgtc aataaaatcc atacatttgt gtgaaa                              6216

SEQ ID NO: 37           moltype = DNA   length = 284
FEATURE                 Location/Qualifiers
source                  1..284
                        mol_type = genomic DNA
                        organism = Homo sapiens
SEQUENCE: 37
aagcagcata ttctcaatac tatgtttcat taataattaa tagagatata tgaacacata     60
aaagattcaa ttataatcac cttgtggatc taaatttcag ttgacttgtc atcttgattt    120
ctggagacca caaggtaatg aaaaataatt acaagagtct tccatctgtt gcagtattaa    180
aatggtgagt aagacaccct gaaaggaaat gttctattca tggtacaatg caattacagc    240
tagcaccaaa ttcaacactg tttaactttc aacatattat tttg                     284

SEQ ID NO: 38           moltype =   length =
SEQUENCE: 38
000

SEQ ID NO: 39           moltype = RNA   length = 14
FEATURE                 Location/Qualifiers
misc_feature            1..14
                        note = Synthetic
source                  1..14
                        mol_type = other RNA
                        organism = synthetic construct
SEQUENCE: 39
caacagatgg aaga                                                       14

SEQ ID NO: 40           moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 40
ctgcaacaga tggaagact                                                  19

SEQ ID NO: 41           moltype = RNA   length = 19
FEATURE                 Location/Qualifiers
misc_feature            1..19
                        note = Synthetic
source                  1..19
                        mol_type = other RNA
                        organism = synthetic construct
SEQUENCE: 41
tgcaacagat ggaagactc                                                  19

SEQ ID NO: 42           moltype = RNA   length = 18
FEATURE                 Location/Qualifiers
misc_feature            1..18
                        note = Synthetic
source                  1..18
                        mol_type = other RNA
                        organism = synthetic construct
SEQUENCE: 42
ctgcaacaga tggaagac                                                   18

SEQ ID NO: 43           moltype = RNA   length = 18
FEATURE                 Location/Qualifiers
misc_feature            1..18
                        note = Synthetic
source                  1..18
                        mol_type = other RNA
                        organism = synthetic construct
SEQUENCE: 43
gcaacagatg gaagactc                                                   18

SEQ ID NO: 44           moltype = RNA   length = 18
FEATURE                 Location/Qualifiers
misc_feature            1..18
                        note = Synthetic
source                  1..18
                        mol_type = other RNA
                        organism = synthetic construct
SEQUENCE: 44
tgcaacagat ggaagact                                                   18
```

```
SEQ ID NO: 45          moltype = RNA  length = 17
FEATURE                Location/Qualifiers
misc_feature           1..17
                       note = Synthetic
source                 1..17
                       mol_type = other RNA
                       organism = synthetic construct
SEQUENCE: 45
ctgcaacaga tggaaga                                                      17

SEQ ID NO: 46          moltype = RNA  length = 17
FEATURE                Location/Qualifiers
misc_feature           1..17
                       note = Synthetic
source                 1..17
                       mol_type = other RNA
                       organism = synthetic construct
SEQUENCE: 46
caacagatgg aagactc                                                      17

SEQ ID NO: 47          moltype = RNA  length = 17
FEATURE                Location/Qualifiers
misc_feature           1..17
                       note = Synthetic
source                 1..17
                       mol_type = other RNA
                       organism = synthetic construct
SEQUENCE: 47
tgcaacagat ggaagac                                                      17

SEQ ID NO: 48          moltype = RNA  length = 17
FEATURE                Location/Qualifiers
misc_feature           1..17
                       note = Synthetic
source                 1..17
                       mol_type = other RNA
                       organism = synthetic construct
SEQUENCE: 48
gcaacagatg gaagact                                                      17

SEQ ID NO: 49          moltype = RNA  length = 18
FEATURE                Location/Qualifiers
misc_feature           1..18
                       note = Synthetic
source                 1..18
                       mol_type = other RNA
                       organism = synthetic construct
SEQUENCE: 49
ctccagaaat caagatga                                                     18

SEQ ID NO: 50          moltype = RNA  length = 18
FEATURE                Location/Qualifiers
misc_feature           1..18
                       note = Synthetic
source                 1..18
                       mol_type = other RNA
                       organism = synthetic construct
SEQUENCE: 50
tccagaaatc aagatgac                                                     18

SEQ ID NO: 51          moltype = RNA  length = 17
FEATURE                Location/Qualifiers
misc_feature           1..17
                       note = Synthetic
source                 1..17
                       mol_type = other RNA
                       organism = synthetic construct
SEQUENCE: 51
ctccagaaat caagatg                                                      17

SEQ ID NO: 52          moltype = RNA  length = 17
FEATURE                Location/Qualifiers
misc_feature           1..17
                       note = Synthetic
source                 1..17
                       mol_type = other RNA
                       organism = synthetic construct
SEQUENCE: 52
ccagaaatca agatgac                                                      17
```

```
SEQ ID NO: 53             moltype = RNA   length = 17
FEATURE                   Location/Qualifiers
misc_feature              1..17
                          note = Synthetic
source                    1..17
                          mol_type = other RNA
                          organism = synthetic construct
SEQUENCE: 53
tccagaaatc aagatga                                                       17

SEQ ID NO: 54             moltype = RNA   length = 18
FEATURE                   Location/Qualifiers
misc_feature              1..18
                          note = Synthetic
source                    1..18
                          mol_type = other RNA
                          organism = synthetic construct
SEQUENCE: 54
caacagatgg aagactct                                                      18

SEQ ID NO: 55             moltype = RNA   length = 18
FEATURE                   Location/Qualifiers
misc_feature              1..18
                          note = Synthetic
source                    1..18
                          mol_type = other RNA
                          organism = synthetic construct
SEQUENCE: 55
aacagatgga agactctt                                                      18

SEQ ID NO: 56             moltype = RNA   length = 17
FEATURE                   Location/Qualifiers
misc_feature              1..17
                          note = Synthetic
source                    1..17
                          mol_type = other RNA
                          organism = synthetic construct
SEQUENCE: 56
acagatggaa gactctt                                                       17

SEQ ID NO: 57             moltype = RNA   length = 17
FEATURE                   Location/Qualifiers
misc_feature              1..17
                          note = Synthetic
source                    1..17
                          mol_type = other RNA
                          organism = synthetic construct
SEQUENCE: 57
aacagatgga agactct                                                       17

SEQ ID NO: 58             moltype = RNA   length = 18
FEATURE                   Location/Qualifiers
misc_feature              1..18
                          note = Synthetic
source                    1..18
                          mol_type = other RNA
                          organism = synthetic construct
SEQUENCE: 58
tactgcaaca gatggaag                                                      18

SEQ ID NO: 59             moltype = RNA   length = 18
FEATURE                   Location/Qualifiers
misc_feature              1..18
                          note = Synthetic
source                    1..18
                          mol_type = other RNA
                          organism = synthetic construct
SEQUENCE: 59
actgcaacag atggaaga                                                      18

SEQ ID NO: 60             moltype = RNA   length = 17
FEATURE                   Location/Qualifiers
misc_feature              1..17
                          note = Synthetic
source                    1..17
                          mol_type = other RNA
                          organism = synthetic construct
```

-continued

```
SEQUENCE: 60
tactgcaaca gatggaa                                              17

SEQ ID NO: 61          moltype = RNA   length = 17
FEATURE                Location/Qualifiers
misc_feature           1..17
                       note = Synthetic
source                 1..17
                       mol_type = other RNA
                       organism = synthetic construct
SEQUENCE: 61
actgcaacag atggaag                                              17

SEQ ID NO: 62          moltype = RNA   length = 19
FEATURE                Location/Qualifiers
misc_feature           1..19
                       note = Synthetic
source                 1..19
                       mol_type = other RNA
                       organism = synthetic construct
SEQUENCE: 62
atcaagatga caagtcaac                                            19

SEQ ID NO: 63          moltype = RNA   length = 19
FEATURE                Location/Qualifiers
misc_feature           1..19
                       note = Synthetic
source                 1..19
                       mol_type = other RNA
                       organism = synthetic construct
SEQUENCE: 63
tcaagatgac aagtcaact                                            19

SEQ ID NO: 64          moltype = RNA   length = 18
FEATURE                Location/Qualifiers
misc_feature           1..18
                       note = Synthetic
source                 1..18
                       mol_type = other RNA
                       organism = synthetic construct
SEQUENCE: 64
atcaagatga caagtcaa                                             18

SEQ ID NO: 65          moltype = RNA   length = 18
FEATURE                Location/Qualifiers
misc_feature           1..18
                       note = Synthetic
source                 1..18
                       mol_type = other RNA
                       organism = synthetic construct
SEQUENCE: 65
caagatgaca agtcaact                                             18

SEQ ID NO: 66          moltype = RNA   length = 18
FEATURE                Location/Qualifiers
misc_feature           1..18
                       note = Synthetic
source                 1..18
                       mol_type = other RNA
                       organism = synthetic construct
SEQUENCE: 66
tcaagatgac aagtcaac                                             18

SEQ ID NO: 67          moltype = RNA   length = 17
FEATURE                Location/Qualifiers
misc_feature           1..17
                       note = Synthetic
source                 1..17
                       mol_type = other RNA
                       organism = synthetic construct
SEQUENCE: 67
atcaagatga caagtca                                              17

SEQ ID NO: 68          moltype = RNA   length = 17
FEATURE                Location/Qualifiers
misc_feature           1..17
                       note = Synthetic
```

```
source                  1..17
                        mol_type = other RNA
                        organism = synthetic construct
SEQUENCE: 68
aagatgacaa gtcaact                                              17

SEQ ID NO: 69           moltype = RNA  length = 17
FEATURE                 Location/Qualifiers
misc_feature            1..17
                        note = Synthetic
source                  1..17
                        mol_type = other RNA
                        organism = synthetic construct
SEQUENCE: 69
tcaagatgac aagtcaa                                              17

SEQ ID NO: 70           moltype = RNA  length = 17
FEATURE                 Location/Qualifiers
misc_feature            1..17
                        note = Synthetic
source                  1..17
                        mol_type = other RNA
                        organism = synthetic construct
SEQUENCE: 70
caagatgaca agtcaac                                              17

SEQ ID NO: 71           moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 71
aattattttt cattaccttg                                           20
```

RESTORATION OF THE CFTR FUNCTION BY SPLICING MODULATION

CROSS-REFERENCE TO RELATED APPLICATIONS

This application is a Continuation of U.S. patent application Ser. No. 17/607,908 filed 1 Nov. 2021 which is a National Phase Application of PCT International Application No. PCT/IL2020/050495, International Filing Date 5 May 2020, claiming the benefit of U.S. Patent Application No. 62/843,469, filed 5 May 2019, which are hereby incorporated by reference in their entirety.

SEQUENCE LISTING STATEMENT

A Sequence Listing conforming to the rules of WIPO Standard ST.26 is hereby incorporated by reference. The Sequence Listing has been filed as an electronic document encoded as XML in UTF-8 text. The electronic document, created on May 2, 2024, is entitled "P-607045-US1-SEQ-LIST-02MAY24.xml", and is 101,000 bytes in size.

FIELD OF THE INVENTION

The present invention relates to oligonucleotides capable of binding to a Cystic Fibrosis Trans-membrane conductance Regulator (CFTR) pre-mRNA, and methods of using same, such as for suppressing the inclusion of a cryptic exon between exon 22 and 23 as a result of the mutation 3849+10Kb C-to-T, and for treating Cystic Fibrosis (CF).

BACKGROUND

Cystic fibrosis (CF) is a common, severe autosomal recessive disease caused by mutations in the CFTR gene. The CFTR gene encodes for a chloride channel responsible for chloride transport in epithelial cells. The major manifestations of CF are in the lungs, with more than 90% mortality related to the respiratory disease. The disease in the respiratory tract is linked to the insufficient CFTR function in the airway epithelium.

As of today, approximately 2000 different mutations disrupting the CFTR functions have been identified worldwide, grouped into five distinct classes based on their effect on the CFTR function. Class I includes mutations that lead to non-functional CFTR (large deletions and stop codon mutations). Class II mutations (including the common ΔF508) lead to aberrantly folded CFTR protein that is recognized by the cell quality control mechanism and subsequently degraded, resulting in the absence of mature CFTR protein at the apical cell membrane. Class III mutations lead to full-length CFTR protein being incorporated into the cell membrane, but with defective regulation so that no CFTR function is present. These three classes usually lead to a classic CF phenotype with pancreatic insufficiency, although the severity of lung disease is highly variable. CFTR mutations leading to defective chloride conductance are grouped into Class IV. Class V mutations involve transcription dysregulation, resulting in a decreased amount of otherwise normal CFTR. The latter two classes are often associated with a milder phenotype and pancreatic sufficiency. Specifically, CFTR that results from a class IV mutation inserts into the plasma membrane but exhibits reduced single-channel chloride ion conductance because of reduced chloride permeation and open channel probability. Found in <1% of patients with CF, class V mutations produce normal plasma membrane CFTR. The quantity, however, is generally reduced as a result of transcriptional dysregulation. Class V mutations are frequently influence by the splicing machinery and generate both aberrantly and correctly spliced mRNA, the levels of which vary among different patients and even among different organs of the same patients. Ultimately, the splice variants result in a reduced number of functioning CFTR in the plasma membrane.

About 10-15% of CFTR mutations affect the correct splicing of the gene transcripts. Among these is the splicing mutation 3849+10 kb C-to-T which leads to inclusion of an 84 base pair cryptic exon in the mature messenger RNA (mRNA) (denoted "intron 22 cryptic exon inclusion" mutation). This mutation is the 12th most common CFTR mutation in the world, which occurs in hundreds of CF patients worldwide (Kerem et al., 1997). Correction of the aberrant splicing of the CFTR gene by "anti-sense" oligonucleotides (AOs) was attempted by Friedman ct al, 1999 and recently described in international PCT Application Publication WO 2014/045283 to the present inventors.

Anti-sense oligonucleotides (AOs or ASOs) administration is one of the most promising therapeutic approaches for the treatment of genetic disorders caused by splicing mutations. AOs are short synthetic molecules which can anneal to motifs predicted to be involved in the pre-mRNA splicing. The method is based on splice-switching. The AOs binding to selected sites is expected to mask the targeted region and promote normal splicing. AOs are highly specific for their targets and do not affect any other sequences in the cells. Several types of chemically modified AO molecules commonly used including: 2'-O-methyl-phosphorothioate (2'OMP), phosphorodiamidate morpholino oligomer (PMO), peptide nucleic acids (PNAs), 2-methoxyethyl phosphorothioate (MOE), constrained ethyl (cET), LIgand-Conjugated Antisense (LICA) and alternating locked nucleic acids (LNAs).

The AOs modifications maintain their stabilization, improve their target affinity, and provide favorable pharmacokinetic properties and biological stability. It has been conclusively shown that splice-switching AOs can redirect dystrophin pre-mRNA processing in murine models for Duchenne Muscular Dystrophy (DMD) so that an exon carrying a premature protein termination signal (nonsense mutation) can be excluded from the mature gene transcript resulting in a shorter but still functional dystrophin isoform. Progress in dystrophin exon skipping has been rapid, with proof-of-concept studies being reported, and with the publication of results from systemic administration to patients in both 2OMP and PMO chemistries. In 2016, the FDA granted accelerated approval to first drug for Duchenne muscular dystrophy (eteplirsen), which is a PMO AO for exon 51 skipping.

In addition to induced exon skipping, AOs can be designed to mask splice-silencing elements that reduce exon recognition and subsequent inclusion in the mature mRNA. Spinal Muscular Atrophy (SMA) is a common autosomal recessive condition caused by the loss of the SMN1 gene together with a C>T variation in SMN2 exon 7, leading to abnormal splicing in which SMN2 exon 7 is skipped, resulting in a non-functional gene product. AOs have been designed to mask nearby flanking SMN2 splice silencer elements to promote synthesis of full-length transcripts. An intrathecally administration of morpholino oligomer to neonatal mouse pups with severe SMA was highly successful, significantly extending their survival.

This led to the development of an AO-based drug, Spinraza (Nusinersen), that was recently approved by the US Food and Drug Administration (FDA) and the European Medicines Agency (EMA). The approval followed a very successful completion of a phase-III clinical trial in patients with infantile-onset SMA. The treated infants experienced a statistically significant improvement in the achievement of motor milestones. The results of this study demonstrate the great potential of AO-based splicing modulation for the treatment of genetic diseases and emphasize the importance of local delivery for efficient treatment with minimal toxicity.

There remains a constant need in the field of Cystic Fibrosis management for novel, potent therapeutics, designed to overcome the numerous mutations in the CFTR gene identified thus far, and restore CFTR function.

SUMMARY

The present invention provides compositions comprising oligonucleotides capable of binding to a CFTR pre-mRNA, thereby modulating splicing and restoring or enhancing the function of the CFTR gene product. The present invention thus identifies sequences within the CFTR pre-mRNA which are targeted in order to modulate the splicing cascade of the CFTR pre-mRNA. Modulating CFTR pre-mRNA splicing, as demonstrated in the present invention, can avoid improper recognition of intron sequences as exons. As a result of the modulation of splicing, a functional CFTR protein is produced in sufficient levels by an otherwise aberrant CFTR allele. The present invention, in some embodiments thereof, further provides modified oligonucleotides for modulating splicing and restoring or enhancing the function of the CFTR gene product.

The present invention is based, in part, on the finding that artificial "anti-sense" oligonucleotide molecules are able to target and bind predetermined sequences at the pre-mRNA molecule of the CFTR gene, and that the binding can modulate the splicing of the pre-mRNA molecule into a mature mRNA which is subsequently translated into a functional CFTR protein in sufficient levels. The targets within a CFTR pre-mRNA molecule are those discovered to be involved in splicing, either indirectly, by affecting the splicing of adjacent as well as more remote sequences, or directly, by affecting their own splicing.

Advantageously, the present invention provides anti-sense oligonucleotide molecules with improved efficacy. The oligonucleotides are highly effective in raising the percentage of correctly spliced CFTR mRNA. The oligonucleotides are short, having no more than 21 nucleotides, having advantages such as improved cell/tissue penetrating capacity.

According to a first aspect, there is provided a synthetic oligonucleotide molecule consisting of 17-21 consecutive bases having at least 80% complementarity to a pre-mRNA transcript of a CFTR gene having a 3849+10Kb C-to-T mutation, and characterized by at least partly suppressing the inclusion of intron 22 cryptic exon in the mature CFTR mRNA, increasing the percentage of correctly spliced mature CFTR mRNA by at least about 10%; and decreasing the level of aberrantly spliced mature CFTR mRNA by at least about 20%.

According to another aspect, there is provided a pharmaceutical composition comprising the synthetic oligonucleotide molecule of the invention, and a pharmaceutically acceptable carrier.

According to another aspect, there is provided a method for treating CF in a subject in need thereof, comprising administering to the subject a therapeutically effective amount of a synthetic oligonucleotide, wherein the synthetic oligonucleotide suppresses the inclusion of intron 22 cryptic exon in the mature CFTR mRNA, increases the percentage of correctly spliced mature CFTR mRNA by at least about 10%; and decreases the level of aberrantly spliced mature CFTR mRNA by at least about 20%, thereby treating CF in the subject.

According to another aspect, there is provided a kit comprising: (a) at least one synthetic oligonucleotide molecule; and at least one of: (b) at least one CFTR modifier; or (c) at least one CF drug, wherein the synthetic oligonucleotide is selected from the group consisting of SEQ ID NOs: 1-25, and 41-44, and wherein the CFTR modifier is selected from the group consisting of: CFTR potentiator, CFTR corrector, Translational Read-Through agent, and CFTR amplifier.

In some embodiments, the synthetic oligonucleotide molecule has at least 80% complementarity to a nucleotide sequence within SEQ ID NO: 37.

In some embodiments, the synthetic oligonucleotide molecule has 100% complementarity to a nucleotide sequence within SEQ ID NO: 37.

In some embodiments, the synthetic oligonucleotide molecule consists of 19 consecutive nucleotide bases.

In some embodiments, the synthetic oligonucleotide molecule consists of 18 consecutive nucleotide bases.

In some embodiments, the synthetic oligonucleotide molecule comprises a chemically modified backbone comprising: a phosphate-ribose backbone, a phosphate-deoxyribose backbone, a 2'-O-methyl-phosphorothioate backbone, a phosphorodiamidate morpholino backbone, a peptide nucleic acid backbone, a 2-methoxyethyl phosphorothioate backbone, an alternating locked nucleic acid backbone, constrained ethyl backbone, a phosphorothioate backbone, N3'-P5' phosphoroamidates, 2'-deoxy-2'-fluoro-β-d-arabino nucleic acid, cyclohexene nucleic acid backbone, tricyclo-DNA (tcDNA) nucleic acid backbone, and a combination thereof.

In some embodiments, the synthetic oligonucleotide molecule comprises a backbone comprising a 2'-O-Methyl phosphorothioate (2'OMP) modification or a 2'-Methoxy Ethyl (2'MOE) modification.

In some embodiments, the synthetic oligonucleotide molecule comprises a nucleotide sequence set forth in one of SEQ ID NOs: 1-25, and 41-44.

In some embodiments, the synthetic oligonucleotide molecule comprises a nucleotide sequence set forth in one of SEQ ID NOs: 1-5, and 41.

In some embodiments, the synthetic oligonucleotide molecule comprises the sequence GAUGGAAGA (SEQ ID NO: 38).

In some embodiments, the pharmaceutical composition is formulated for oral, nasal, inhalation, abdominal, subcutaneous, intra-peritoneal or intravenous administration.

In some embodiments, the pharmaceutical composition is for use in the treatment of cystic fibrosis (CF), in a subject in need thereof.

In some embodiments, the method further comprising administering to the subject a therapeutically effective amount of one or more CFTR modifiers.

In some embodiments, the CFTR modifier is selected from the group consisting of: a CFTR-splicing-modulating agent, Translational Read-Through agent, a CFTR amplifier, a CFTR potentiator, and a CFTR corrector.

In some embodiments, the CFTR modifier is selected from the group consisting of: a different synthetic oligonucleotide molecule capable of suppressing intron 22 cryptic exon inclusion in the mature CFTR mRNA, Ataluren, ELX-02, ivacaftor, QBW251, PTI-808, VX-561, lumacaftor, tezacaftor, elexacaftor, VX-659, VX-445, VX-152 and VX-440, GLPG2222, FDL169, PTI-801, and any combination thereof.

In some embodiments, the CFTR modifier is ivacaftor, lumacaftor, tezacaftor, elexacaftor, VX-659, VX-152, or VX-440, or any combination thereof.

In some embodiments, the subject comprises a 3849+10Kb C-to-T mutation in the CFTR gene.

In some embodiments, the subject is heterozygous to the 3849+10Kb C-to-T mutation.

In some embodiments, treating comprises improving at least one clinical parameter of CF selected from the group consisting of: lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms.

In some embodiments, the CF drug is an antibiotic drug, a bronchodilator, a corticosteroid, or any combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The M3A7 antibody recognizes the C terminal of the protein allowing identification of only full length CFTR proteins.

Figures 8A, 8B:
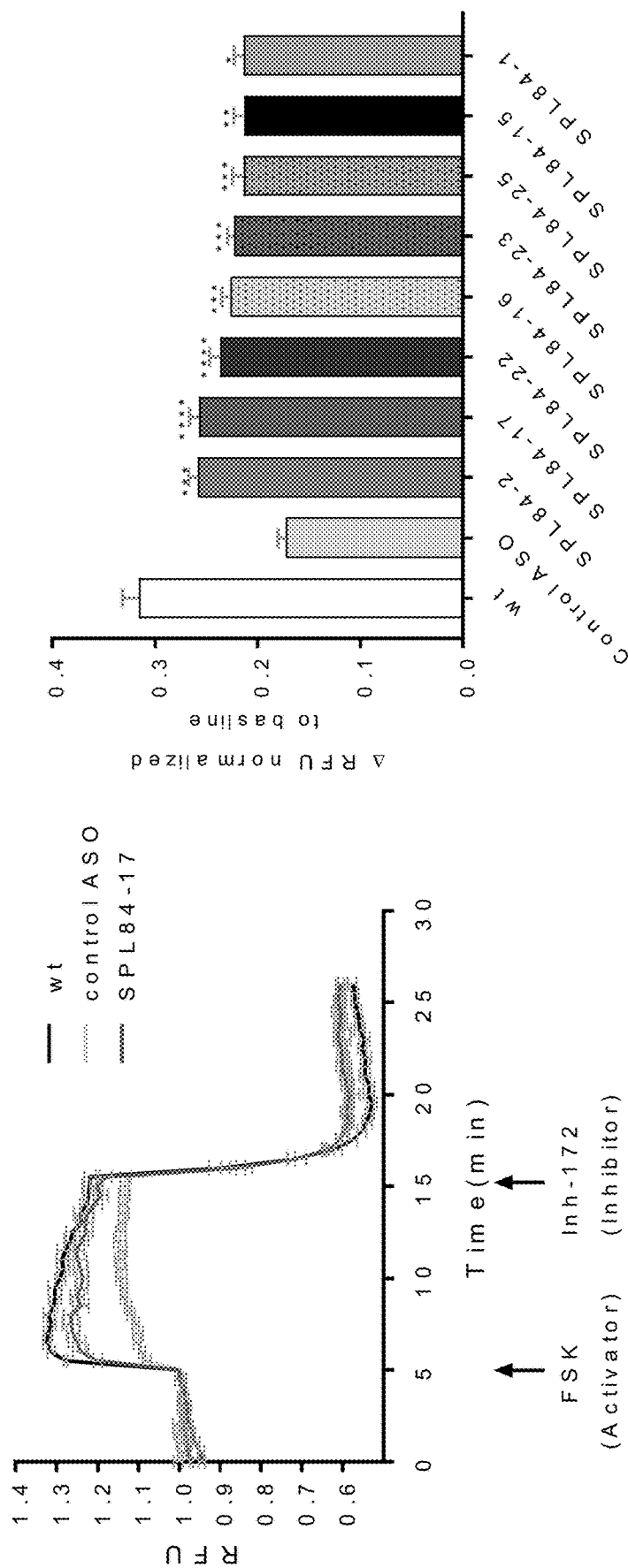

FIG. 8A is a graph showing a representative Fluorescent Imaging Plate Reader (FLIPR) trace demonstrating CFTR activation induced by the effect of ASO SPL84-17 in FRT 3849 mut cells over time (minutes). The wt trace shows the highest level of R. F. U. at between 5 and 15 minutes, wherein the SPL84-17 trace (grey center trace) nearly reaches this level of R.F. U., and the control ASO shows the lowest level of R. F. U. at the 5-15-minute time span. Between 20-25 minutes, control ASO and SPL84-17 show the same measure of R.F. U. (upper trace) while the wt is the lower trace during the 20-25 minute timespan.

FIG. 8B is a vertical bar graph showing the average effect of certain ASOs on CFTR function. The activity of the CFTR channel was analyzed using the FLIPR assay in FRT 3849 mut cells following transfection with the indicated ASO (10 nM). mean±s.e.m.

Figure 9A:
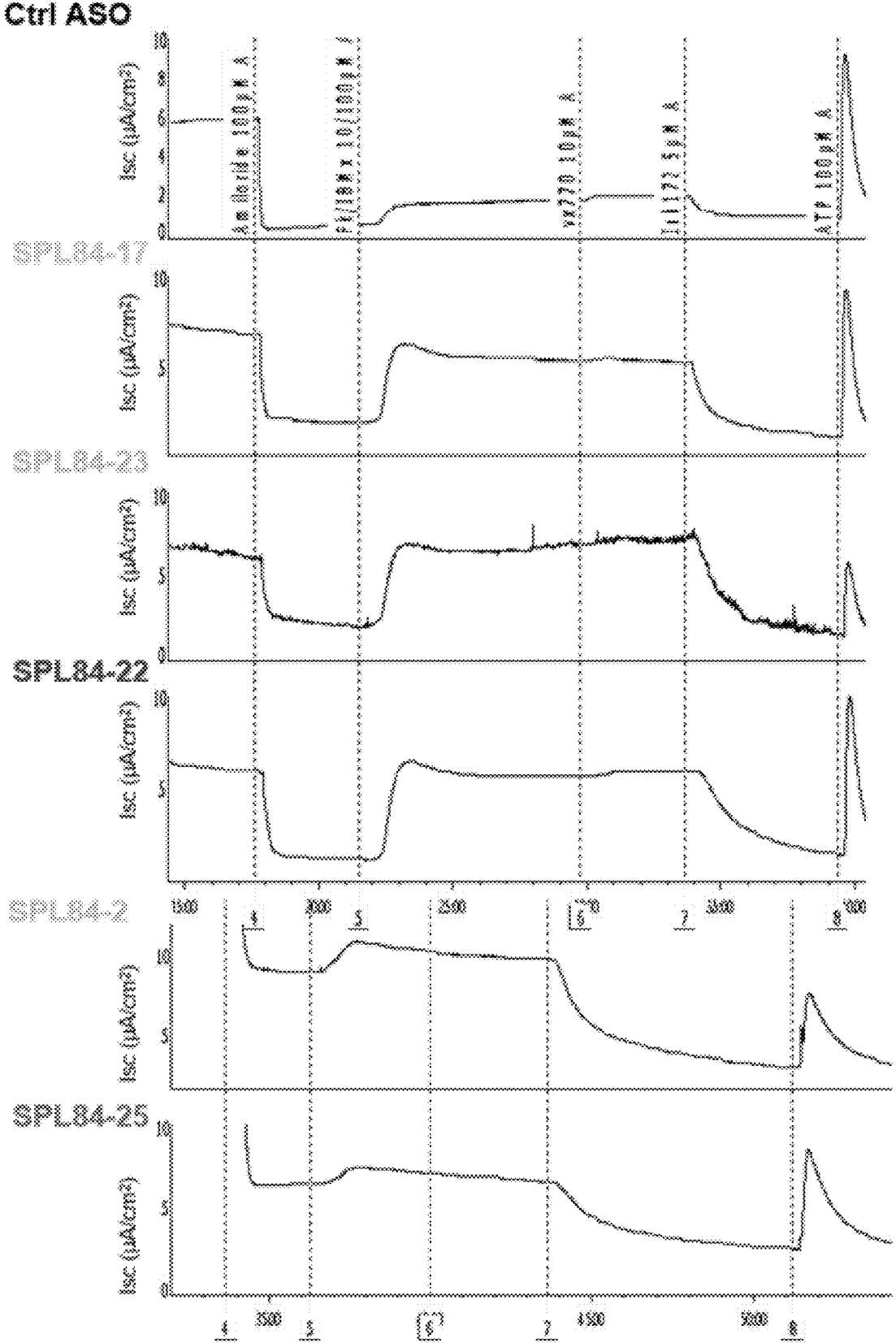

FIG. 9A includes curves showing the effect of ASOs on CFTR activation in primary Human Nasal Epithelial (HNE) cells from the heterozygous CF patient with the genotype 3849+10Kb C-to-T/F508del. Representative traces of electrophysiological responses in Ussing chamber following free uptake of the indicated ASO.

Figure 9B:
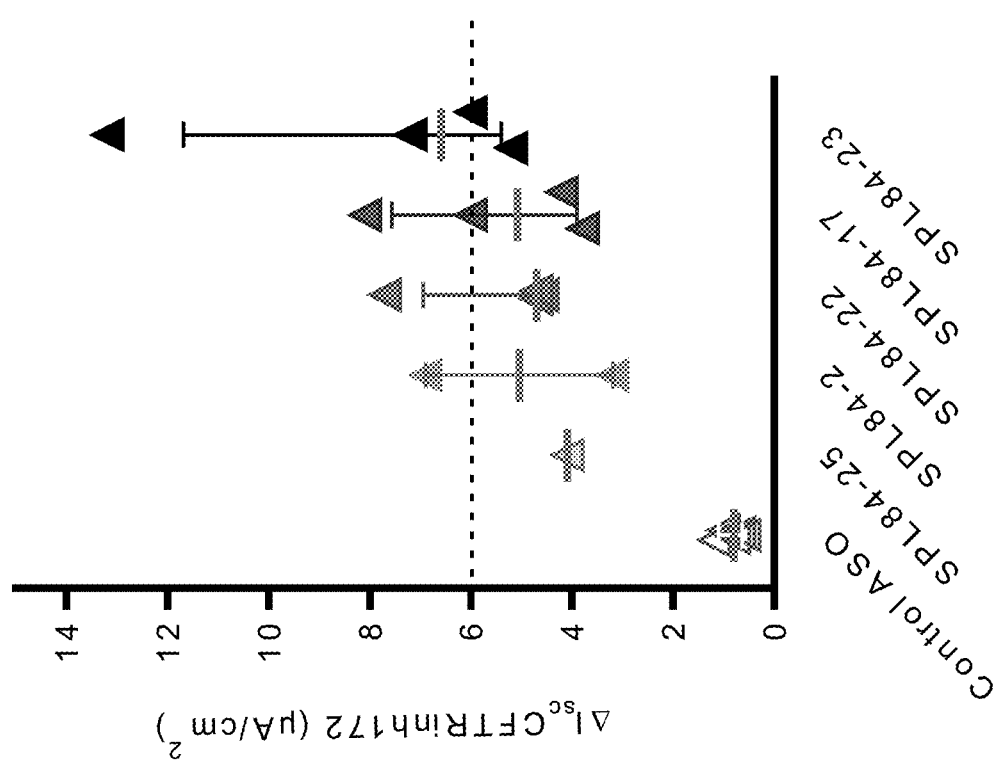

FIG. 9B is a scatter dot plot of absolute values of $\Delta I_{SC}$CFTRinh172 ($\mu$A/cm$^2$) from Ussing chamber following free uptake of the indicated ASO in the same HNE cells as in FIG. 9A. The grey thick horizontal line is marking the median. $\Delta I_{SC}$CFTRinh172 was calculated for: 4 filters treated with SPL84-22, SPL84-23 and SPL84-17 derived from 2 samples obtained from the patient, 2 filters treated with SPL84-2 and one filter treated with SPL84-25 (marked with *). The horizontal dashed line indicates 50% of the level of mean $\Delta I_{SC}$CFTRinh172 in HNE cultures from healthy WT/WT individuals.

FIG. 10A includes curves showing the effect of ASO on CFTR activation in primary HNE cells from a patient homozygote for the 3849+10Kb C-to-T mutation. Representative traces of electrophysiological responses in Ussing chamber following treatment with the indicated ASOs.

Figure 10:
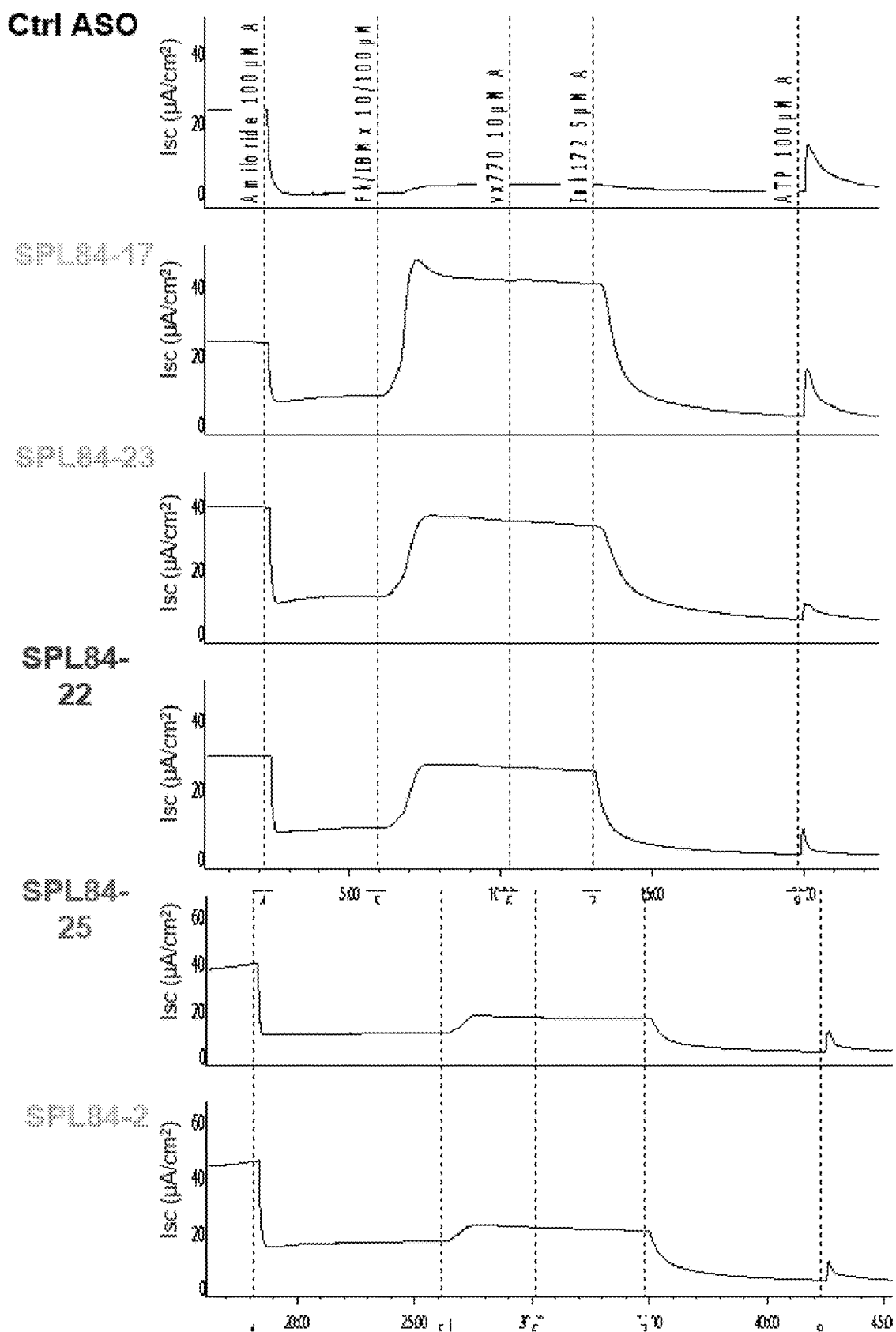
Figure 10B:
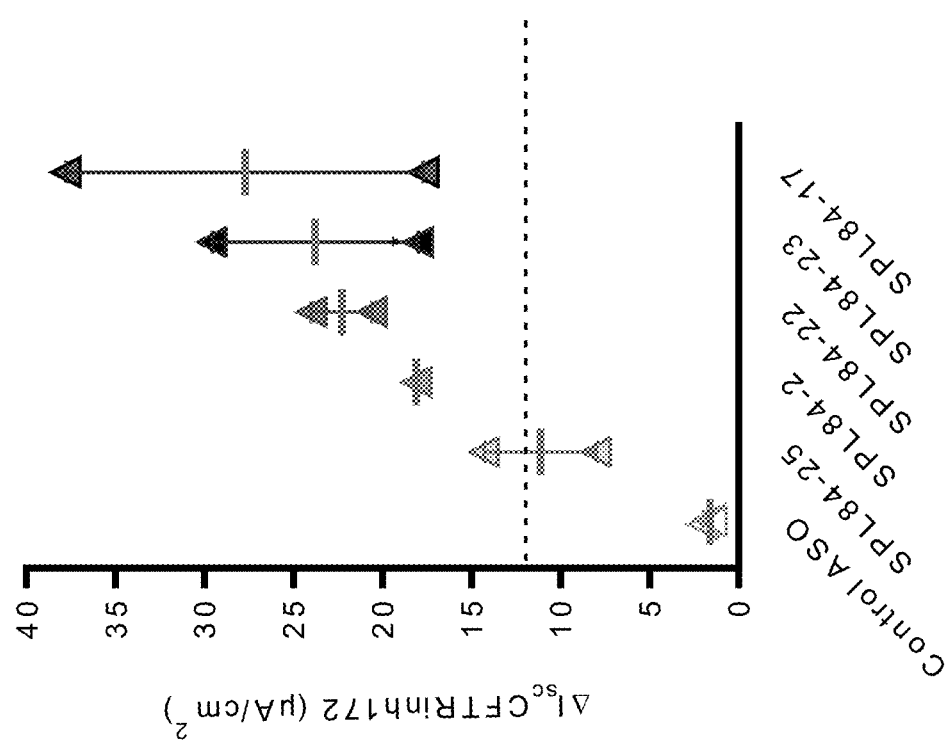

FIG. 10B is a scatter dot plot of absolute values of $\Delta I_{SC}$CFTRinh172 ($\mu$A/cm$^2$) from Ussing chamber following free uptake of the indicated ASO in the same HNE cells as in FIG. 10A. The grey thick horizontal line is marking the median. $\Delta I_{SC}$CFTRinh172 was calculated for: 2 filters, except for one filter treated with SPL84-2 (marked with *). The horizontal dashed line indicates the level of mean $\Delta I_{SC}$CFTRinh172 in HNE cultures from healthy WT/WT individuals.

Figure 11:
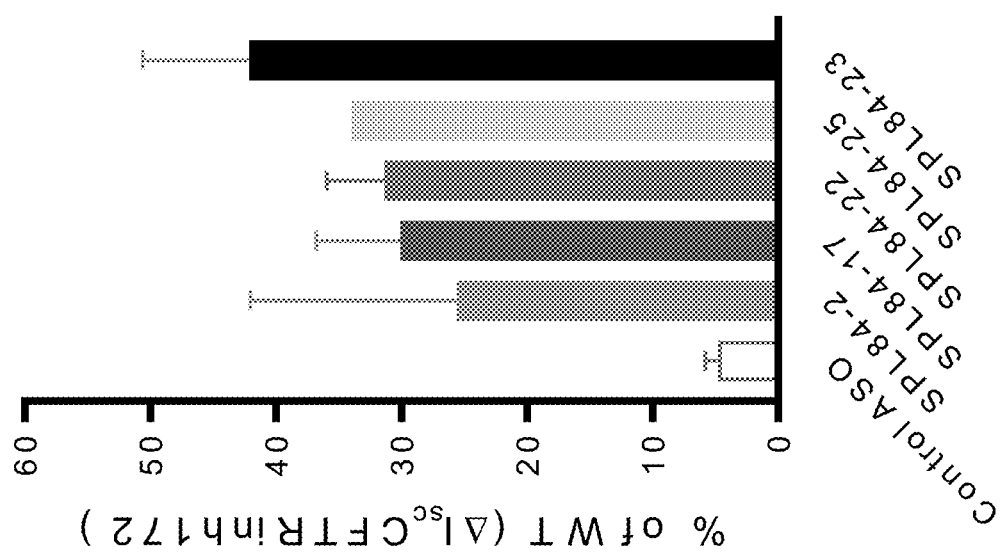

FIG. 11 is a vertical bar graph showing the summary of activation of CFTR in heterozygote patients. Mean (±SEM) values of % of WT ($\Delta I_{SC}$CFTRinh172-Patient*100/Average$\Delta I_{SC}$CFTRinh172-WT) were calculated from median values of $\Delta I_{SC}$CFTRinh172 per patient. The level of WT was set according to the mean $\Delta I_{SC}$FSK/I in HNE cultures from healthy WT/WT individuals. The values are calculated from 9 filters treated with SPL84-17 and SPL84-22 derived from 3 patients, 24 filters treated with SPL84-23 derived from 5 patients, 5 filters treated with SPL84-2 derived from 2 patients and 1 filter treated with SPL84-25 derived from 1 patient.

Figure 12A:
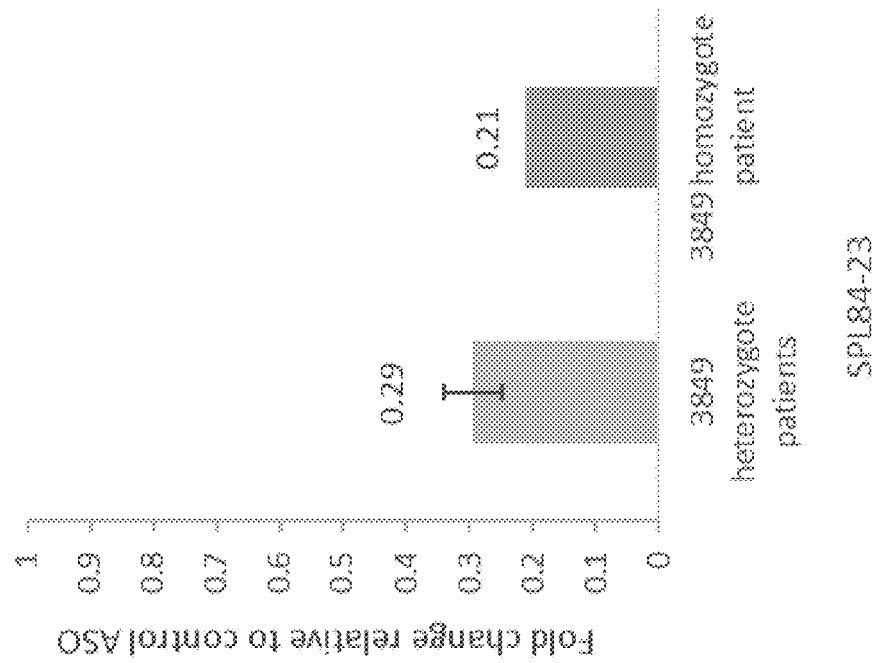
Figure 12B:
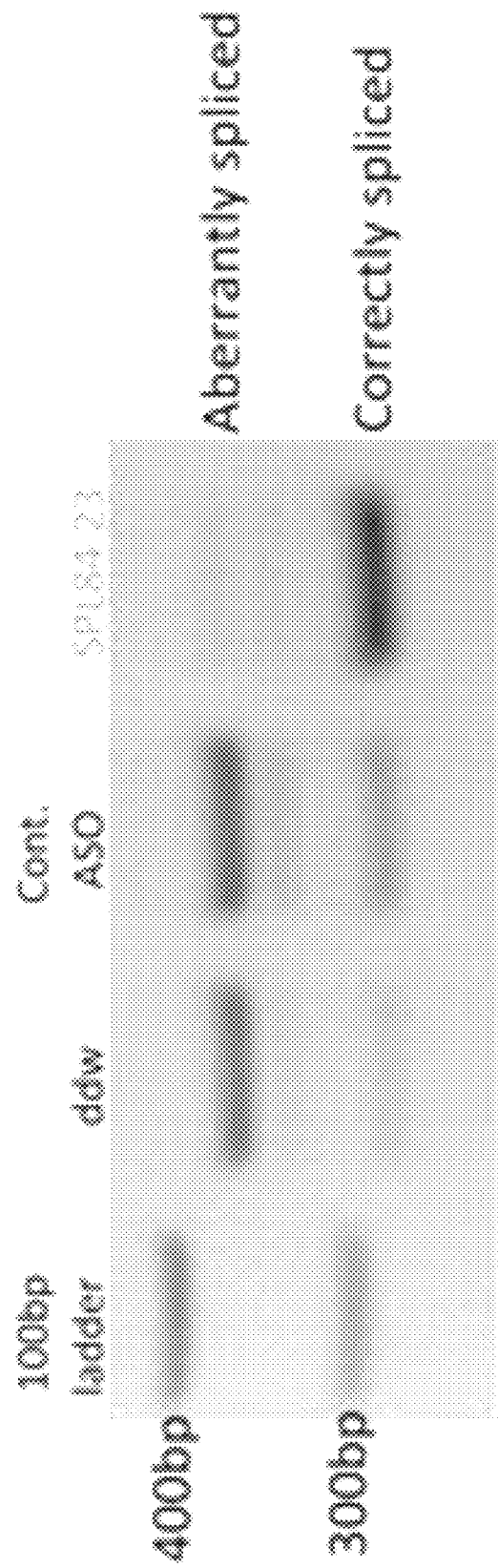

FIGS. 12A-12B include a vertical bar graph and a micrograph of gel electrophoresis showing the effect of ASO SPL84-23 on the splicing pattern of 3849+10 kb C>T mutation. HNE cells from patients homozygous (N=1) or heterozygous (N=4) for the 3849+10 kb C-to-T mutation were treated with 200 nM SPL84-23. RNA was extracted and the levels of aberrantly and correctly spliced CFTR transcripts were measured. FIG. 12A shows qRT-PCR analysis for the effect of SPL84-23 on aberrantly spliced CFTR transcripts. The values shown are the average fold change (mean±SEM) relative to cells treated with control ASO. Values were normalized against transcripts of GUSb gene. Statistical analysis was performed using student's t-test (1 tail, paired). *** p<0.001. FIG. 12B shows RT-PCR on the homozygous samples in agarose gels.

Figure 13:
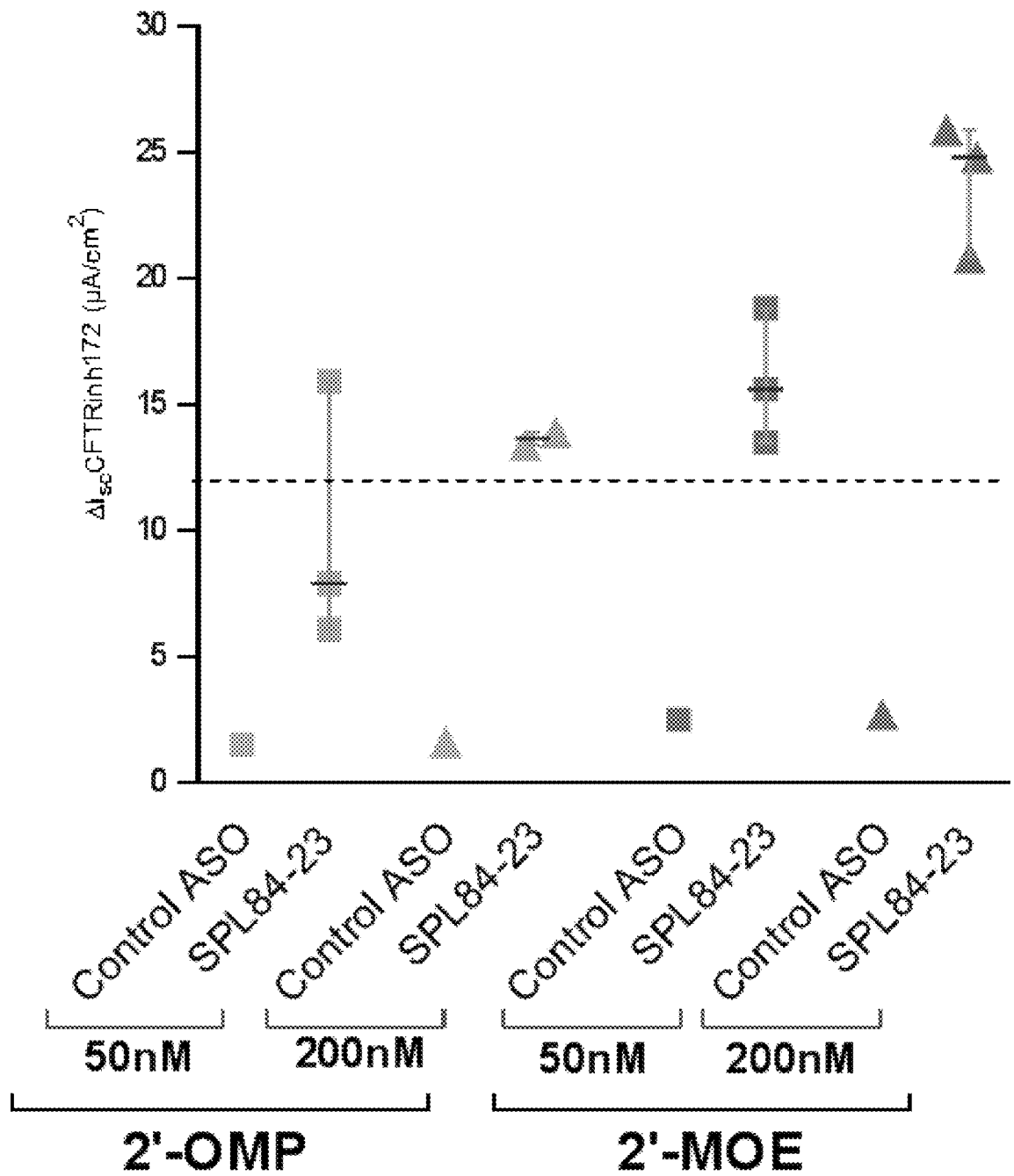

FIG. 13 is a graph showing the effect of chemical modifications on ASO SPL84-23 on the splicing pattern of 3849+10 kb C>T mutation. Scatter dot plot of absolute values of $\Delta I_{SC}$CFTRinh172 ($\mu$A/cm$^2$). The horizontal lines mark the median value for each group. $\Delta I_{SC}$CFTRinh172 was calculated for cells treated with the indicated concentrations of ASO modified with the 2'OMP or 2'MOE. The horizontal dashed line indicates the level of mean $\Delta I_{SC}$CFTRinh172 in HNE cultures sampled from healthy WT/WT individuals.

Figure 14:
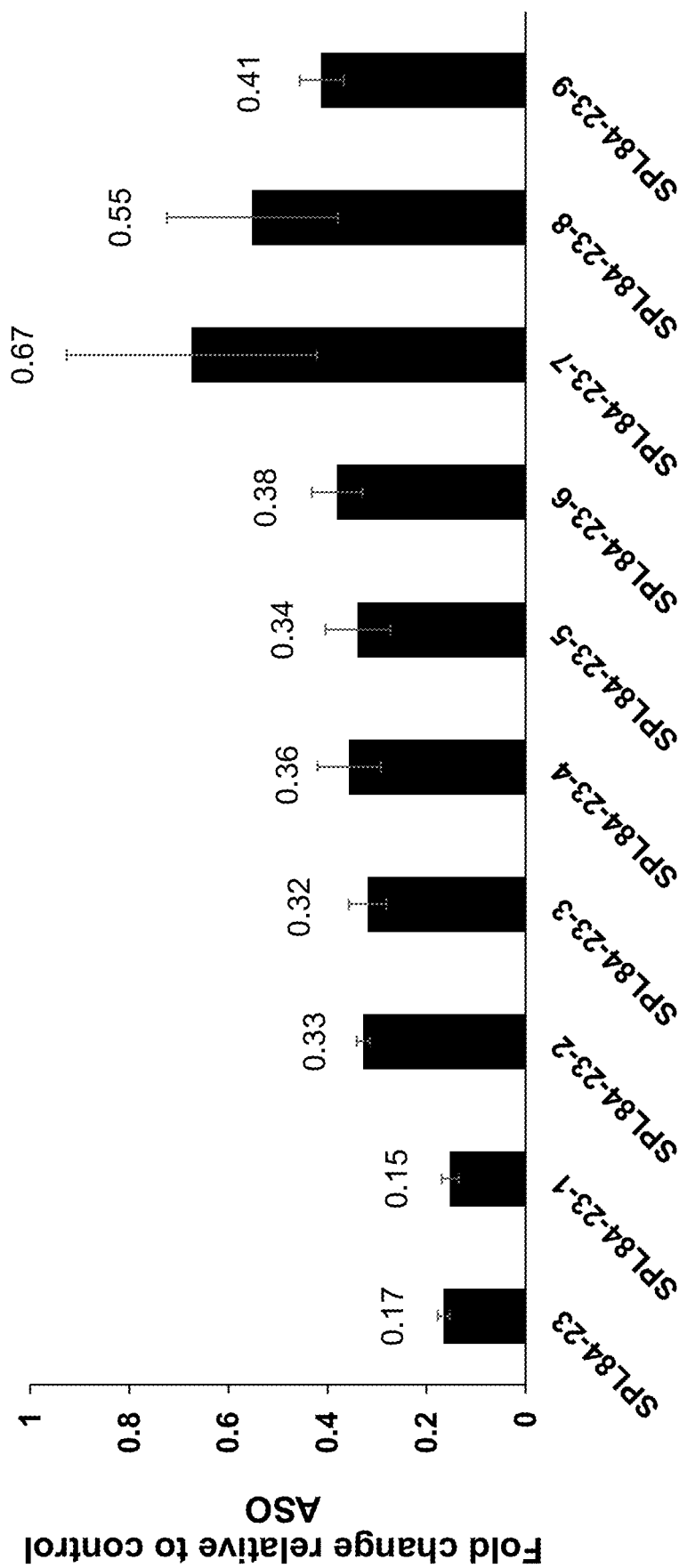

FIG. 14 is a vertical bar graph showing optimization of the ASO length on aberrantly spliced variants of CFTR transcripts. Short versions of ASO84-23 were screened for their effect on splicing by free uptake on primary patient HNE cells (SPL84-23-1-SPL84-23-9). On average in the three 3849 heterozygote patients analyzed, the effect of SPL84-23-1 (19 mer) was comparable to SPL84-23.

Figure 15B:
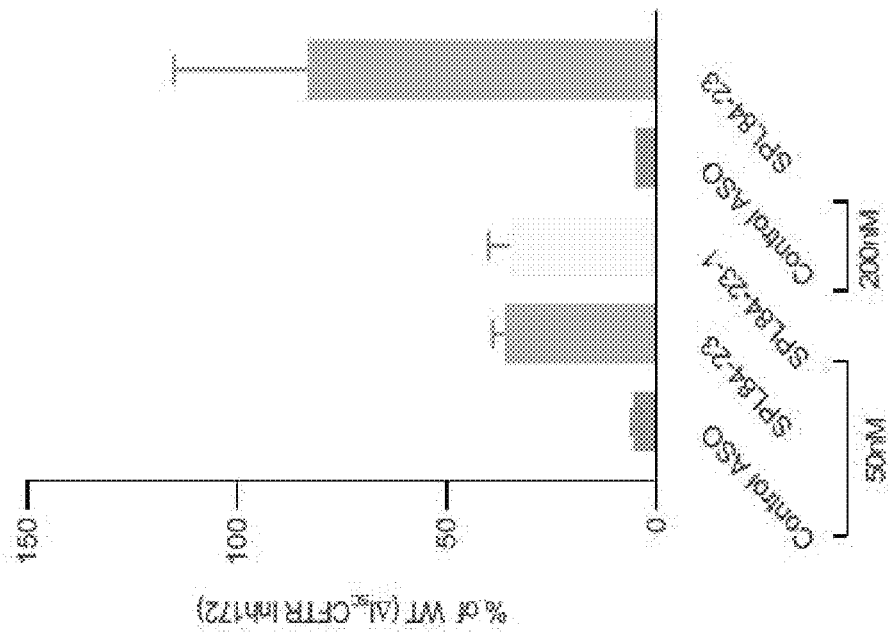
Figure 15A:
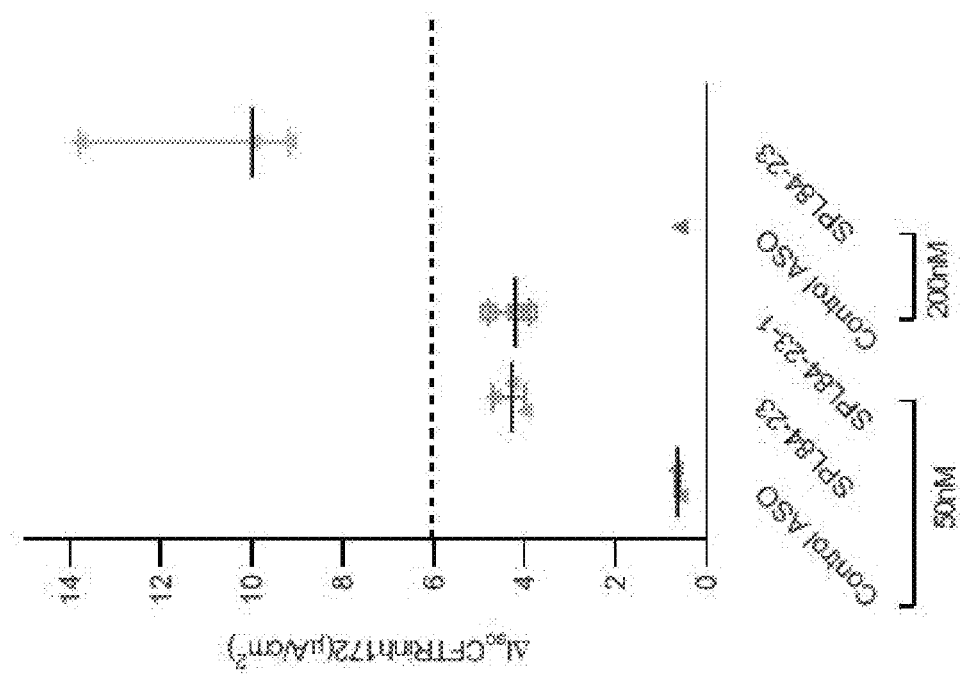

FIGS. 15A-15B are graphs showing optimization of the ASO length. Primary HNE cells were obtained from a heterozygous patient (3849/F508del). SPL84-23-1 (19 mer) has a similar effect on the CFTR function as the longer SPL84-23 ASO in primary HNE cells. (15A) represents absolute values of $\Delta I_{SC}$CFTRinh172 ($\mu$A/cm$^2$), and (15B) represents the ratio compared to the WT (% of WT ($I_{SC}$CFTRinh172)). The horizontal dashed line in FIG. 15A indicates 50% of the level of mean $\Delta I_{SC}$CFTRinh172 in HNE cultures from healthy WT/WT individuals, where 50% of WT levels in 3849/F508del HBE cells represent fully restored activity in the 3849 allele. The short, solid horizontal lines mark the median value for each group.

Figures 16A, 16B:
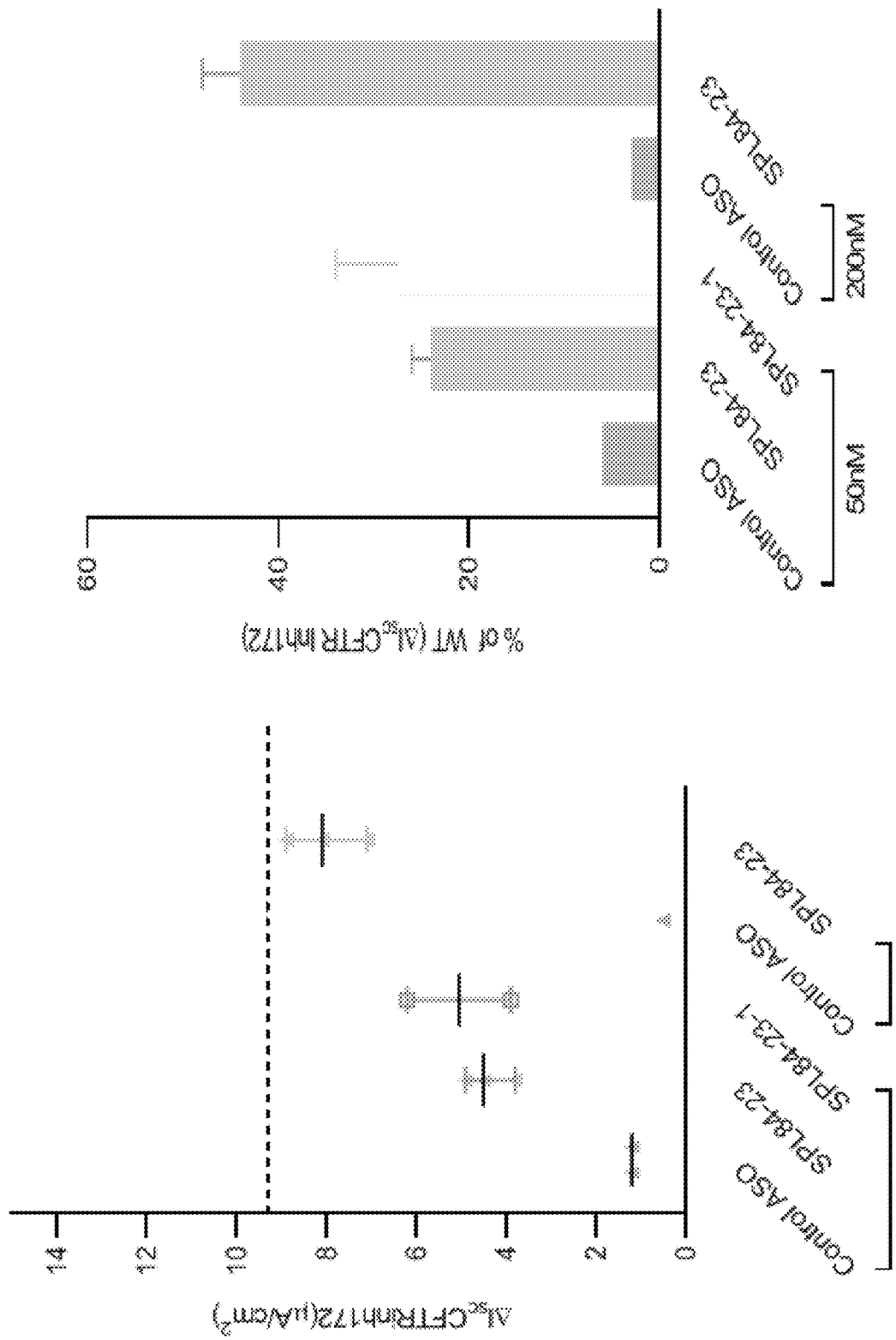

FIGS. 16A-16B are graphs showing optimization of the ASO length. Primary HBE cells were obtained from a heterozygous patient (3849/F508del). SPL84-23-1 (19 mer) has a similar effect on the CFTR function as the longer SPL84-23 ASO in primary HNE cells. (16A) represents absolute values of $\Delta I_{SC}$CFTRinh172 ($\mu$A/cm$^2$), and (16B) represents the ratio compared to the WT (% of WT ($I_{SC}$CFTRinh172)). The horizontal dashed line in FIG. 16A indicates 50% of the level of mean $\Delta I_{SC}$CFTRinh172 in HBE cultures from healthy WT/WT individuals, where 50% of WT levels in 3849/F508del HBE cells represent fully restored activity in the 3849 allele. The short, solid horizontal lines mark the median value for each group.

DETAILED DESCRIPTION

In some embodiments, there is provided a synthetic oligonucleotide molecule consisting of 18-21 consecutive bases having at least 80% complementarity to a pre-mRNA transcript of a CFTR gene having a 3849+10Kb C-to-T mutation, and characterized by at least partly suppressing the inclusion of intron 22 cryptic exon in the mature CFTR mRNA, increasing the percentage of correctly spliced mature CFTR mRNA by at least about 10%; and decreasing the level of aberrantly spliced mature CFTR mRNA by at least about 20%.

In some embodiments, there is provided a method for treating CF in a subject in need thereof, comprising administering to the subject a therapeutically effective amount of the synthetic oligonucleotide of the invention, thereby treating CF in the subject.

In some embodiments, the treating comprises: suppressing the inclusion of intron 22 cryptic exon in the mature CFTR mRNA, increasing the percentage of correctly spliced mature CFTR mRNA by at least about 10%, decreasing the level of aberrantly spliced mature CFTR mRNA by at least about 20%, or any combination thereof.

The present invention provides oligonucleotides and compositions comprising same, capable of binding to a CFTR pre-mRNA, thereby modulating splicing and restoring the function of the CFTR gene product. The present invention thus identifies sequences within the CFTR pre-mRNA which are targeted in order to modulate the splicing cascade of the CFTR pre-mRNA. Modulating CFTR pre-mRNA splicing, as demonstrated in the present invention, can avoid improper recognition of intron sequences as exons. As a result of the modulation of splicing, a functional CFTR protein is produced by an otherwise aberrant CFTR allele.

In some embodiments, the herein disclosed oligonucleotide is a synthetic oligonucleotide.

The present invention stems in part from the finding that artificial "anti-sense" polynucleotide molecules are able to target and bind predetermined sequences at the pre-mRNA molecule of the CFTR gene, and that the binding modulates the splicing of the pre-mRNA molecule into mature mRNA, which subsequently translates into a functional CFTR protein. The targets within a CFTR pre-mRNA molecule are those discovered to be involved in splicing, either indirectly, by affecting the splicing of adjacent as well as remote sequences, or directly, by affecting their own splicing.

The present invention provides, in one aspect, a synthetic oligonucleotide molecule, consisting of 17-21 consecutive bases that are complementary to a pre-mRNA transcript of a CFTR gene, wherein the synthetic oligonucleotide molecule at least partly suppresses the inclusion of intron 22 cryptic exon in the mature CFTR mRNA, increases the percentage of correctly spliced mature CFTR mRNA by at least about 10%; and decreases the level of aberrantly spliced mature CFTR mRNA by at least about 20%.

In another aspect, the present invention provides a synthetic oligonucleotide molecule consisting of 17-21 consecutive bases that are complementary to a pre-mRNA transcript of a CFTR gene having a 3849+10Kb C-to-T mutation, wherein the synthetic oligonucleotide molecule at least partly suppresses the inclusion of intron 22 cryptic exon in the mature CFTR mRNA, decreases the level of aberrantly spliced mature CFTR mRNA by at least about 20%.

In some embodiments, the oligonucleotide increases the percentage of correctly spliced mature CFTR mRNA by at least about 12%. In some embodiments, the oligonucleotide increases the percentage of correctly spliced mature CFTR mRNA by at least about 10%.

The present invention provides, in additional aspect, a synthetic oligonucleotide molecule, consisting of 17-21 consecutive bases that are complementary to a pre-mRNA transcript of a CFTR gene having a 3849+10Kb C-to-T mutation, wherein the synthetic oligonucleotide molecule at least partly suppresses the inclusion of intron 22 cryptic exon in the mature CFTR mRNA, increases the percentage of correctly spliced mature CFTR mRNA by at least about 10%; and decreases the level of aberrantly spliced mature CFTR mRNA by at least about 20%, wherein the oligonucleotide comprises a 2'-O-methyl-phosphorothioate backbone and/or 2'-Methoxy Ethyl (2'MOE) backbone. The phrase "suppress intron 22 cryptic exon inclusion" as used herein refers to lowering the occurrence of the addition of 84 nucleotides (SEQ ID NO: 35) found within intron 22 of the CFTR gene to the mature CFTR mRNA.

The phrase "the percentage of correctly spliced mature CFTR mRNA" as used herein refers to the percentage of correctly spliced mature CFTR mRNA compared to the 100% of correctly spliced mature CFTR mRNA found in a healthy cell or subject not having a mutation in either allele of the CFTR gene. For example, an increase from 1% before treatment by the ASOs provided by the present invention to 11% after the treatment by the ASOs provided by the present invention is considered an increase of 10%. An increase from 10% before treatment by the ASOs provided by the present invention to 11% after the treatment by the ASOs provided by the present invention is considered an increase of 1%.

In certain embodiments, the CFTR transcript comprises a mutation that increases inclusion of an intron 22 cryptic exon. In certain embodiments, the mutation is a 3849+10Kb C to T mutation. In some embodiments, the intron 22 cryptic exon comprises the sequence of SEQ ID NO: 35 or a fragment thereof.

In certain embodiments, the oligonucleotide molecule is complementary to a nucleotide sequence within SEQ ID NO: 37. In some embodiments, the oligonucleotide molecule is complementary to a nucleotide sequence not more than 1000, 900, 800, 700, 600, 500, 400, 300, 200 or 100 bases upstream of a mutation that increase inclusion of an intron 22 cryptic exon. Each possibility represents a separate embodiment of the invention. In some embodiments, the oligonucleotide molecule is complementary to a nucleotide sequence not more than 1000, 900, 800, 700, 600, 500, 400, 300, 200 or 100 bases downstream of a mutation that increase inclusion of an intron 22 cryptic exon. Each possibility represents a separate embodiment of the invention.

In some embodiments, the oligonucleotide has at least 75%, at least 80%, at least 85%, at least 90%, at least 95%, at least 99%, or 100% complementarity to a nucleotide sequence within SEQ ID NO: 37.

In certain embodiments, the oligonucleotide molecule is complementary to a nucleotide sequence corresponding to pre-mRNA molecule comprising a sequence about 100 base pairs before the intron 22 cryptic exon to about 100 base pairs after the intron 22 cryptic exon transcribed from a CFTR gene having a 3849+10Kb C-to-T mutation. In certain embodiments, the oligonucleotide molecule is complementary to a nucleotide sequence within SEQ ID NO: 37.

The terms "complementary" or "complementarity" refer to the ability of nucleic acids, e.g., oligonucleotide, polynucleotide, etc., to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

In certain embodiments, the oligonucleotide molecule increases the percentage of correctly spliced mature CFTR mRNA by about 20%. In certain embodiments, the oligonucleotide molecule increases the percentage of correctly spliced mature CFTR mRNA by about 30%. In certain embodiments, the oligonucleotide molecule increases the percentage of correctly spliced mature CFTR mRNA by about 40%. In certain embodiments, the oligonucleotide molecule increases the percentage of correctly spliced mature CFTR mRNA by about 50%. In certain embodiments, the oligonucleotide molecule increases the percentage of correctly spliced mature CFTR mRNA by about 60%.

The phrase "increases the level of correctly spliced mature CFTR mRNA" as used herein refers to the increase in the level of correctly spliced mature CFTR mRNA after treatment by the ASOs provided by the present invention compared to the level before treatment or after mock-treatment. In certain embodiments, the increase in the level of correctly spliced mature CFTR mRNA is compared to mock-treatment by a control ASO. In certain embodiments, the control ASO consists of the nucleotide sequence in SEQ ID NO: 33.

In certain embodiments, the oligonucleotide molecule decreases the level of aberrantly spliced mature CFTR mRNA by about 30%. In certain embodiments, the oligonucleotide molecule decreases the level of aberrantly spliced mature CFTR mRNA by about 40%. In certain embodiments, the oligonucleotide molecule decreases the level of aberrantly spliced mature CFTR mRNA by about 50%. In certain embodiments, the oligonucleotide molecule decreases the level of aberrantly spliced mature CFTR mRNA by about 60%. In certain embodiments, the oligonucleotide molecule decreases the level of aberrantly spliced mature CFTR mRNA by about 70%. In certain embodiments, the oligonucleotide molecule decreases the level of aberrantly spliced mature CFTR mRNA by about 80%.

The phrase "decreases the level of aberrantly spliced mature CFTR mRNA" as used herein refers to the percentage decrease in the level of aberrantly spliced mature CFTR mRNA after treatment by the ASOs provided by the present invention compared to the level before treatment or after mock-treatment. In certain embodiments, the decrease in the level of aberrantly spliced mature CFTR mRNA is compared to mock-treatment by a control ASO. In certain embodiments, the control ASO consists of the nucleotide sequence in SEQ ID NO: 33. The phrase "increases the percentage of correctly spliced mature CFTR mRNA" as used herein refers to the percent increase in the ratio of correctly spliced to aberrantly spliced CFTR mRNA compared to untreated or mock-treatment.

In certain embodiments, the oligonucleotide molecule consists of 18 or 19 consecutive nucleotide bases. In certain embodiments, the oligonucleotide molecule consists of 18 consecutive nucleotide bases. In certain embodiments, the oligonucleotide molecule consists of 19 consecutive nucleotide bases. In certain embodiments, the oligonucleotide molecule consists of 20 consecutive nucleotide bases. In certain embodiments, the oligonucleotide molecule consists of 21 consecutive nucleotide bases.

In certain embodiments, the base is selected from the group consisting of adenine, guanine, cytosine, uracil and optionally thymine. In other certain embodiments, the base is selected from the group consisting of adenine, guanine, cytosine, and uracil. Each possibility represents a separate embodiment of the present invention.

In some embodiments, the oligonucleotide is chemically modified. In some embodiments, the chemical modification is a modification of a backbone of the oligonucleotide. In some embodiments, the chemical modification is a modification of a sugar of the oligonucleotide. In some embodiments, the chemical modification is a modification of a nucleobase of the oligonucleotide. In some embodiments, the chemical modification increases stability of the oligonucleotide in a cell. In some embodiments, the chemical modification increases stability of the oligonucleotide in vivo. In some embodiments, the chemical modification increases the oligonucleotide's ability to modulate splicing. In some embodiments, the chemical modification increases the oligonucleotide's ability to induce suppress the inclusion of intron 22 cryptic exon. In some embodiments, the chemical modification increases the half-life of the oligonucleotide. In some embodiments, the chemical modification inhibits polymerase extension from the 3' end of the oligonucleotide. In some embodiments, the chemical modification inhibits recognition of the oligonucleotide by a polymerase. In some embodiments, the chemical modification inhibits double-strand trigged degradation. In some embodiments, the chemically modified oligonucleotide does not trigger nucleic acid double-stranded degradation upon binding a CFTR pre-mRNA. In some embodiments, the chemical modification inhibits RISC-mediated degradation. In some embodiments, the chemical modification inhibits RISC-mediated degradation or any parallel nucleic acid degradation pathway.

In some embodiments, the oligonucleotide is devoid of a labeling moiety. In some embodiments, the oligonucleotide is not labeled. In some embodiments, the oligonucleotide does not emit a detectable signal or does not comprise moieties capable of being recognized so as to enable nucleic acid detection (e.g., digoxigenin and fluorescently labeled anti-DIG antibody). In some embodiments, a detectable signal comprises a dye or an emitting energy which provides detection of a compound, e.g., a polynucleotide, in vivo, ex vivo, or in vitro. In some embodiments, a detectable signal comprises: a fluorescent signal, a chromatic signal, or a radioactive signal.

In some embodiments, the oligonucleotide is devoid of radioactive nucleobase(s); digoxigenin, streptavidin, biotin, a fluorophore, hapten label, CLICK label, amine label, or thiol label.

In certain embodiments, the consecutive nucleotide bases are linked by a backbone selected from the group consisting of a phosphate-ribose backbone, a phosphate-deoxyribose backbone, a 2'-O-methyl-phosphorothioate backbone, a phosphorodiamidate morpholino backbone, a peptide nucleic acid backbone, a 2-methoxyethyl phosphorothioate backbone, an alternating locked nucleic acid backbone, constrained ethyl backbone, and a phosphorothioate backbone. Each possibility represents a separate embodiment of the invention.

According to some embodiments, the oligonucleotide comprises a 2'-O-methyl-phosphorothioate backbone. According to other embodiments, the oligonucleotide comprises a 2'-Methoxy Ethyl (2'MOE) modification.

In some embodiments, the oligonucleotide comprises a 2'-O-methyl-phosphorothioate modification. In some embodiments, the oligonucleotide comprises a 2'MOE modification. In some embodiments, the modification is throughout the molecule. In some embodiments, the modification is at the 3' end of the molecule. In some embodiments, the modification is at the 5' end of the molecule. In some embodiments, the molecule comprises at least 1, 2, 3, 4, 5, 6, 7, 8, 9, 10, 11, 12, 13, 14, 15, 16, 17, 18, 19, 20, 21, 22, 23, 24 or 25 modifications. Each possibility represents a separate embodiment of the invention.

According to some embodiments, the oligonucleotide modification is capable of completely restoring CFTR function compared to non-mutated CFTR. According to certain embodiments, the oligonucleotide modification is capable of restoring at least 70%, 75%, 80%, 85%, 90%, or 95% of CFTR function compared to non-mutated CFTR. Each possibility represents a separate embodiment of the invention.

In certain embodiments, the oligonucleotide molecule comprises or consists of a nucleotide sequence set forth in SEQ ID NO: 1. In certain embodiments, the oligonucleotide molecule comprises or consists of a nucleotide sequence set forth in SEQ ID NO: 2. In certain embodiments, the oligonucleotide molecule comprises or consists of a nucleotide sequence set forth in SEQ ID NO: 3. In certain embodiments, the oligonucleotide molecule comprises or consists of a nucleotide sequence set forth in SEQ ID NO: 4. In certain embodiments, the oligonucleotide molecule comprises or consists of a nucleotide sequence set forth in SEQ ID NO: 5. In certain embodiments, the oligonucleotide molecule comprises or consists of a nucleotide sequence set forth in SEQ ID NO: 6. In certain embodiments, the oligonucleotide molecule comprises or consists of a nucleotide sequence set forth in SEQ ID NO: 7. In certain embodiments, the oligonucleotide molecule comprises or consists of a nucleotide sequence set forth in SEQ ID NO: 8. In certain embodiments, the oligonucleotide molecule comprises or consists of a nucleotide sequence set forth in SEQ ID NO: 9. In certain embodiments, the oligonucleotide molecule comprises or consists of a nucleotide sequence set forth in SEQ ID NO: 10. In certain embodiments, the oligonucleotide molecule comprises or consists of a nucleotide sequence set forth in SEQ ID NO: 11. In certain embodiments, the oligonucleotide molecule comprises or consists of a nucleotide sequence set forth in SEQ ID NO: 12. In certain embodiments, the oligonucleotide molecule comprises or consists of a nucleotide sequence set forth in SEQ ID NO: 13. In certain embodiments, the oligonucleotide molecule comprises or consists of a nucleotide sequence set forth in SEQ ID NO: 14. In certain embodiments, the oligonucleotide molecule comprises or consists of a nucleotide sequence set forth in SEQ ID NO: 15. In certain embodiments, the oligonucleotide molecule comprises or consists of a nucleotide sequence set forth in SEQ ID NO: 16. In certain embodiments, the oligonucleotide molecule comprises or consists of a nucleotide sequence set forth in SEQ ID NO: 17. In certain embodiments, the oligonucleotide molecule comprises or consists of a nucleotide sequence set forth in SEQ ID NO: 18. In certain embodiments, the oligonucleotide molecule comprises or consists of a nucleotide sequence set forth in SEQ ID NO: 19. In certain embodiments, the oligonucleotide molecule comprises or consists of a nucleotide sequence set forth in SEQ ID NO: 20. In certain embodiments, the oligonucleotide molecule comprises or consists of a nucleotide sequence set forth in SEQ ID NO: 21. In certain embodiments, the oligonucleotide molecule comprises or consists of a nucleotide sequence set forth in SEQ ID NO: 22. In certain embodiments, the oligonucleotide molecule comprises or consists of a nucleotide sequence set forth in SEQ ID NO: 23. In certain embodiments, the oligonucleotide molecule comprises or consists of a nucleotide sequence set forth in SEQ ID NO: 24. In certain embodiments, the oligonucleotide molecule comprises or consists of a nucleotide sequence set forth in SEQ ID NO: 25. In certain embodiments, the oligonucleotide molecule comprises or consists of a nucleotide sequence set forth in SEQ ID NO: 40. In certain embodiments, the oligonucleotide molecule comprises or consists of a nucleotide sequence set forth in SEQ ID NO: 41. In certain embodiments, the oligonucleotide molecule comprises or consists of a nucleotide sequence set forth in SEQ ID NO: 42. In certain embodiments, the oligonucleotide molecule comprises or consists of a nucleotide sequence set forth in SEQ ID NO: 43. In certain embodiments, the oligonucleotide molecule comprises or consists of a nucleotide sequence set forth in SEQ ID NO: 44. In certain embodiments, the oligonucleotide molecule comprises or consists of a nucleotide sequence set forth in SEQ ID NO: 45. In certain embodiments, the oligonucleotide molecule comprises or consists of a nucleotide sequence set forth in SEQ ID NO: 46. In certain embodiments, the oligonucleotide molecule comprises or consists of a nucleotide sequence set forth in SEQ ID NO: 47. In certain embodiments, the oligonucleotide molecule comprises or consists of a nucleotide sequence set forth in SEQ ID NO: 48. In certain embodiments, the oligonucleotide molecule comprises or consists of a nucleotide sequence set forth in SEQ ID NO: 49. In certain embodiments, the oligonucleotide molecule comprises or consists of a nucleotide sequence set forth in SEQ ID NO: 50. In certain embodiments, the oligonucleotide molecule comprises or consists of a nucleotide sequence set forth in SEQ ID NO: 51. In certain embodiments, the oligonucleotide molecule comprises or consists of a nucleotide sequence set forth in SEQ ID NO: 52. In certain embodiments, the oligonucleotide molecule comprises or consists of a nucleotide sequence set forth in SEQ ID NO: 53. In certain embodiments, the oligonucleotide molecule comprises or consists of a nucleotide sequence set forth in SEQ ID NO: 54. In certain embodiments, the oligonucleotide molecule comprises or consists of a nucleotide sequence set forth in SEQ ID NO: 55. In certain embodiments, the oligonucleotide molecule comprises or consists of a nucleotide sequence set forth in SEQ ID NO: 56. In certain embodiments, the oligonucleotide molecule comprises or consists of a nucleotide sequence set forth in SEQ ID NO: 57. In certain embodiments, the oligonucleotide molecule comprises or consists of a nucleotide sequence set forth in SEQ ID NO: 58. In certain embodiments, the oligonucleotide molecule comprises or consists of a nucleotide sequence set forth in SEQ ID NO: 59. In certain embodiments, the oligonucleotide molecule comprises or consists of a nucleotide sequence set forth in SEQ ID NO: 60. In certain embodiments, the oligonucleotide molecule comprises or consists of a nucleotide sequence set forth in SEQ ID NO: 61. In certain embodiments, the oligonucleotide molecule comprises or consists of a nucleotide sequence set forth in SEQ ID NO: 62. In certain embodiments, the oligonucleotide molecule comprises or consists of a nucleotide sequence set forth in SEQ ID NO: 63. In certain embodiments, the oligonucleotide molecule comprises or consists of a nucleotide sequence set forth in SEQ ID NO: 64. In certain embodiments, the oligonucleotide molecule comprises or consists of a nucleotide sequence set forth in SEQ ID NO: 65. In certain embodiments, the oligonucleotide molecule comprises or consists of a nucleotide sequence set forth in SEQ ID NO: 66. In certain embodiments, the oligonucleotide molecule comprises or consists of a nucleotide sequence set forth in SEQ ID NO: 67. In certain embodiments, the oligonucleotide molecule comprises or consists of a nucleotide sequence set forth in SEQ ID NO: 68. In certain embodiments, the oligonucleotide molecule comprises or consists of a nucleotide sequence set forth in SEQ ID NO: 69. In certain embodiments, the oligonucleotide molecule comprises or consists of a nucleotide sequence set forth in SEQ ID NO: 70. In certain embodiments, the oligonucleotide molecule comprises or consists of a nucleotide sequence set forth in SEQ ID NO: 71.

In certain embodiments, the oligonucleotide molecule comprises a nucleotide sequence set forth in one of SEQ ID NO: 1 to SEQ ID NO: 5, and SEQ ID NO: 41. In certain embodiments, the oligonucleotide molecule consists of a nucleotide sequence set forth in SEQ ID NO: 1, in SEQ ID NO: 2, SEQ ID NO: 3, in SEQ ID NO: 4, in SEQ ID NO: 5, or in SEQ ID NO: 41. Each possibility represents a separate embodiment of the invention.

In some embodiments, the oligonucleotide is specific to a CFTR pre-mRNA. As used herein, the term "specific" refers to both base pair specificity and also gene specificity. In some embodiments, the oligonucleotide is specific to the CFTR gene. In some embodiments, the oligonucleotide is specific to an intronic sequence of CFTR. In some embodiments, the oligonucleotide is specific to a cryptic exon in CFTR. In some embodiments, the oligonucleotide is specific to a nucleic acid sequence of intron 22 of CFTR. In some embodiments, the nucleic acid sequence of intron 22 is intron 22 cryptic exon of CFTR.

In some embodiments, the oligonucleotide binds the CFTR pre-mRNA with perfect complementarity. In some embodiments, the oligonucleotide does not bind any gene other than CFTR with perfect complementarity. In some embodiments, the oligonucleotide does not bind any gene other than CFTR with a complementarity of greater than 70, 75, 80, 85, 90, 95, 97, 99 or 100%. Each possibility represents a separate embodiment of the invention. In some embodiments, the oligonucleotide does not bind any gene other than CFTR with a complementarity of greater than 90%. In some embodiments, the oligonucleotide binds SEQ ID NO: 37 with perfect complementarity. In some embodiments, the oligonucleotide does not bind any sequence other than SEQ ID NO: 37 with perfect complementarity. In some embodiments, the oligonucleotide does not bind any sequence other than SEQ ID NO: 37 with complementarity of greater than 70, 75, 80, 85, 90, 95, 97, 99 or 100%. Each possibility represents a separate embodiment of the invention. In some embodiments, the oligonucleotide does not bind any sequence other than SEQ ID NO: 37 with a complementarity of greater than 90%. In some embodiments, the oligonucleotide does not bind with perfect complementarity to anywhere in the genome of a cell other than within CFTR. In some embodiments, the oligonucleotide does not bind with complementarity of greater than 70, 75, 80, 85, 90, 95, 97, 99 or 100% to anywhere in the genome of a cell other than within CFTR. Each possibility represents a separate embodiment of the invention. In some embodiments, the cell is a mammalian cell. In some embodiments, the mammal is a human.

In some embodiments, the oligonucleotide modulates expression of CFTR. In some embodiments, the oligonucleotide modulates splicing of CFTR. In some embodiments, the oligonucleotide modulates splicing, e.g., suppresses inclusion, of intron 22 cryptic exon of CFTR. In some embodiments, the oligonucleotide does not cause an off-target effect. In some embodiments, off-target is a target other than CFTR. In some embodiments, off-target is a target other than splicing, e.g., suppressing the inclusion, of intron 22 cryptic exon of CFTR. In some embodiments, the oligonucleotide does not substantially or significantly modulate expression of a gene other than CFTR. In some embodiments, the oligonucleotide does not substantially or significantly modulate splicing of a gene other than CFTR. In some embodiments, the oligonucleotide does not substantially or significantly modulate splicing of an exon other than intron 22 cryptic exon of CFTR. In some embodiments, substantial modulation of expression is a change in expression of at least 5, 10, 15, 20, 25, 30, 35, 40, 45 or 50%. Each possibility represents a separate embodiment of the invention. In some embodiments, substantial modulation of expression is a change in expression of at least 20%.

In some embodiments, an oligonucleotide as disclosed herein targets, complements, suppresses, or any combination thereof, the inclusion of intron 22 cryptic exon to the mature CFTR mRNA transcribed from a mutated allele of the CFTR gene. In some embodiments, an oligonucleotide as disclosed herein does not target, complement, suppresses, or any combination thereof, splicing modulation of CFTR pre-mRNA transcribed from a wild type allele of the CFTR gene. In some embodiments, an oligonucleotide as disclosed herein targets, complements, suppresses, or any combination thereof at least 2 fold more efficiently, at least 3 fold more efficiently, at least 5 fold more efficiently, at least 7 fold more efficiently, at least 10 fold more efficiently, at least 20 fold more efficiently, at least 50 fold more efficiently, or at least 100 fold more efficiently, the inclusion of intron 22 cryptic exon into the mature CFTR mRNA transcribed from a mutated allele of the CFTR gene compared to the wild type allele of the CFTR gene, or any value and range therebetween. Each possibility represents a separate embodiment of the invention. In some embodiments, an oligonucleotide as disclosed herein targets, complements, suppresses, or any combination thereof 2-10 fold more efficiently, 3-50 fold more efficiently, 5-100 fold more efficiently, 7-20 fold more efficiently, 2-40 fold more efficiently, 2-25 fold more efficiently, 50-150 fold more efficiently, or 2-100 fold more efficiently, the inclusion of intron 22 cryptic exon into the mature CFTR mRNA transcribed from a mutated allele of the CFTR gene compared to the wild type allele of the CFTR gene. Each possibility represents a separate embodiment of the invention.

In some embodiments, an oligonucleotide of the invention fully complements with a mutated allele of the CFTR gene. As used herein, the term "fully complements" refers to 100% hybridization, meaning the mutated CFTR allele and the oligonucleotide represent a reversed and complementary nucleic acid sequence versions of one another, as would be apparent to one of ordinary skill in the art of molecular biology. In some embodiments, an oligonucleotide of the invention partially complements with the wild type allele of the CFTR gene. As used herein, the term "partially" refers to any value or range lower than 100%. In some embodiments, the oligonucleotide of the invention and the wild type CFTR allele represent a reversed and complementary nucleic acid sequence version of one another which differ by at least one nucleotide, e.g., comprising at least one mismatched nucleotide.

In some embodiments, the oligonucleotide of the invention, and method of using same, provide the exclusion of a cryptic exon from the mature CFTR mRNA transcribed from a mutated allele of the CFTR gene. In some embodiments, the mature mRNA transcribed from the wild type allele is devoid of the cryptic exon.

In some embodiments, the cryptic exon is intron 22 cryptic exon. In some embodiments, the cryptic exon is 80-90 bases long.

In some embodiments, the oligonucleotide comprises an active fragment of any one of SEQ ID NOs: 1-25, and 41-44.

In some embodiments, the oligonucleotide comprises an active fragment of any one of SEQ ID NOs: 1-5, and 41.

As used herein, the term "active fragment" refers to a fragment that is 100% identical to a contiguous portion of the full nucleotide sequence of the oligonucleotide, providing that at least: 30%, 40%, 50%, 60%, 70%, 80% or 90% of the activity of the original oligonucleotide sequence is retained, or any value and range therebetween. Each possibility represents a separate embodiment of the present invention.

In some embodiments, the subject is heterozygous to the 3849+10Kb C-to-T mutation. In some embodiments, a subject treated according to the method of the invention, comprises or is characterized by having a mixture of a wild type full-length and fully functional CFTR protein encoded from the wild type allele and a full-length and fully functional CFTR protein encoded from the pre-mRNA from which the inclusion of intron 22 cryptic exon was suppressed using the oligonucleotide of the invention. In some embodiments, the oligonucleotide of the invention does not reduce the level of the wild type full-length and fully functional CFTR protein in a subject, e.g., heterozygous to the mutation disclosed hereinabove.

The present invention further provides, in another aspect, a pharmaceutical composition comprising a synthetic oligonucleotide molecule as described above, and a pharmaceutically acceptable carrier.

The term "pharmaceutically acceptable carrier" as used herein refers to any of the standard pharmaceutical carriers known in the field such as sterile solutions, tablets, coated tablets, and capsules. Typically, such carriers contain excipients such as starch, milk, sugar, certain types of clay, gelatin, stearic acids, or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc). Compositions comprising such carriers are formulated by well-known conventional methods. Depending on the intended mode of administration and the intended use, the compositions may be in the form of solid, semi-solid, or liquid dosage forms, such, for example, as powders, granules, crystals, liquids, suspensions, liposomes, nano-particles, nano-emulsions, pastes, creams, salves, etc., and may be in unit-dosage forms suitable for administration of relatively precise dosages.

In certain embodiments, the pharmaceutical composition is formulated for oral administration. In certain embodiments, the pharmaceutical composition is formulated for nasal administration. In certain embodiments, the pharmaceutical composition is formulated for administration by inhalation. In certain embodiments, the pharmaceutical composition is formulated for abdominal administration. In certain embodiments, the pharmaceutical composition is formulated for subcutaneous administration. In certain embodiments, the pharmaceutical composition is formulated for intra-peritoneal administration. In certain embodiments, the pharmaceutical composition is formulated for intravenous administration.

In some embodiments, the pharmaceutical composition is formulated for systemic administration. In some embodiments, the pharmaceutical composition is formulated for administration to a subject. In some embodiments, the subject is a human subject. It will be understood by a skilled artisan that a pharmaceutical composition intended to administration to a subject should not have off-target effects, i.e. effects other than the intended therapeutic ones. In some embodiments, the pharmaceutical composition is devoid of a substantial effect on a gene other than CFTR. In some embodiments, the pharmaceutical composition is devoid of any substantial effect other than suppressing the inclusion of intron 22 cryptic exon to the mature CFTR. In some embodiments, a substantial effect is one with a phenotypic result. In some embodiments, a substantial effect is a deleterious effect. In some embodiments, deleterious is with respect to the health and/or wellbeing of the subject.

In some embodiments, the composition administered by inhalation. In some embodiments, the composition is an inhalation composition. in some embodiments, the composition is a pharmaceutical composition.

Being a long-known and well-studied disease, certain drugs and agents are known in the art for the treatment of Cystic Fibrosis patients. Administrating a synthetic polynucleotide molecule according to the present invention with one or more of these drugs may be beneficial in achieving significant therapeutic results.

In certain embodiments, the pharmaceutical composition further comprises one or more CFTR modifiers.

In some embodiments, the method further comprises administering to the subject a therapeutically effective amount of one or more CFTR modifiers.

In some embodiments, the CFTR modifier increases the duration of the CFTR gate being open, chloride flow through the CFTR gate, CFTR protein proper folding, the number of CFTR anchored to the cell membrane, or any combination thereof. Each possibility represents a separate embodiment of the invention.

In some embodiments, the modifier is selected from: potentiator, corrector, and amplifier.

As used herein, the term "potentiator" refers to any agent that increases the probability that a defective CFTR will be open and therefore allows chloride ions to pass through the channel pore.

As used herein, the term "corrector" refers to any agent that assists in proper CFTR channel folding so as to enable its trafficking to the cell membrane.

As used herein, the term "amplifier" refers to any agent that induces a cell to increase its CFTR protein production rates or yields, therefore resulting in an increased amount of the CFTR protein.

In certain embodiments, the CFTR modifier is selected from: a CFTR-splicing-modulating agent, Translational Read-Through agent, a CFTR amplifier, a CFTR potentiator and a CFTR corrector. In certain embodiments, the CFTR-splicing-modulating agent is a different synthetic oligonucleotide molecule capable of suppressing intron 22 cryptic exon inclusion in the mature CFTR mRNA; the Translational Read-Through agent is selected from the group consisting of 3-[5-(2-fluorophenyl)-1,2,4-oxadiazol-3-yl]benzoic acid (Ataluren) and ELX-02; the CFTR amplifier is PTI-428; the CFTR potentiator is selected from the group consisting of N-(2,4-Di-tert-butyl-5-hydroxyphenyl)-4-oxo-1,4-dihydroquinoline-3-carboxamide (Ivacaftor), QBW251, PTI-808 and VX-561 (deuterated ivacaftor); the CFTR potentiator is N-(2,4-Di-tert-butyl-5-hydroxyphenyl)-4-oxo-1,4-dihydroquinoline-3-carboxamide (Ivacaftor); or the CFTR corrector is selected from the group consisting of 3-{6-{[1-(2,2-difluoro-1,3-benzodioxol-5-yl)cyclopropanecarbonyl]amino}-3-methylpyridin-2-yl}benzoic acid (Lumacaftor), 1-(2,2-difluoro-1,3-benzodioxol-5-yl)-~ {N}-[1-[(2~ {R})-2,3-dihydroxypropyl]-6-fluoro-2-(1-hydroxy-2-methylpropan-2-yl) indol-5-yl|cyclopropane-1-carboxamide (Tezacaftor), VX-659, VX-445, VX-152 and VX-440, GLPG2222, FDL169 and PTI-801.

In certain embodiments, the pharmaceutical composition comprises at least about 1 nM of the synthetic oligonucleotide molecule. In certain embodiments, the pharmaceutical composition comprises at least about 2.5 nM of the synthetic oligonucleotide molecule. In certain embodiments, the pharmaceutical composition comprises at least about 10 nM of the synthetic oligonucleotide molecule. In certain embodiments, the pharmaceutical composition comprises 2.5 nM to 10 nM of the synthetic oligonucleotide molecule.

In certain embodiments, the pharmaceutical composition comprises 1 nM to 1 µM of the synthetic oligonucleotide molecule. In certain embodiments, the pharmaceutical composition comprises 1 nM to 0.5 µM of the synthetic oligonucleotide molecule. In certain embodiments, the pharmaceutical composition comprises 1 nM to 100 nM of the synthetic oligonucleotide molecule.

The present invention further provides, in another aspect, a synthetic oligonucleotide molecule as described above, or a pharmaceutical composition as described above, for use in the modulation of splicing of a CFTR pre-mRNA transcribed from a CFTR gene having a 3849+10Kb C-to-T mutation.

The phrase "modulation of splicing" as used herein refers to affecting a change in the level of any RNA or mRNA variant produced by the CFTR native pre-mRNA. For example, modulation may mean e.g. causing an increase or decrease in the level of abnormal CFTR mRNA, causing an increase or decrease in the level of normal, full-length CFTR mRNA, and/or causing an increase or decrease in the level of abnormal CFTR RNA or mRNA comprising a premature termination codon (non-sense codon). It is therefore evident that any change in ratio between certain CFTR splicing variants is also considered to be the result of splicing modulation. Each possibility represents a separate embodiment of the present invention. In certain embodiments, modulation means increasing the level of normal, full-length CFTR mRNA and/or decreasing the level of abnormal CFTR mRNA.

In certain embodiments, the use is for reducing the level of an mRNA molecule comprising the intron 22 cryptic exon. In certain embodiments, the use is for reducing the level of an mRNA molecule comprising the nucleotide sequence set forth in SEQ ID NO: 36. In certain embodiments, the use is for increasing the level of normal, full-length CFTR mRNA. In certain embodiments, the use is for increasing the level of an mRNA molecule comprising the nucleotide sequence set forth in SEQ ID NO: 34. In certain embodiments, the use is for correcting or improving chloride transport through the CFTR channel. In certain embodiments, the use is for increasing the production of functional CFTR protein. Each possibility represents a separate embodiment of the present invention.

The present invention further provides, in another aspect, a synthetic oligonucleotide molecule as described above, or a pharmaceutical composition as described above, for use in a method for improving at least one clinical parameter of Cystic Fibrosis.

The invention further provides, in another aspect, a method for improving at least one clinical parameter of Cystic Fibrosis in a patient in need thereof, comprising the step of administering a therapeutically effective amount of a synthetic polynucleotide molecule as described above to the patient.

The term "a therapeutically effective amount" as used herein refers to an amount necessary for improving at least one clinical parameter of Cystic Fibrosis or reducing the severity of at least one clinical parameter of Cystic Fibrosis in a patient. The therapeutically effective amounts may differ according to the patient's status, the synthetic polynucleotide molecule's administration route, excipient usage and co-usage of other active agents.

In certain embodiments, the clinical parameter is selected from the group consisting of lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms. Each possibility represents a separate embodiment of the invention.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "condition" includes anatomic and physiological deviations from the normal that constitute an impairment of the normal state of the living animal or one of its parts, that interrupts or modifies the performance of the bodily functions.

As used herein, the terms "subject" or "individual" or "animal" or "patient" or "mammal," refers to any subject, particularly a mammalian subject, for whom therapy is desired, for example, a human.

Being a genetic disease, Cystic Fibrosis currently cannot yet be cured, but its clinical manifestations and/or symptoms can be treated by the oligonucleotides of the present invention, for a marked increase and/or improvement in a patient's clinical status and quality of life.

The term "improving" as used herein refers to a favorable change, i.e. an increase or a decrease of at least 5%, at least 10%, at least 15%, at least 20%, at least 25%, at least 30%, at least 35%, at least 40%, at least 45%, or at least 50% in a clinical parameter of Cystic Fibrosis.

Different routes of AOs delivery have been examined in animal models and applied in clinical trials, chosen primarily according to the target tissue. For example, 20 MP was administered to DMD patients (PRO-051) by local intramuscular injection (van Deutekom et al., 2007), and by abdominal subcutaneous injections (Goemans et al., 2011). 20 MP was also administered to a SMA mouse model by intracerebroventricular injection (Williams et al., 2009; Hua et al., 2010). PMO was administered to a DMD mouse model by intramuscular injection (Gebski, Mann, Fletcher, & Wilton, 2003), and repeated weekly intraperitoneal injections (Goyenvalle et al., 2010). PMO was also administered to a SMA mouse model by intracerebroventricular injection (Porensky et al., 2012), and to DMD patients (AVI-4658) by local intramuscular injection (Kinali et al., 2009), or intravenously administration (Cirak et al., 2011; Mendell et al., 2013).

In certain embodiments, the method further comprises administering at least one additional anti-Cystic-Fibrosis agent to the patient. In certain such embodiments, the additional anti-Cystic-Fibrosis agent is selected from the group consisting of a CFTR-splicing-modulating agent, a CFTR potentiator and a CFTR corrector. Each possibility represents a separate embodiment of the present invention. In certain embodiments, the administration of the therapeutically effective amount of a synthetic polynucleotide molecule of the present invention and the administration of the at least one additional anti-Cystic-Fibrosis agent are independently oral, nasal, aerosol, inhalational, abdominal, subcutaneous, intra-peritoneal or intravenous administration. Each possibility represents a separate embodiment of the present invention. It should be understood that the selection of an administration route depends on the nature of the therapeutic agent and the site of its intended effect, and thus certain agents may be administered via the same or different administration routes.

In certain embodiments, the administration of the synthetic oligonucleotide molecule or of the pharmaceutical composition is oral, nasal, inhalational, abdominal, subcutaneous, intra-peritoneal or intravenous administration.

In certain embodiments, the synthetic oligonucleotide molecule is administered in a concentration of at least about 1 nM. In certain embodiments, the synthetic oligonucleotide molecule is administered in a concentration of at least about 2.5 nM. In certain embodiments, the synthetic oligonucleotide molecule is administered in a concentration of at least about 10 nM. In certain embodiments, the synthetic oligonucleotide molecule is administered in a concentration of 2.5 nM to 10 nM.

The present invention further provides, in another aspect, the use of a synthetic oligonucleotide molecule as described above, or of a pharmaceutical composition as described above, in preparing a medicament.

In certain embodiments, the medicament is for treating or ameliorating a symptom of Cystic Fibrosis. In some embodiments, the medicament improves at least one clinical parameter of Cystic Fibrosis. According to some embodiments, the clinical parameter is selected from the group consisting of lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms. Each possibility represents a separate embodiment of the invention.

The present invention further provides, in another aspect, a kit comprising a synthetic oligonucleotide molecule as described above.

In certain embodiments, the kit further comprises an additional anti-Cystic-Fibrosis agent.

In certain embodiments, the synthetic oligonucleotide and the additional anti-Cystic-Fibrosis agent are comprised in one pharmaceutical composition. In certain embodiments, the synthetic oligonucleotide and the additional anti-Cystic-Fibrosis agent are comprised in different pharmaceutical compositions. In certain embodiments, the synthetic oligonucleotide and the additional anti-Cystic-Fibrosis agent are independently formulated for oral, nasal, inhalation, abdominal, subcutaneous, or intra-peritoneal administration. Each possibility represents a different embodiment of the invention.

In certain embodiments, the synthetic oligonucleotide is in a concentration of at least about 1 nM. In certain embodiments, the synthetic oligonucleotide is in a concentration of at least about 2.5 nM. In certain embodiments, the synthetic oligonucleotide is in a concentration of at least about 10 nM. In certain embodiments, the synthetic oligonucleotide molecule is in a concentration of 2.5 nM to 10 nM.

The present invention further provides, in another aspect, a synthetic oligonucleotide molecule, consisting of 18-50 consecutive bases that are complementary to a pre-mRNA transcript of a CFTR gene having a 3849+10Kb C-to-T mutation and at least partly suppresses the inclusion of intron 22 cryptic exon in the mature CFTR mRNA, comprising a nucleotide sequence set forth in one of SEQ ID NO: 1 to SEQ ID NO: 25, and SEQ ID NO: 41 to SEQ ID NO: 44.

The present invention further provides, in another aspect, a synthetic oligonucleotide molecule, consisting of 17-50 consecutive bases that are complementary to a pre-mRNA transcript of a CFTR gene having a 3849+10Kb C-to-T mutation and at least partly suppresses the inclusion of intron 22 cryptic exon in the mature CFTR mRNA, comprising a nucleotide sequence set forth in one of SEQ ID NO: 1 to SEQ ID NO: 25 and SEQ ID NO: 40 to SEQ ID NO: 71.

In certain embodiments, the oligonucleotide molecule comprises or consists of a nucleotide sequence set forth in one of SEQ ID NO: 1 to SEQ ID NO: 10. In certain embodiments, the oligonucleotide molecule comprises or consists of a nucleotide sequence set forth in one of SEQ ID NO: 1 to SEQ ID NO: 5, and SEQ ID NO: 41. In certain embodiments, the oligonucleotide molecule comprises or consists of a nucleotide sequence set forth in SEQ ID NO: 1, in SEQ ID NO: 3, in SEQ ID NO: 4, in SEQ ID NO: 5, or SEQ ID NO: 41. In certain embodiments, the oligonucleotide molecule comprises or consists of a nucleotide sequence set forth in SEQ ID NO: 7.

In certain embodiments, the oligonucleotide molecule comprises a nucleotide sequence set forth in one of SEQ ID NO: 40 to SEQ ID NO: 71. In certain embodiments, the oligonucleotide molecule comprises a nucleotide sequence set forth in one of SEQ ID NO: 40 to SEQ ID NO: 48. In certain embodiments, the oligonucleotide molecule comprises a nucleotide sequence set forth in one of SEQ ID NO: 49 to SEQ ID NO: 53. In certain embodiments, the oligonucleotide molecule comprises a nucleotide sequence set forth in one of SEQ ID NO: 54 to SEQ ID NO: 58. In certain embodiments, the oligonucleotide molecule comprises a nucleotide sequence set forth in one of SEQ ID NO: 59 to SEQ ID NO: 63. In certain embodiments, the oligonucleotide molecule comprises a nucleotide sequence set forth in one of SEQ ID NO: 54 to SEQ ID NO: 71.

The present invention further provides, in another aspect, a synthetic oligonucleotide sequence consisting of 18-20 consecutive bases comprising the sequence GAUGGAAGA (SEQ ID NO: 38), wherein the synthetic oligonucleotide sequence is complementary to a pre-mRNA transcript of a CFTR gene having a 3849+10Kb C-to-T mutation.

The present invention further provides, in another aspect, a synthetic oligonucleotide sequence consisting of 17-20 consecutive bases comprising the sequence GAUGGAAGA (SEQ ID NO: 38), wherein the synthetic oligonucleotide sequence is complementary to a pre-mRNA transcript of a CFTR gene having a 3849+10Kb C-to-T mutation.

In certain embodiments, the oligonucleotide sequence is complementary to a nucleotide sequence within SEQ ID NO: 37. In certain embodiments, the oligonucleotide sequence is selected from the group consisting of: SEQ ID NOs: 1, 2, 4 and 7. In certain embodiments, the synthetic oligonucleotide sequence comprises the sequence CAACAGAUGGAAGA (SEQ ID NO: 39). In certain embodiments, the sequence is selected from the group consisting of: SEQ ID NOs: 1, 2 and 4.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation.

In some embodiments, the kit of the invention comprises: at least one oligonucleotide; and at least one of: at least one CFTR modifier; or at least one CF drug, wherein the oligonucleotide is selected from SEQ ID NOs: 1-25, and 41-44, and wherein the CFTR modifier is selected from: CFTR potentiator, CFTR corrector, and CFTR amplifier.

In some embodiments, the CF drug is an antibiotic drug, a bronchodilator, a corticosteroid, or any combination thereof.

Types and doses of CF drugs, such as an antibiotic, a bronchodilator, and a corticosteroid, would be apparent to one of ordinary skill in the art. Non-limiting examples of CF drugs, such as antibiotics include, but are not limited to, cloxacillin, dicloxacillin, cephalosporin, trimethoprim, sulfamethoxazole, erythromycin, amoxicillin, clavulanate, ampicillin, tetracycline, linezolid, tobramycin or aztreonam lysine, fluoroquinolone, gentamicin, and monobactam with antipseudomonal activity.

In some embodiments, the components of the kit disclosed above are sterile. As used herein, the term "sterile" refers to a state of being free from biological contaminants. Any method of sterilization is applicable and would be apparent to one of ordinary skill in the art.

In some embodiments, the components of the kit are packaged within a container.

In some embodiments, the container is made of a material selected from the group consisting of thin-walled film or plastic (transparent or opaque), paperboard-based foil, rigid plastic, metal (e.g., aluminum), glass, etc.

In some embodiments, the content of the kit is packaged, as described below, to allow for storage of the components until they are needed.

In some embodiments, some or all components of the kit may be packaged in suitable packaging to maintain sterility.

In some embodiments, the components of the kit are stored in separate containers within the main kit containment element e.g., box or analogous structure, may or may not be an airtight container, e.g., to further preserve the sterility of some or all of the components of the kit.

In some embodiments, the instructions may be recorded on a suitable recording medium or substrate. For example, the instructions may be printed on a substrate, such as paper or plastic, etc.

In some embodiments, the instructions may be present in the kit as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

According to some embodiments, there is provided a method for producing a compound suitable for treating CF.

In some embodiments, the method comprises obtaining a compound that binds to intron 22 of the CFTR pre-mRNA. In some embodiments, the method comprises obtaining a compound that binds to SEQ ID NO: 37. In some embodiments, the method comprises assaying the inclusion of intron 22 cryptic exon in the mature CFTR mRNA in the presence of the obtained compound, and selecting at least one compound that suppresses the inclusion of intron 22 cryptic exon in the mature CFTR mRNA, thereby producing a compound suitable for treating CF.

In some embodiments, the compound is an oligonucleotide. In some embodiments, the oligonucleotide is an oligonucleotide as disclosed and as described herein.

Methods of assaying cryptic exon inclusion are common. Non-limiting examples of such methods include, but are not limited to, PCR, qPCR, gene sequencing, northern-blot, dot-blot, in situ hybridization, or others all of which would be apparent to one of ordinary skill in the art.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive "or", and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Unless specifically stated or obvious from context, as used herein, the term "or" is understood to be inclusive.

Throughout this specification and claims, the word "comprise", or variations such as "comprises" or "comprising", indicate the inclusion of any recited integer or group of integers but not the exclusion of any other integer or group of integers.

As used herein, the term "consists essentially of", or variations such as "consist essentially of" or "consisting essentially of", as used throughout the specification and claims, indicate the inclusion of any recited integer or group of integers, and the optional inclusion of any recited integer or group of integers that do not materially change the basic or novel properties of the specified method, structure or composition.

As used herein, the terms "comprises", "comprising", "containing", "having" and the like can mean "includes", "including", and the like; "consisting essentially of" or "consists essentially of" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. In one embodiment, the terms "comprises," "comprising, "having" arc/is interchangeable with "consisting".

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments unless the embodiment is inoperative without those elements.

The terms "comprises", "comprising", "includes", "including", "having" and their conjugates mean "including but not limited to". This term encompasses the terms "consisting of" and "consisting essentially of". As used herein, the singular form "a", "an", and "the" include plural references unless the context clearly dictates otherwise. For example, the term "a compound" or "at least one compound" may include a plurality of compounds, including mixtures thereof.

The following examples are meant to be construed as non-limiting to the scope of the invention and are to serve merely as illustrative embodiments.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein, and the laboratory procedures utilized in the present invention include chemical, molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); "Cell Biology: A Laboratory Handbook", Volumes I-III Cellis, J. E., ed. (1994); The Organic Chemistry of Biological Pathways by John McMurry and Tadhg Begley (Roberts and Company, 2005); Organic Chemistry of Enzyme-Catalyzed Reactions by Richard Silverman (Academic Press, 2002); Organic Chemistry (6th Edition) by Leroy "Skip" G Wade; Organic Chemistry by T. W. Graham Solomons and, Craig Fryhle.

TABLE 1

Anti-Sense Oligonucleotides (ASOs).

| Name | SEQ ID NO: | Nucleotide sequence 5'→ 3' | Length (nucleotides) |
|---|---|---|---|
| SPL84-23 | 1 | CUGCAACAGAUGGAAGACUC | 20 |
| SPL84-22 | 2 | CAACAGAUGGAAGACUCUU | 19 |
| SPL84-17 | 3 | CUCCAGAAAUCAAGAUGAC | 19 |
| SPL84-25 | 4 | UACUGCAACAGAUGGAAGA | 19 |
| SPL84-2 | 5 | AUCAAGAUGACAAGUCAACU | 20 |
| SPL84-16 | 6 | GUGGUCUCCAGAAAUCAAG | 19 |
| SPL84-21 | 7 | GAUGGAAGACUCUUGUAAU | 19 |
| SPL84-1 | 8 | CAAGAUGACAAGUCAACUGAA | 21 |
| SPL84-7 | 9 | GAAAUCAAGAUGACAAGUCAAC | 22 |
| SPL84-19 | 10 | ACCUUGUGGUCUCCAGAAA | 19 |
| SPL84-18 | 11 | CCAGAAAUCAAGAUGACAAG | 20 |
| SPL84-13 | 12 | CACCAUUUUAAUACUGCAACA | 21 |
| SPL84-24 | 13 | UGGAAGACUCUUGUAAUUAUU | 21 |
| SPL84-3 | 14 | GAUGACAAGUCAACUGAAAUU | 21 |
| SPL84-15 | 15 | CUUUCAGGGUGUCUUACUC | 19 |
| SPL84-14 | 16 | UCAGGGUGUCUUACUCACC | 19 |
| SPL84-20 | 17 | AUUACCUUGUGGUCUCCAGA | 20 |
| SPL84-5 | 18 | GACAAGUCAACUGAAAUUUAG | 21 |
| SPL84-8 | 19 | CAACUGAAAUUUAGAUCCACA | 21 |
| SPL84-6 | 20 | AGUCAACUGAAAUUUAGAUCC | 21 |
| SPL84-9 | 21 | GUGUCUUACUCACCAUUUUAA | 21 |
| SPL84-10 | 22 | GUGUCUUACUCACCAUUU | 18 |
| SPL84-12 | 23 | CUCACCAUUUUAAUACUGC | 19 |
| SPL84-4 | 24 | GACAAGUCAACUGAAAUU | 18 |
| SPL84-11 | 25 | CUUACUCACCAUUUUAAUAC | 20 |
| 5' Kole | 26 | GUCUUACUCACCAUUUUA | 18 |
| 3' Kole | 27 | CAAGUCAACUGAAAUUUAG | 19 |
| stop Kole | 28 | CUUGUAAUUAUUUUUACAU | 19 |
| ASO84-1 | 29 | AAAUCAAGAUGACAAGUCAACUGAA | 25 |
| ASO84-2 | 30 | CUUGUGGUCUCCAGAAAUCAAGAUG | 25 |
| ASO84-3 | 31 | AACAGAUGGAAGACUCUUGUAAUUA | 25 |
| ASO84-3 | 32 | UCAGGGUGUCUUACUCACCAUUUUA | 25 |

TABLE 1-continued

Anti-Sense Oligonucleotides (ASOs).

| Name | SEQ ID NO: | Nucleotide sequence 5'→ 3' | Length (nucleotides) |
|---|---|---|---|
| Control | 33 | GACCACUUGCCACCCAUC | 18 |
| SPL84-23-1 | 40 | CUGCAACAGAUGGAAGACU | 19 |
| SPL84-23-2 | 41 | UGCAACAGAUGGAAGACUC | 19 |
| SPL84-23-3 | 42 | CUGCAACAGAUGGAAGAC | 18 |
| SPL84-23-4 | 43 | GCAACAGAUGGAAGACUC | 18 |
| SPL84-23-5 | 44 | UGCAACAGAUGGAAGACU | 18 |
| SPL84-23-6 | 45 | CUGCAACAGAUGGAAGA | 17 |
| SPL84-23-7 | 46 | CAACAGAUGGAAGACUC | 17 |
| SPL84-23-8 | 47 | UGCAACAGAUGGAAGAC | 17 |
| SPL84-23-9 | 48 | GCAACAGAUGGAAGACU | 17 |
|  | 49 | CUCCAGAAAUCAAGAUGA | 18 |
|  | 50 | UCCAGAAAUCAAGAUGAC | 18 |
|  | 51 | CUCCAGAAAUCAAGAUG | 17 |
|  | 52 | CCAGAAAUCAAGAUGAC | 17 |
|  | 53 | UCCAGAAAUCAAGAUGA | 17 |
|  | 54 | CAACAGAUGGAAGACUCU | 18 |
|  | 55 | AACAGAUGGAAGACUCUU | 18 |
|  | 56 | ACAGAUGGAAGACUCUU | 17 |
|  | 57 | AACAGAUGGAAGACUCU | 17 |
|  | 58 | UACUGCAACAGAUGGAAG | 18 |
|  | 59 | ACUGCAACAGAUGGAAGA | 18 |
|  | 60 | UACUGCAACAGAUGGAA | 17 |
|  | 61 | ACUGCAACAGAUGGAAG | 17 |
|  | 62 | AUCAAGAUGACAAGUCAAC | 19 |
|  | 63 | UCAAGAUGACAAGUCAACU | 19 |
|  | 64 | AUCAAGAUGACAAGUCAA | 18 |
|  | 65 | CAAGAUGACAAGUCAACU | 18 |
|  | 66 | UCAAGAUGACAAGUCAAC | 18 |
|  | 67 | AUCAAGAUGACAAGUCA | 17 |
|  | 68 | AAGAUGACAAGUCAACU | 17 |
|  | 69 | UCAAGAUGACAAGUCAA | 17 |
|  | 70 | CAAGAUGACAAGUCAAC | 17 |
| SPL84-26 | 71 | AAUUAUUUUUCAUUACCUUG | 20 |

TABLE 2

CFTR-related sequences (all in sense orientation).

| Name | SEQ ID NO: | Chr. 7 position |
|---|---|---|
| Mature CFTR mRNA | 34 | aauuggaagc aaaugacauc acagcagguc agagaaaaag gguugagcgg caggcaccca gaguaguagg ucuuuggcau uaggagcuug agcccagacg gcccuagcag ggaccccagc gcccgagaga ccaugcagag gucgccucug gaaaaggcca gcguugucuc caaacuuuuu uucagcugga ccagaccaau uuugaggaaa ggauacagac agcgccugga auugucagac auauaccaaa ucccuucugu ugauucugcu gacaaucuau cugaaaaauu gaaagagaa ugggauagag agcuggcuuc aaagaaaaau ccuaaacuca uuaaugcccu ucggcgaugu uuuuucugga gauuuauguu cuaggaaauc uuuuuauauu uaggggaagu caccaaagca guacagccuc ucuuacuggg aagaaucaua gcuuccuaug acccggauaa caaggaggaa cgcucaucg cgauuuaucu aggcauaggc uuaugccuuc ucuuuauugu gaggacacug cuccuacacc cagccauuuu uggccuucau cacauuggaa ugcagaugaa aauagcuaug uuuaguuuga uuuauaagaa gacuuuaaag cugcaagcc guguucuaga uaaaauaagu auuggacaac uuguuagucu ccuuccaac aaccugaaca aauuugauga aggacuugca uuggcacauu cguguggau cgcuccuuug caaguggcac uccucauggg gcuaaucugc gcuaaucugc cuucugugga cuugguuucc ugauagaccu ugcccuuuuu caggcugggc uagggagaau gaugaugaag uacagagauc agagagcugg gaagaucagu gaaagacuug ugauuaccuc agaaaugauu gaaauauccc aaucuguuaa ggcauacugc ugggaagaag caauggaaaa augauugaa aacuuaagac aaacagaacu gaaacugacu cggacauggc ccuaugugag auacuucaau agcucagccu cuucuucuc aggguucuuu guggugu uaucugugcu ucccuaugca cuaaucaaag gaaucauccu ccggaaaaua uucaccacca ucucauucug cauuguucug cgcauggcgg ucacucggca auuucccugg gcuguacaaa cauggucauga cucucuugga gcaauaaaca aaauacagga uuucuuuaca aagcaagaau auaaagacau uuaaacgacua cagaaguagu gauggagaau guaacagccu cugggaggag ggguuugggg gaauuauuug agaaagcaaa acaaaacauu aacaauagaa aaacucucaa ugguggaugac agcucuucu ucaguaauuu cucacucuug gguacccug uccugaaaga uauuaauuuc aagauagaaa gaggacaguu guuggcgguu gcuggauccu cuggagcagg caagacuuca cuucaauugg ugauuauggg |

TABLE 2-continued

CFTR-related sequences (all in sense orientation).

| Name | SEQ ID NO: | Chr. 7 position |
|------|------------|-----------------|

```
agaacuggag ccuucagagg guaaaauuaa gcacagugga agaauuucau
ucuguucuca guuuccugg auuaugccug gcaccauuaa agaaaauauc
aucuuuggug uuuccauga ugaauauaga uacagaagcg ucaucaaagc
augccaacua gaagaggaca ucuccaaguu ugcagagaaa gacaauauag
uucuuggaga aggggaauc acacugagug gaggucaacg agcaagaauu
ucuuuagcaa gagcaguaua caaagaugcu gauuuguauu auuagacuc
uccuuuugga uaccuagaug uuuuaacaga aaaagaaaua uuugaaagcu
gugucuguaa acugauggcu aacaaaacua ggauuuuggu cacuucuaaa
auggaacauu uaaagaaagc ugacaaaaua uuaauuuugc augaagguag
cagcuauuuu uaugggacau uuucagaacu ccaaaaucua cagccagacu
uuagcucaaa acucauggga ugugauucu ucgaccauu uagugcagaa
agaagaaauu caauccuaac ugagaccuua caccguuucu cauuagaagg
agaugcuccu gucuccugga cagaaacaaa aaaacaaucu uuuaaacaga
cuggagaguu ugggaaaaa aggaagaauu cuauucucaa uccaaucaac
ucuauacgaa aauuuccau ugugcaaaag acucccuuac aaaugaaugg
caucgaagag gauucugaug agccuuuaga gagaaggcug uccuuaguac
cagauucuga gcagggagag gcgauacugc cucgcaucag cgugaucagc
acuggcccca cgcuucaggc acgaaggagg cagucugucc ugaaccugau
gacacacuca guuaaccaag gucagaacua ucaccgaaag acaacagcau
ccacacgaaa agugucacug gccccucagg caaacuugac ugaacuggau
auauauucaa gaagguuauc ucaagaaacu ggcuuggaaa uaagugaaga
aauuaacgaa gaagacuuaa aggagugcuu uuuugaugau auggagagca
uaccagcagu gacuacaugg aacacauacc uucgauauau uacguccac
aagagcuuaa uuuuugcu aauuggugc uuaguaauuu uucuggcaga
gguggcugcu ucuuugguug ugcugugcu ccuggaaac acuccucuuc
aagacaaagg gaauagacu cauaguagaa auaacagcua ugcagugauu
aucaccagca ccaguucgua uuaugguu uacauuacg ugggagagc
cgacacuuug cuugcuaugg gauucuucag aggucuacca cuggugcaua
cucuaaucac agugcgaaa auuuuacacc acaaaauguu acauucuguu
cuucaagcac cuaugucaac ccucaacacg uugaaagcag guggauucu
uaauagauuc uccaaagaua uagcaauuuu ggaugaccuu cugccucuua
ccauauuuga cuucauccag uuguauuaa uugugauugg agcuauagca
guugucgcag uuuuacaacc cuacaucuuu guugcaacag ugccagugau
aguggcuuuu auuauguuga gagcauauuu ccuccaaaccc ucacagcaac
ucaaacaacu ggaaucgaa ggcaggaguc caauuuucac ucaucuuguu
acaagcuuaa aaggacuaug gacacucgu gccuucggac ggcagccuua
cuuugaaacu cuguuccaca aagcucugaa uuuacauacu gccaacuggu
ucuuguaccu gucaacacug cgcuggucc aaaugagaau agaaaugauu
uuugucaucu ucuucauugc uguuaccuuc auuccauuu uaacaacagg
agaaggagaa ggaagaguug guauuauccu gacuuuagcc augaauauca
ugaguacauu gcaguggcu guaaacucca gcauagaugu ggauagcuug
augcgaucug ugagccgagu cuuuaaguuc auugacaugc caacagaagg
uaaaccuacc aagucaacca aaccauacaa gaauggccaa cucucgaaag
uuaugauuau ugagaauuca cacgugaaga aagaugacau cuggcccuca
gggggccaaa ugacugucaa agaucucaca gcaaaauaca cagaaggugg
aaaugccaua uuagagaaca uuccuucuc aauaaguccu ggccagaggg
ugggccucuu gggaagaacu ggaucaggga agaguacuuu guuaucagcu
uuuugagac uacugaacac ugaaggagaa auccagaucg auggguguc
ugggauuca auaacuuugc aacagugag gaaagccuuu ggagugauac
cacagaaagu auuuauuuu ucuggaacau uuagaaaaaa cuuggauccc
uaugaacagu ggagugauca agaaauaugg aaaguugcag augagguugg
gcucagaucu gugauagaac aguuccugg gaagcuugac uuuguccuug
uggauggggg cugugucca agccauggcc acaagcaguu gaugugcuug
gcuagaucug uucucaguaa ggcgaagauc uugcugcugg augaaccag
ugcucauug gauccaguaa cauaccaaau aauuagaaga acucuaaaac
aagcauuugc ugauugcaca guaauucucu gugaacacag gauagaagca
augcuggaau gccaacaauu uuggucaua gaagagaaca aagugcggca
guacgauucc auccagaaac ugcuaacga gaggagccuc uuccggcaag
ccaucagccc cuccgacagg gugaagcucu ucccccaccg gaacucaagc
aagugcaagu cuaagcccca gauugcugcu cugaaaagg agacagaaga
agaggugcaa gauacaaggc uuuagagagc agcauaaaug uugacauggg
acauuugcuc auggaauugg agcucguggg acagucaccu cauggaauug
gagcucgugg aacaguuacc ucugccucag aaaacaagga ugaauuaagu
uuuuuuuaa aaaagaaaca uuugguaagg gaauugagg acacugauau
gggucuugau aaauggcuuc cuggcaauag ucaauugug ugaaagguac
uucaaauccu ugaagauuua ccacuugugu uuugcaagcc agauuuuccu
gaaacccuu gccaugugcu aguaauugga aaggcagcuc uaaaugucaa
ucagcuagu ugaucagcuu auugcuagu gaaacucguu aauuuguagu
guugagaag aacgaaauc auacuucuua ggguuugau uaaguaauga
uaacuggaaa cuucagcggu uuaauauaag uuguauuccu uuuucucucc
ucuccccaug auguuuagaa acacaacuau auuguuugcu aagcauucca
acuaucucau uccaagcaa guauuagaau accacaggaa ccacaagacu
gcacaucaaa auaugcccca uucaacaucu agugagcagu caggaaagag
aacuuccaga uccuggaaau cagguuuagu auuguccagg ucuaccaaaa
aucucaauau uucagauaau cacaauacau cccuuaccug ggaaagggcu
```

TABLE 2-continued

CFTR-related sequences (all in sense orientation).

| Name | SEQ ID NO: | Chr. 7 position |
|---|---|---|
| | | guuauaaucu uucacagggg acaggauggu ucccuugaug aagaaguuga uaugccuuuu cccaaccucca gaaagugaca agcucacaga ccuuugaacu agaguuuagc uggaaaagua uguuagugca aauugucaca ggacagcccu ucuuuccaca gaagcuccag guagagggug uguaaguaga uaggccaugg gcacuguggg uagacacaca ugaagcccaa gcauuuagau guauagguug augguggua guuuucaggc uagaugaug uacuucaugc ugucuacacu aagagagaau gagagacaca cugaagaagc accaaucaug aauuaguuuu auaugcuucu guuuuauaau uuugugaagc aaaauuuuuu cucuaggaaa uauuuauuuu aauaauguuu caaacauaua uaacaaugcu guauuuaaaa agaaugauua ugaauuacau uuguauaaaa uaauuuuuau auuugaaaua uugacuuuuu auggcacuag uauuucuag aaauauuaug uuaaaacugg gacagggag aaccuagggu gauauuaacc agggccaug aaucaccuuu uggucuggag ggaagccuug gggcugaugc aguguugcc cacagcugua ugauucccag ccagcacagc cucuuagaug caguucugaa gaagaugua ccaccagucu gacuguuucc aucaaggua cacugccuuc ucaacuccaa acugacucuu aagaagacug cauuauauu auuacuguaa gaaaaauauca cuugucaaua aaauccauac auuuguguga aa |
| Intron 22 cryptic exon * | 35 | TTGACTTGTCATCTTGATTTCTGGAGACCACAAGGTAATGA AAAATAATTACAAGAGTCTTCCATCTGTTGCAGTATTAAAA TG |
| Exons 1-27 + cryptic exon 22 | 36 | aauuggaagc aaaugacauc acagcaggcu agagaaaaag gguugagcgg caggcaccca gaguaguagg ucuuuggcau uaggagcuug agcccagacg gcccuagcag ggaccccagc ccccgagaga ccaugcagag gucgcccucug gaaaaggcca gcguugucuc caaacuuuuu uucagcugga ccagaccaau uuugaggaaa ggauacagac agcgccugga auugcagac auauaccaaa ucccuucugu ugauucugcu gacaaucuau cugaaaaauu ggaaagagaa ugggauagag agcuggcuuc aaagaaaaau ccuaaacuca uuaaugcccu ucggcgaugu uuuuucugga gauuuaugu cuauggaauc uuuuuauauu uaggggaagu caccaaagca guacagccuc ucuuacuggg aagaaucaua gcuuccuaug acccggauaa caaggaggaa cgcucuaucg cgauuuaucu aggcauaggc uuaugccuuc ucuuuauugu gaggacacug cuccuacacc cagccauuuu uggccuucau cacauuggaa ugcagaugag aauagcuaug uuuaguuuga uuuauaagaa gacuuuaaag cugucaagcc uguucuaga uaaaauaagu auuggacaac uuguuagucu ccuuccaac aaccugaaca aauuugauga aggacuugca uuggcacauu ucgugugau cgcucuuug caaguggcac uccucauggg gcuaaucugg gaguuguac aggcgucugc cuucugugga cuugguucc ugauagccu ugcccuuuuu caggcugggc uaggagagaau gaugaugaag uacagagauc agagagcugg gaagaucagu gaaagacuug ugauuaccuc agaaaugau gaaaauaucc aaucuguuaa ggcauacugc uggggaagaag caauggaaaa aaugauugaa aacuuaagac aaacagaacu gaaacugacu cggaaggcag ccuaugugag auacuucaau agcucagccu ucuucuucuc agggucuuu guggguguu uaucugugcu ucccuaugca cuaaucaaag gaaucauccu ccggaaaaua uuccaccaca ucucauucug cauuguucug cgcauggcgg ucacucggca auuucccugg gcuguacaaa cauggauga cucucuugga gcaauaaaca aaauacagga uuucuuacaa aagcaagaau auaagacauu ggauauaac uuacgacua cagaaguagu gauggagaau guaacagccu ucgggagga gggauugggg gaauuuauug agaaagcaaa acaaaacaau aacaauagaa aaacuuccua uggugaugac agccucuucu ucaguaauuu cucacuucuu gguacuccug uccugaaaga uauuaauuuc aagauagaaa gaggacaguu guuggcgguu gcuggaucca cuggagcagg caagacuuca cuucuaaugg ugauuaauggg uggugaugac agccucuucu ucaguaauuu cucacuucuu gguacuccug uccugaaaga uauuaauuuc aagauagaaa gaggacaguu guuggcgguu gcuggaucca cuggagcagg caagacuuca cuucuaaugg ugauuaugggg agaacuggag ccuucagagg guaaaauaaa gcacagugga agaauuucau ucguucuca guuuccugg auuaugccug gcaccauuaa agaaaauauc aucuuuggug uuccuauga ugaauauaga uacagaagcg ucaucaaagc augccaacua gaagaggaca ucuccaaguu ugcagagaaa gacaauauag ucuuggaga aggguggaauc acacugaga gagucaacg agcaagaauu ucuuuagcaa gagcaguaua caaagaugcc gauuuguauu uauuagacuc uccuuuugga uaccuagaug uuuuaacaga aaaagaaaua uuugaaagcu gugucuguaa acugauggcu aacaaaacua ggauuuuggu cacuucuaaa auggaacauu uaaagaaagc ugacaaaaua uuaauuuugc augaagguag cagcuauuuu uaugggacau uucagaacu ccaaaucua cagccagacu uuagcucaaa acucauggga ugugauucu ucgaccaauu uagugcagaa agaagaaauu caauccaaac ugagaccuua caccgsuucu cauuagaagg agaugcuccu cuccuugga cagaaacaaa aaacaauc uuuaaacaga cuggagaguu uggggaaaaa aggaagaauu cuauucuca auccaaucaac ucauacgaa aauuuccau ugugcaaag acuccuuuac aaaugaaug caucgaagag gauucugau gccuuuaga gagaggcug uccuuaguac cagauucga gcagggagag gcguauacgc cucgcaucag cgugaucgac acuggcccca cgcuuucagg acgaaggagg cagucugucc ugaaccugau gacacacuca guuaaccaag gucagaacauc uccgaaag acaacagcau ccacacgaaa agucacacug gccccucagg caaacuugac ugaacuggau auauauucaa gaagguuauc ucaagaaacu ggcuuggaaa uaagugaaga aauuaacgaa gaagacuuaa aggagugcuu uuuugaugau auggagagca |

TABLE 2-continued

CFTR-related sequences (all in sense orientation).

| Name | SEQ ID NO: | Chr. 7 position |
|---|---|---|
| | | uaccagcagu gacuacaugg aacacauacc uucgauauau uacuguccac |
| | | aagagcuuaa uuuuugugcu aauuuggugc uuaguaauuu uucuggcaga |
| | | gguggcugcu ucuuugguug ugcuguggcu ccuuggaaac acuccucuuc |
| | | aagacaaagg gaauaguacu cauaguagaa auaacagcua ugcagugaau |
| | | aucaccagca ccaguucgua uuauguguuu uacauuuacg ugggaguagc |
| | | cgacacuuug cuugcuaugg gauucuucag aggucuacca cuggugcaua |
| | | cucuaaucac agugucgaaa auuuuacacc acaaaauguu acauucuguu |
| | | cuucaagcac cuaugucaac ccucaacacg uugaaagcag gugggauucu |
| | | uaauagauuc uccaaagaua uagcaauuuu ggaugaccuu cugccucuua |
| | | ccauauuuga cuucauccag uuguuauuaa uugugauugg agcuauagca |
| | | guugucgcag uuuuacaacc cuacaucuuu guugcaacag ugccagugau |
| | | aguggcuuuu auuauguuga gagcauauuu ccuccaaacc ucacagcaac |
| | | ucaaacaacu ggaaucugaa ggcaggaguc caauuuucac ucaucuuguu |
| | | acaagcuuaa aaggacuaug gacacuucgu gccuucggac ggcagccuua |
| | | cuuugaaacu cuguuccaca aagcucugaa uuuacauacu gccaacuggu |
| | | ucuuguaccu gucaacacug cgcugguucc aaaugagaau agaaaugauu |
| | | uuugucaucu ucuucauugc uguuaccuuc auuccauuu aacaacagg |
| | | agaaggagaa ggaagaguug guauuauccu gacuuuagcc augaauauca |
| | | ugaguacauu gcagugggcu guaaaccuca gcaugaugu ggauagcuug |
| | | augcgaucug ugagccgagu cuuuaaguuc auugacaugc caacagaagg |
| | | uaaaccuacc aagucaacca aaccauacaa gaauggccaa cucucgaaag |
| | | uuaugauuau ugagaauuca cacgugaaga aagaugacau cuggcccuca |
| | | gggggccaaa ugacugucaa agaucucaca gcaaaauaca cagaaggugg |
| | | aaaugccaua uuagagaaca uuccuucuc aauaagucu ggccagaggu |
| | | ugacuugucaa ucuugauuuc uggagaccac aagguaauga aaaauaauua |
| | | caagagucuu ccaucuguug caguauuaaa auggugggcc ucuugggaag |
| | | aacuggauca gggaagagua cuuuguuauc agcuuuuuug agacuacuga |
| | | acacugaagg agaaauccag aucgauggu ugucuuggga uucaauaacu |
| | | uugcaacagu ggaggaaagc cuuuggagug auaccacaga aaguauuuau |
| | | uuuuucugga acauuugaaa aaaacuugga ucccuaugaa caguggagug |
| | | aucaagaaau augga
aaguu gcagaugagg uugggcucag aucugugaua |
| | | gaacaguuuc cugggaagcu ugacuuuguc cuuguggaug ggggcugugu |
| | | ccuaagccau ggccacaagc aguugaugug cuuggcuaga ucguucuca |
| | | guaaggcgaa gaucuugcug cuugaugaac ccagcucua uuuggaucca |
| | | guaacauacc aaauaauuag aagaacucua aaacaagcau uugcugauug |
| | | cacaguaauu cucgugaac acaggauaga agcaaugcug gaaugccaac |
| | | aauuuuugu cauagaagag aacaaagugc ggcaguacga uuccauccag |
| | | aaacugcuga acgagaggag ccucuuccgg caagccauca gccccuccga |
| | | cagggugaag cucuuucccc accggaacuc aagcaagugc aagucuaagc |
| | | cccagauugc ugcucugaaa gaggagacag aagaaggu gcaagauaca |
| | | aggcuuuaga gagcagcaua aauguugaca ugggacauuu gcucauggaa |
| | | uuggagcucg ugggacaguc accucaugga auuggagcuc guggaacagu |
| | | uaccucugcc ucagaaaaca aggaugaauu aaguuuuuu uuaaaaaaga |
| | | aacauuuggu aaggggaauu gaggacacug auaugggucu ugauaaaugg |
| | | cuuccuggca auagucaaau ugugugaaag guacuucaaa uccuugaaga |
| | | uuuaccacuu guguuuugca agccagauuu uccugaaaac ccuugccaug |
| | | ugcuaguaau uggaaaggca gcucuaaaug ucaaucagcc uaguugauca |
| | | gcuuauuguc uagugaaacu cguuaauug uaguguugga gaagaacuga |
| | | aaucauacuu cuuagggguua ugauuaagua augauaacug gaaacuucag |
| | | cgguuuauau aagcuuguau uccuuuucu cuccucuccc caugauguuu |
| | | agaaacacaa cuauauuguu ugcuaagcau uccaacucau ucauuuccaa |
| | | gcaaguauua gaauaccaca ggaaccacaa gacugcacau caaaauaugc |
| | | cccauucaac aucuagugag cagucaggaa agagaacuuc cagauccugg |
| | | aaaucagggu uaguauuguc caggucuacc aaaaaucuca auauuucaga |
| | | uaaucacaau acaucccuua ccugggaaag ggcuguuaua aucuuucaca |
| | | ggggacagga ugguucccuu gaugaagaag uugauaugcc uuuucccaac |
| | | uccagaaagu gacaagcuca cagaccuuug aacuagaguu uagcuggaaa |
| | | aguauguuag ugcaaauugu cacaggacag cccuucuuuc cacagaagcu |
| | | ccagguagag ggguguaag uagauaggcc augggcacug ugggguagaca |
| | | cacaugaagu ccaagcauuu agauguauag guugauggug uauguuuuc |
| | | aggcuagaug uauguacuuc augcugucua cacuaagaga gaaugagaga |
| | | cacacugaag aagcaccaau caugaauuag uuuuauaugc uucuguuuua |
| | | uaauuuugug aagcaaaauu uuuucucuag gaaauauuua uuuuaauaau |
| | | guucaaaca uauauaacaa ugcuguauuu uaaagaaug auuaugaauu |
| | | acauuuguau aaaauaauuu uuauauuuga aauauugacu uuuuauggca |
| | | cuaguauuuc uaugaauauu uauguuaaa cugggacagg ggagaaccua |
| | | gggugauauu aaccaggggc caugaaucac cuuuuggucu ggagggaagc |
| | | cuuggggcug augcaguugu ugcccacagc uguaugauuc ccagccagca |
| | | cagccucuua gaugcaguuc ugaagaagau gguaccacca gucugacugu |
| | | uuccaucaag gguacacugc cuucucaacu ccaaacugac ucuuaagaag |
| | | acugcauuau auuuauuacu guaagaaaau aucacuuguc aauaaaauacc |
| | | auacauuugu gugaaa |

TABLE 2-continued

CFTR-related sequences (all in sense orientation).

| Name | SEQ ID NO: | Chr. 7 position |
|---|---|---|
| Target sequence for ASOs * (Bold-cryptic exon) | 37 | AAGCAGCATATTCTCAATACTATGTTTCATTAATAATTAAT AGAGATATATGAACACATAAAAGATTCAATTATAATCACC TTGTGGATCTAAATTTCAGTTGACTTGTCATCTTGATTTC TGGAGACCACAAGGTAATGAAAAATAATTACAAGAGTC TTCCATCTGTTGCAGTATTAAAATGGTGAGTAAGACACC CTGAAAGGAAATGTTCTATTCATGGTACAATGCAATTACAG CTAGCACCAAATTCAACACTGTTTAACTTTCAACATATTAT TTTG |
| Sequence motif no. 1 | 38 | GAUGGAAGA |
| Sequence motif no. 2 | 39 | CAACAGAUGGAAGA |

Corresponding to positions 17279930-117280013 in the genome according to the Assemble version used as updated in 2013 (UCSC Genome Browser on Human December 2013 (GRCh38/hg38)).

Materials and Methods

Fisher Rat Thyroid (FRT) Cellular System

In order to screen for antisense oligonucleotides (ASOs) that modulate the splicing of the 3849+10 kb C-to-T mutated CFTR a cellular screening system is required. As epithelial cells derived from patients (nasal or bronchial epithelial cells) are difficult to grow and have limited proliferation capacity the inventors have generated, fisher rat thyroid (FRT) cells stably expressing CFTR cDNA carrying the 3849+10 kb C-to-T mutation (FRT 3849 mut). The cDNA is transfected into FRT cells using the Flp-In system (Invitrogen) that allows integration at a specific genomic location. It is important to note that FRT Flp-In cells are widely used for analysis of CFTR and can be used for RNA as well as functional analyses. In order to study the effect of ASOs on splicing, the cDNA is cloned to include a mini gene containing intronic sequences around the exon of interest. As a positive control FRT cells containing the cDNA with the mini gene carrying the wild type (WT) sequence (C in the mutation site) were also generated (FRT 3849 WT).

Transfection

Each ASO was transfected into FRT 3849 mutant cells using Lipofectamine 2000 transfection reagent (Invitrogen) according to the lipofectamine 2000 reagent protocol using the following lipofectamine amounts: 96 well-0.15 µl, 6 well-3 µl, 10 mm plate-15 µl. In each experiment the effect of different ASOs was analyzed in comparison to cells treated with control ASOs.

RNA Extraction

Twenty-four (24) hours following transfection of FRT 3849 mutant cells, total RNA was extracted using RNeasy Mini Kit (QIAGEN). RNA concenctartion was determanied using nanodrop. RNA-less and reverse transcriptase-less reactions were used as controls. Complementary DNA (cDNA) synthesis was performed using the High Capacity cDNA Reverse Transcription kit (Applied Biosystems). The cDNA was analyzed by PCR and qPCR.

Quantitative Detection of Aberrantly Spliced CFTR Transcripts (qPCR)

Real-time PCR was performed in QuantStudio 12K Flex Real-Time PCR System using TaqMan® Fast Advanced Master Mix (Applied Biosystems) with TaqMan probes specific for the 84 bp cryptic exon. The expression level was normalized to the transcript levels of HPRT. Technical duplicates were analyzed for each sample. Analysis was perform using the double delta Ct analysis.

Determine the Ratio Between These Two Transcripts (PCR)

PCR was performed using the Platinum™ SuperFi™ Green PCR Master Mix 12359-10 (Invitrogen) on cDNA diluted 1:2.5,2 µl of diluted cDNA for each reaction. PCR products were then run on an agarose gel for detection of the correctly and aberrantly spliced transcripts. The gels were exposed to UV light to visualize the PCR products and images were produced. The quantification of the fraction of correctly spliced transcripts was quantified using image J.

Half Maximal Effective Concentration (EC50) Analysis

FRT cells were transfected with each lead ASO in six concentrations (0.1, 1, 2.5, 10, 50 and 100 nM). For concentrations lower than 100 nM, control ASO was added for completion to total concentration of 100 nM. In each experiment the effect of 3 different ASOs was analyzed in comparison to cells treated with 100 nM control ASOs.

CFTR Protein Analysis by Western Blot

For protein analysis FRT 3849 mutant cells were transfected with 10 nM lead ASOs or control ASO every 24 hr for 3 days. Twenty-four (24) hr following the last transfection protein was extracted using RIPA buffer and analyzed by immunoblotting with a CFTR antibody. 6% polyacrylamide gels were used for protein separation. The gel was transferred to a nitrocellulose membrane, and antibody hybridization and chemiluminescence were performed according to the standard procedures. The primary antibodies used in this analysis were mouse anti CFTR M3A7 (Millipore) and rabbit anti Calnexin (Sigma). HRP-conjugated anti-rabbit and anti-mouse secondary antibodies were obtained from Jackson ImmunoResearch Laboratories.

Studies of CFTR Function Using a Membrane Potential Assay

FRT 3849 mutant cells are grown in 96-well (black, flat bottom; corning) plates. 24 h following transfection of the different ASOs, CFTR channel function was analyzed using the FLIPR membrane potential assay as previously described. Briefly, the cells were loaded with blue membrane potential dye (Molecular Devices), which can detect changes in transmembrane potential. The plate was then read in a fluorescence plate reader (BioTek Synergy H1) for baseline levels followed by CFTR stimulation using the cAMP agonist forskolin (10 µM; Sigma), DMSO vehicle was used as a negative control. CFTR-mediated depolarization of the plasma membrane was detected as an increase in fluorescence and hyperpolarization (or repolarization) as a decrease. To terminate the functional assay, the CFTR inhibitor CFTRinh-172 (10 µM; Cystic Fibrosis Foundation Therapeutics) was added to each well. Changes in transmembrane potential were normalized to the values prior to activation.

Primary Nasal Epithelial Cell Sampling and Culture

Human nasal endothelial cells (HNE) cells were sampled by nasal brushing of both nostrils. To increase the number of filters available to test the corrector efficacy, the inventors used conditionally reprogrammed and re-differentiated HNE cells. HNE cells were then seeded on porous filters (0.33 $cm^2$, Transwell, Corning) and supplemented with culture medium. After 2 days, cells were cultured in an air-liquid interface for 2-4 weeks. ASOs dissolved in DDW, were added to the basal side of HNEs during the differentiation.

Ussing Chamber Studies

Following differentiation HNE cells were analyzed for CFTR channel using the Ussing chamber system as previously described (Pranke et al., 2017). In general, the short-circuit-current (Isc) was measured under voltage clamp conditions with an EVC4000 Precision V/I Clamp (World Precision Instruments). For all measurements, chloride concentration gradient across the epithelium was applied by differential composition of basal and apical Ringer solutions. Inhibitors and activators were added after stabilization of baseline Isc:sodium (Na+)-channel blocker Amiloride (100 µM) to inhibit apical epithelial Na+ channel (ENaC); cAMP agonists Forskolin (10 µM) to activate the transepithelial cAMP-dependent current (including Cl-transport through CFTR channels); VX-770 (10 µM) to potentiate CFTR activity; CFTR inhibitor CFTRinh172 (5 µM) to specifically inhibit CFTR; and ATP (100 UM) to challenge the purinergic calcium-dependent Cl-secretion. The change after Forskolin served as an index of CFTR.

Example 1

Novel Antisense Oligonucleotides (ASOs)

Figure 1:
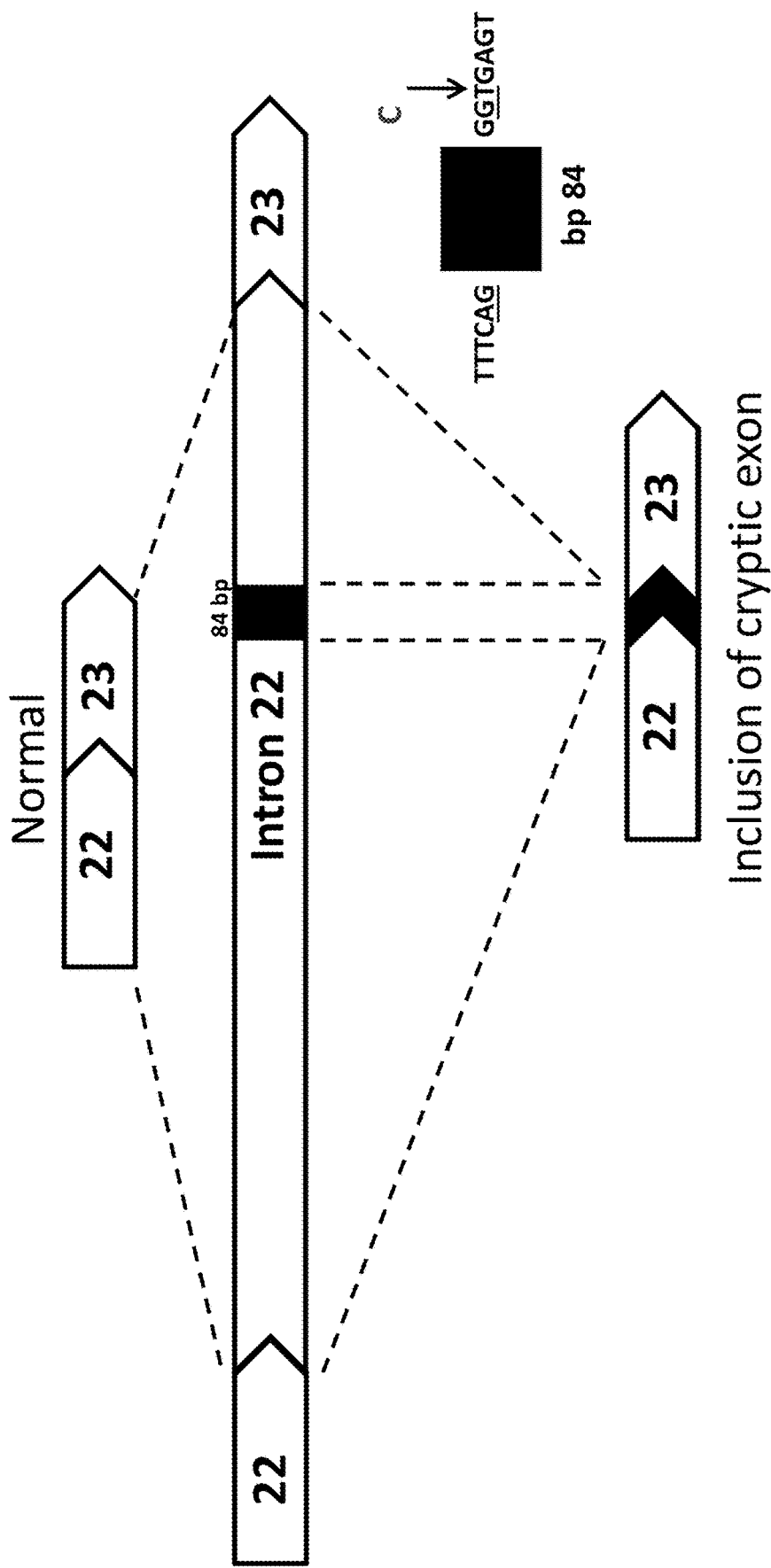
FIG. 1 is an illustration showing the effect of the 3849+10 kb C to T mutation in intron 22 of the CFTR gene. Top-upon normal splicing, exon 22 and exon 23 become adjacent. Bottom-a splicing mutation in intron 22 (denoted "3849+10 kb C-to-T" mutation) leads to inclusion of an excess of 84 bases in the mature CFTR mRNA (denoted "intron 22 cryptic exon"). The mutation creates a premature in-frame stop codon, leading to mRNA degradation by the nonsense mediated mRNA decay (NMD) mechanism.
Figure 2:
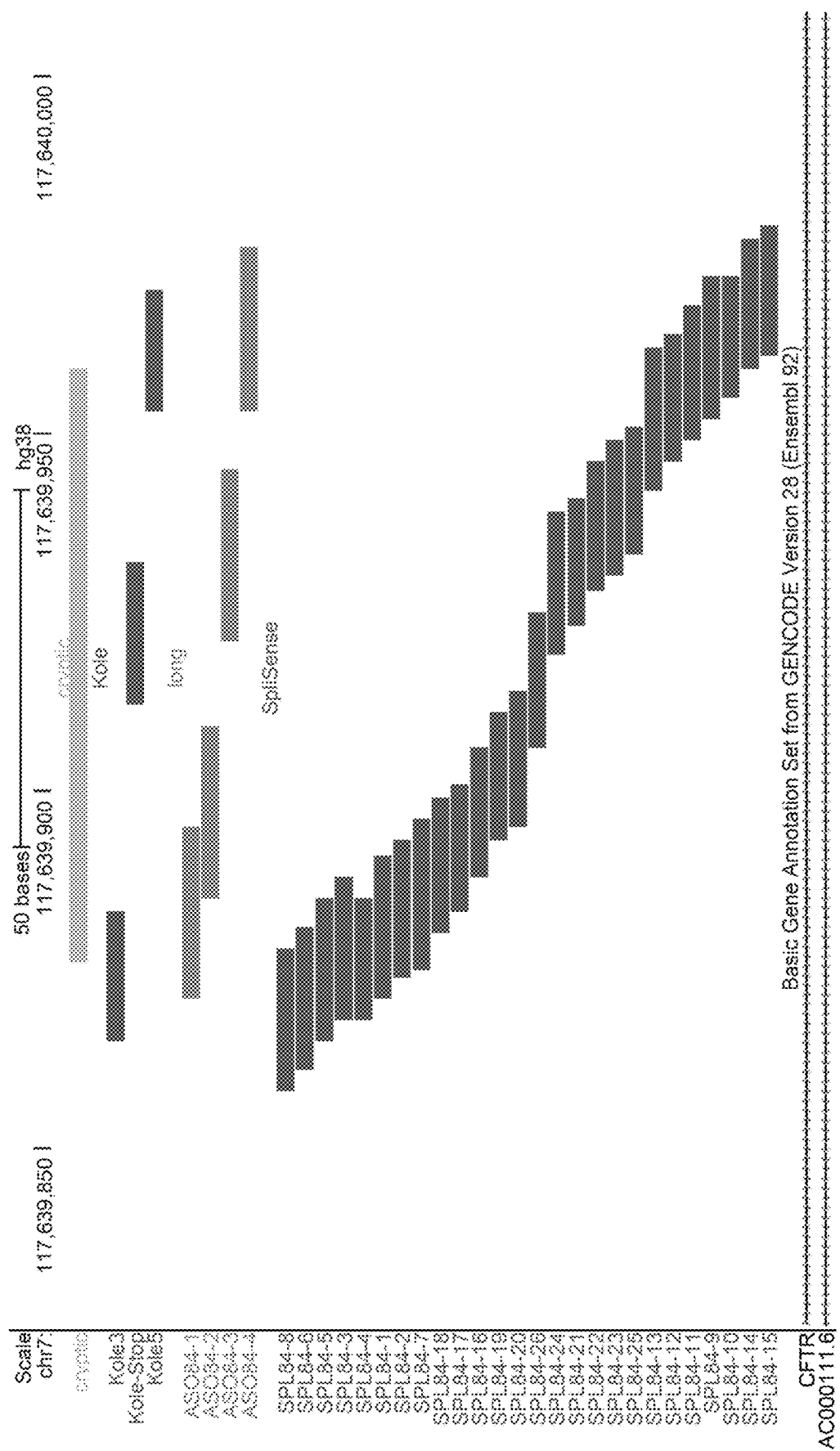
FIG. 2 is an illustration showing the binding sites (underlined) of oligonucleotides SPL84-1-SPL84-26 within the CFTR allele carrying the 3849+10 kb C to T mutation.
Figure 3A:
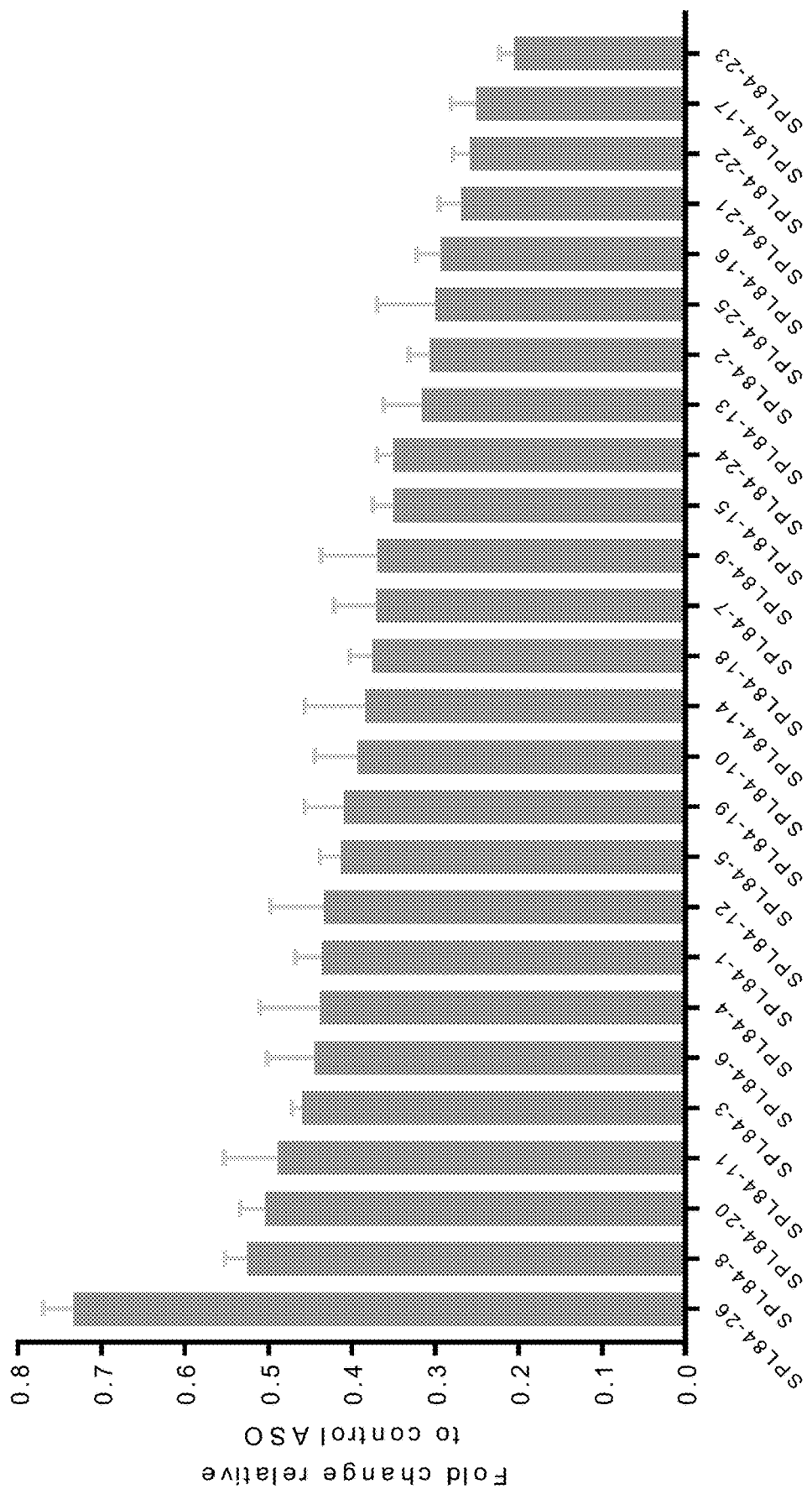
FIG. 3A is a vertical bar graph showing the change in levels of aberrantly spliced CFTR transcripts in FRT 3849 mut cells following antisense oligonucleotide (ASO) transfection (10 nM). Following a 24-hour treatment with the indicated ASO, RNA was extracted and the levels of aberrantly spliced CFTR transcripts were measured by qRT-PCR. The values shown are the average fold change (mean±s.e.m.) relative to cells treated with control ASO from 2-7 independent experiments. Values are normalized against transcripts of HPRT gene.
Figure 3B:
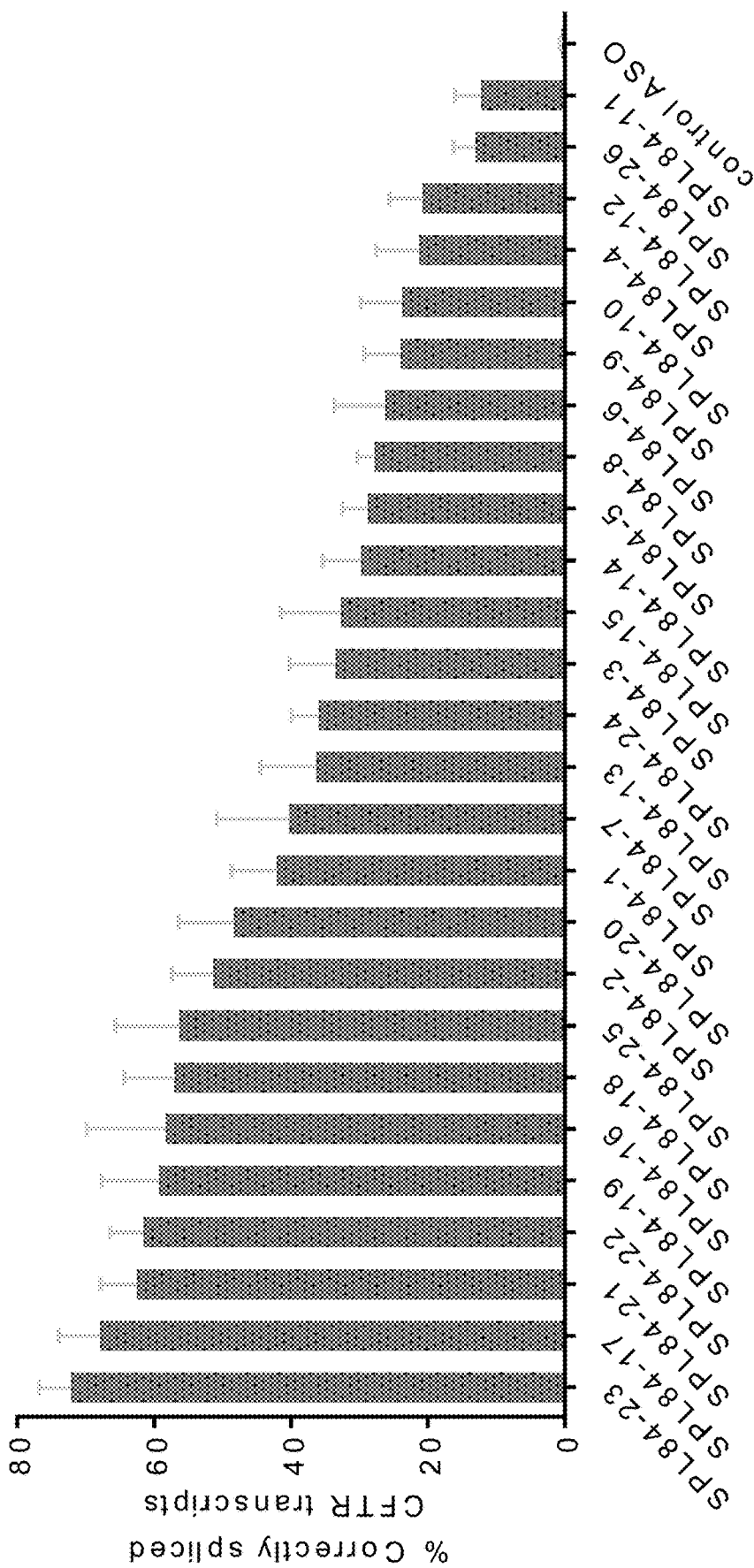
FIG. 3B is a vertical bar graph showing the percentage of correctly spliced CFTR transcripts in FRT 3849 mut cells following ASO transfection (10 nM). Following a 24-hour treatment with the indicated ASO, RNA was extracted and the ratio between the correctly and aberrantly spliced CFTR transcripts were measured by RT-PCR. The values shown are the average percentage of correctly spliced transcripts (mean±s.e.m.) from 3-8 independent experiments.

Twenty-six (26) new antisense oligonucleotides (ASOs) were analyzed for their effect on the splicing of CFTR pre-mRNA including the mutation 3849+10Kb C-to-T. The ASOs were modified with 2'-O-Methyl phosphorothioate (2'OMP). Briefly, Fischer rat thyroid (FRT) cells were transfected with the ASOs, incubated for 24 hours, and then RNA was extracted and the levels of aberrantly spliced CFTR transcripts were measured by qRT-PCR (FIG. 3A). In addition, the percentage of correctly spliced CFTR transcripts after incubation with each ASO was also determined (FIG. 3B). The values shown are the average fold change (mean±s.e.m.) relative to cells treated with a control ASO from 2-8 independent experiments. Values are normalized against transcripts of the HPRT gene.

As shown in FIG. 3, even at concentrations as low as 10 nM, all of the tested ASOs, except for one (SPL84-26) were surprisingly found to significantly decrease the levels of aberrantly spliced CFTR mRNA transcripts (to at least 0.6 of control ASO), and increase the prevalence of correctly spliced CFTR mRNA transcripts to at least 10 percent, compared to the negligible effect of the control ASO.

Example 2

Comparison of Novel ASOs and Previously Disclosed ASOs

The new ASOs provided herein were compared to several of the ASOs previously described (Friedman et al., J. Biol. Chem., 1999). The same methods were used as in Example 1 above, with the exception that in these experiments the FRT cells were transfected with lower concentrations of the ASOs (2.5 nM vs. 10 nM).

Figure 4A:
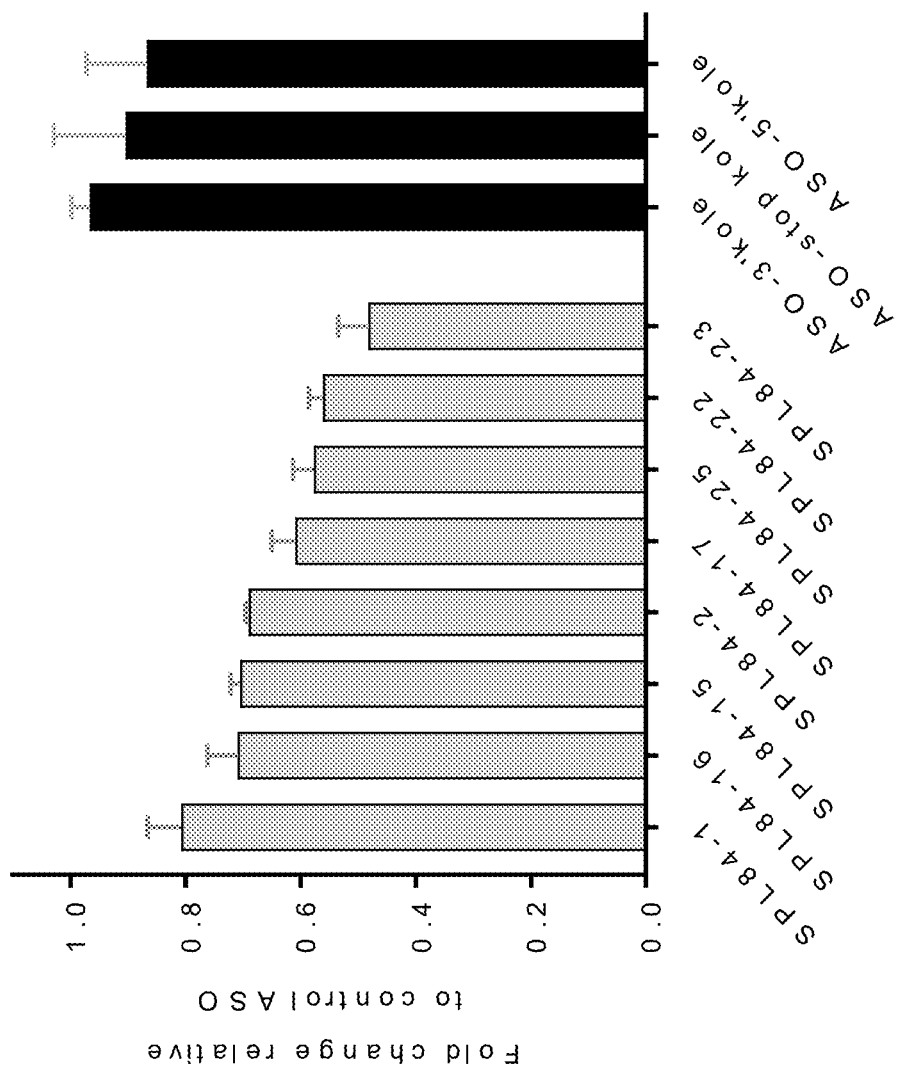
FIG. 4A is a vertical bar graph showing the change in levels of aberrantly spliced CFTR transcripts in FRT 3849 mut cells following ASO transfection (2.5 nM), compared to the ASOs described in Friedman et al., 1999. Following a 24-hour treatment with the indicated ASO, RNA was extracted and the levels of aberrantly spliced CFTR transcripts were measured by qRT-PCR. The values shown are the average fold change relative to cells treated with control ASO (mean±s.e.m.) from 3 independent experiments. Values were normalized against transcripts of HPRT gene.
Figure 4B:
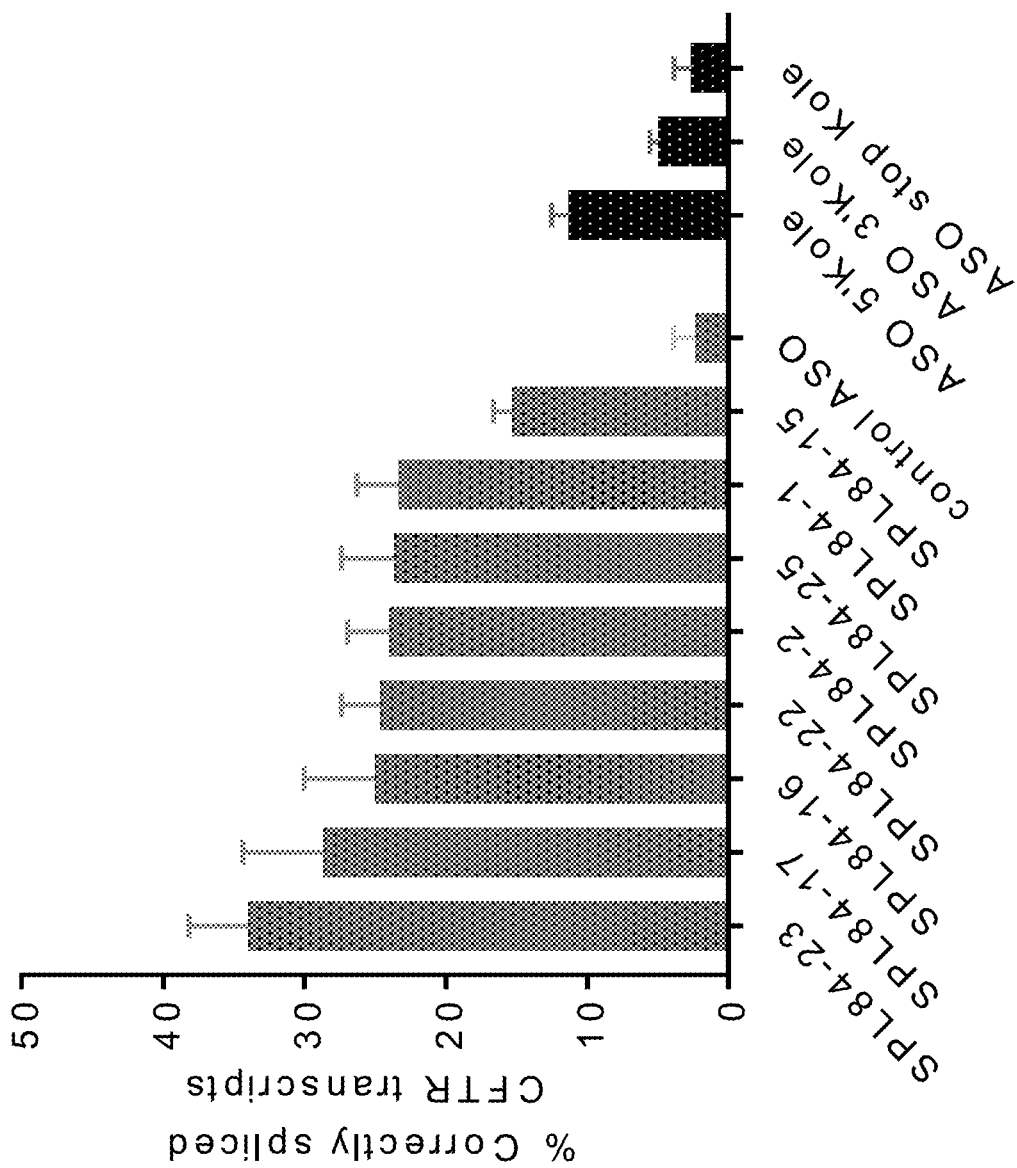
FIG. 4B is a vertical bar graph showing the percentage of correctly spliced CFTR transcripts in FRT 3849 mut cells following ASO transfection (2.5 nM), compared to the ASOs described in Friedman et al., 1999. Following a 24-hour treatment with the indicated ASO, RNA was extracted and the levels of correctly and aberrantly spliced CFTR transcripts were measured by RT-PCR. The values shown are the percentage of correctly spliced transcripts (mean±s.e.m.) from 3 independent experiments.

From the data presented in FIGS. 4A and 4B, it becomes evident that even at concentrations as low as 2.5 nM, all of the ASOs provided herein were surprisingly found to significantly decrease the levels of aberrantly spliced CFTR mRNA transcripts (to at least 80 percent of control ASO level), and increase the prevalence of correctly spliced CFTR mRNA transcripts to at least 15 percent, compared to the negligible effect of the control ASO. It is further important to note that these results are far superior to those achieved by previously described ASOs in a direct head-to-head comparison.

These results become even more surprising and promising when considering that the genetically-manipulated FRT cells used in the experiments contained a single copy of a CFTR gene having the 3849+10Kb C-to-T mutation, which is a condition more extreme than the most acute phenotype of CF in humans, where two CFTR gene alleles display little to none CFTR activity.

Example 3

Comparison of Novel ASOs and Previously Disclosed ASOs

The new ASOs provided herein were compared to several of the ASOs previously described in WO2014/045283. The same methods were used as in Example 1 above.

Figure 5A:
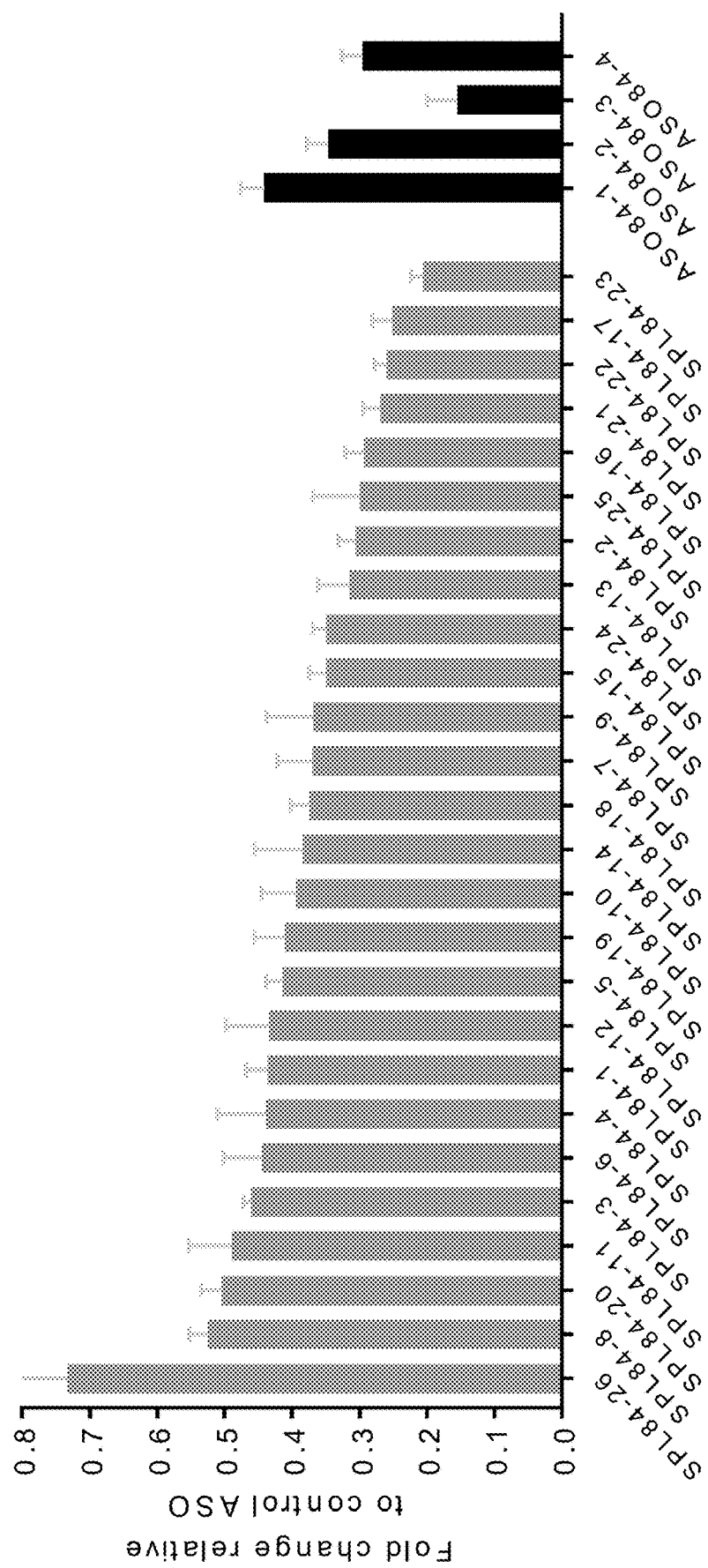
FIG. 5A is a vertical bar graph showing the change in levels of aberrantly spliced CFTR transcripts in FRT 3849 mut cells following ASO transfection (10 nM), compared to the ASOs described in WO 2014/045283. Following a 24-hour treatment with the indicated ASO, RNA was extracted and the levels of aberrantly spliced CFTR transcripts were measured by qRT-PCR. The values shown are the average fold change relative to cells treated with control ASO (mean±s.e.m.) from 3 independent experiments. Values were normalized against transcripts of HPRT gene.
Figure 5B:
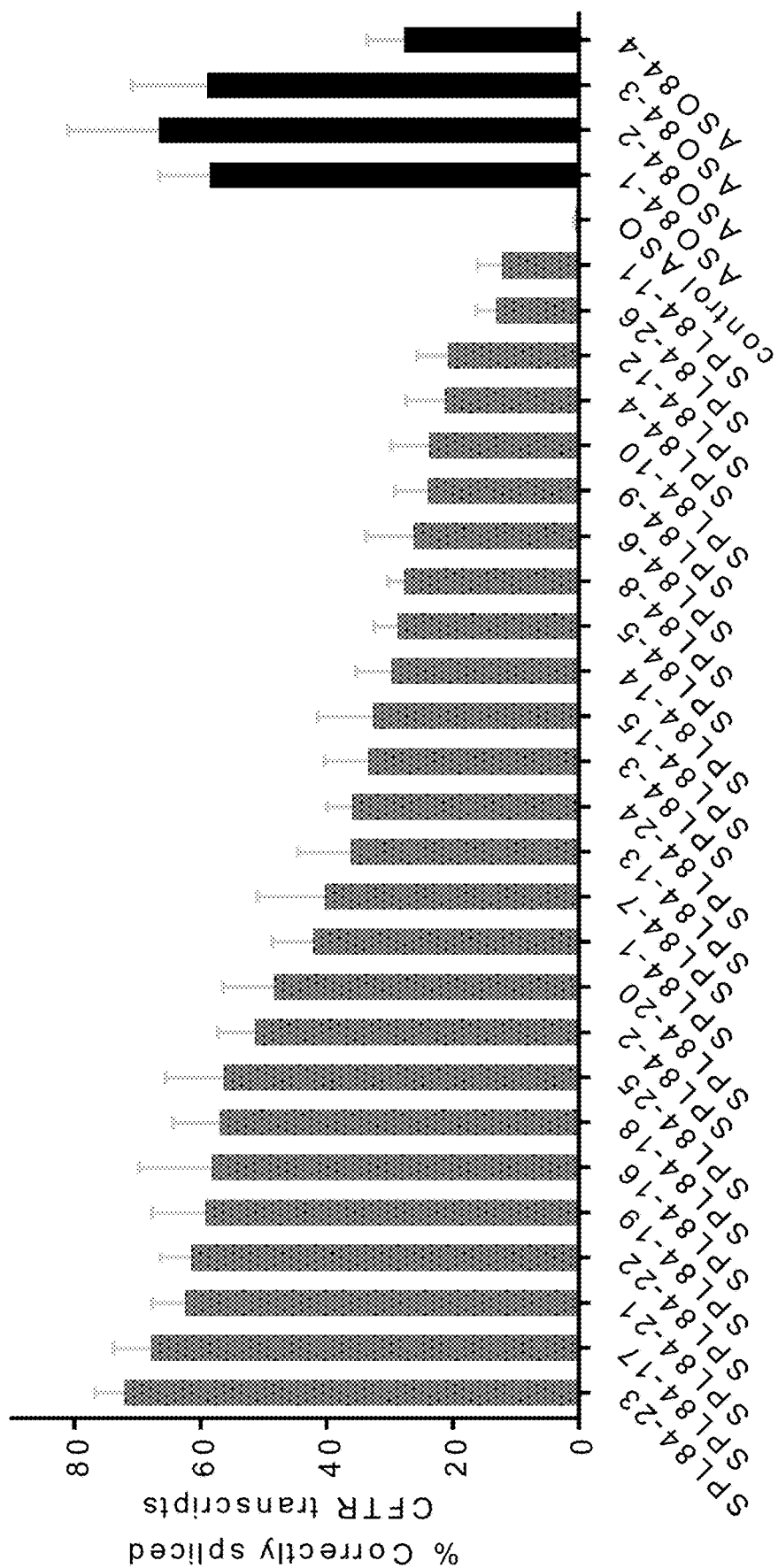
FIG. 5B is a vertical bar graph showing the percentage of correctly spliced CFTR transcripts in FRT 3849 mut cells following ASO transfection (10 nM), compared to the ASOs described in WO 2014/045283. Following a 24-hour treatment with the indicated ASO, RNA was extracted and the levels of correctly and aberrantly spliced CFTR transcripts were measured by RT-PCR. The values shown are the percentage of correctly spliced transcripts (mean±s.e.m.) from 3 independent experiments.

From the data presented in FIGS. 5A and 5B, it becomes evident that all of the ASOs provided herein were comparable in efficacy to the ASOs described in WO2014/045283, i.e. in decreasing the levels of aberrantly spliced CFTR mRNA transcripts, and/or increasing the prevalence of correctly spliced CFTR mRNA transcripts, compared to the negligible effect of the control ASO.

It is surprising to note that the new ASOs provided herein, despite being shorter than the ASOs previously described in WO2014/045283 (18-21 compared to 25 consecutive bases (16%-28%)), present comparable efficacies in any one of the experiments. It is especially surprising and unpredictable since the ASOs previously described in Friedman et al., 1999, having 18-19 consecutive bases, displayed inferior efficacy in all the experiments.

From the data presented in Examples 1, 2 and 3 above, it is readily apparent that the ASOs provided by the present invention are highly capable of manipulating the splicing of CFTR pre-mRNA transcripts containing the 3849+10Kb C-to-T mutation such that the ratio between correctly spliced CFTR mRNA transcripts and aberrantly spliced CFTR mRNA transcripts becomes much more favorable.

These results become even more surprising and promising when considering that the genetically-manipulated FRT cells used in the experiments contained a single copy of a CFTR gene having the 3849+10Kb C-to-T mutation, which is a condition more extreme than the most acute phenotype of CF in humans, where two CFTR gene alleles display little to none CFTR activity.

Example 4

EC50 Analysis of Novel ASOs

Figure 6:
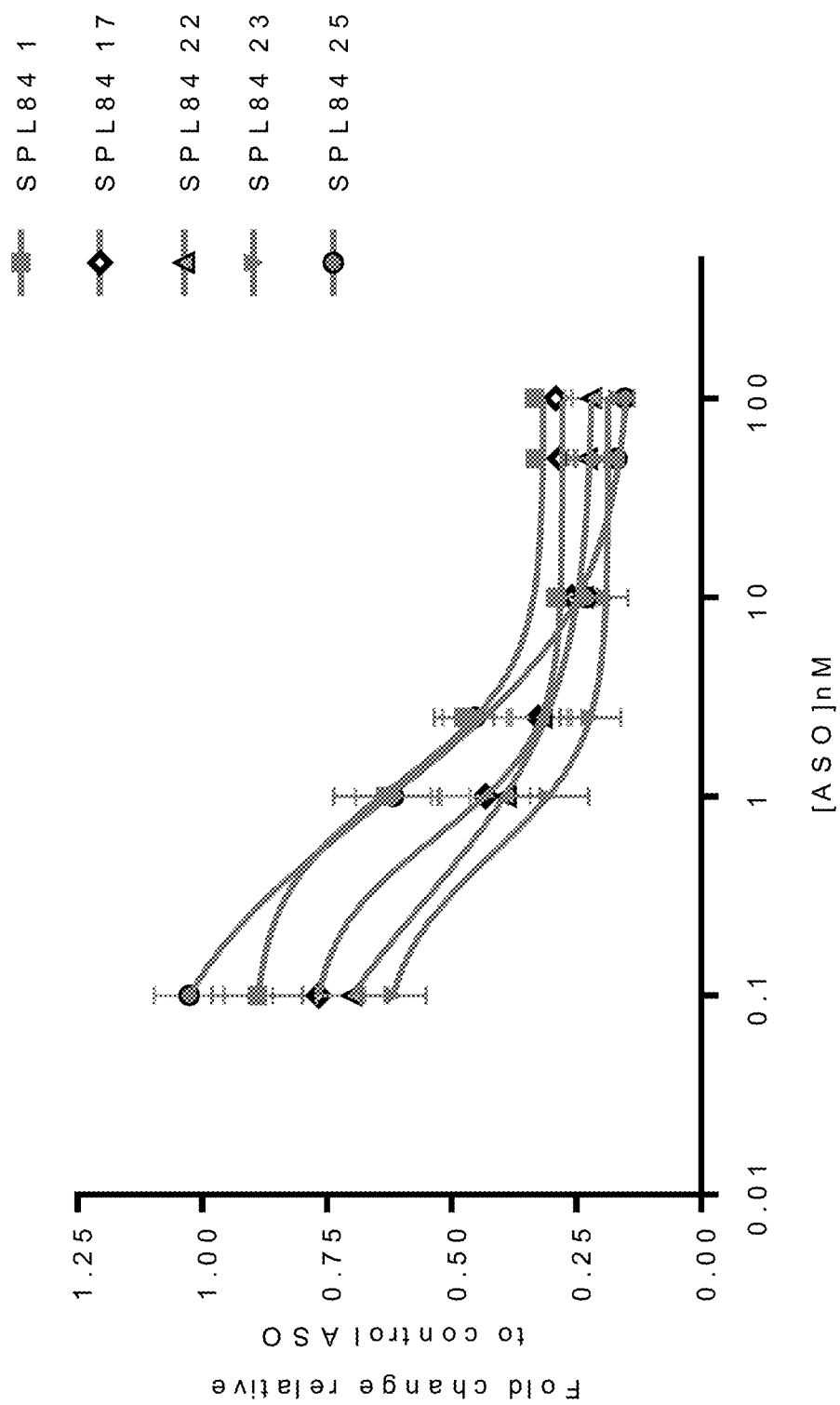
FIG. 6 is a graph showing the effect of different ASOs in different concentrations on the aberrantly spliced CFTR transcripts in FRT 3849 mut cells following a 24-hour treatment with the indicated ASO at the indicated concentration, RNA was extracted and the levels of aberrantly spliced CFTR transcripts were measured by qRT-PCR. The values shown are the average fold change relative to cells treated with control ASO (mean±s.e.m.). Values were normalized against transcripts of HPRT gene.

The new ASOs SPL84-2, SPL84-17, SPL84-22, SPL84-23 and SPL84-25 provided herein were tested in several concentrations to generate an EC50 curve indicating on the affinity and efficacy of each ASO. As illustrated in FIG. 6 and Table 3 (herein below), the ASOs were found to have a high efficiency and potency.

TABLE 3

|  | SPL84-1 | SPL84-17 | SPL84-22 | SPL84-23 | SPL84-25 |
|---|---|---|---|---|---|
| Maximal effect (Fold decrease from control ASO) | 0.316 | 0.2784 | 0.2157 | 0.1868 | 0.1339 |
| EC50 (nM) | 1.16 | 0.6246 | 0.3073 | 0.5133 | 0.9246 |

Example 5

Western Blot Analysis for CFTR Mature Protein Levels

The CFTR protein in a western blot can have two forms: immature-un-glycosylated protein (band B), and mature-full length glycosylated (band C). In homozygote WT cells most of the CFTR protein is found in band C-full length and mature. In FRT cells having the 3849+10Kb C-to-T mutation ("FRT mut") and treated with a control ASO all of the CFTR protein was visualized as truncated CFTR protein as in band B.

The transfection protocol was as follows: 10 nM of each ASO was transfected into FRT mut cells on three consecutive days. In each experiment the effect of several ASOs was analyzed in comparison to cells treated with 10 nM control ASOs. Each ASO was tested in 2 biological experiments. CFTR was stained by an antibody detecting only the full length CFTR protein (αCFTR-M3A7; FIG. 7). In the cells treated with control, no band C was detected, while following ASO transfection band C appeared, indicative of the formation of a full-length mature protein.

Figure 7A:
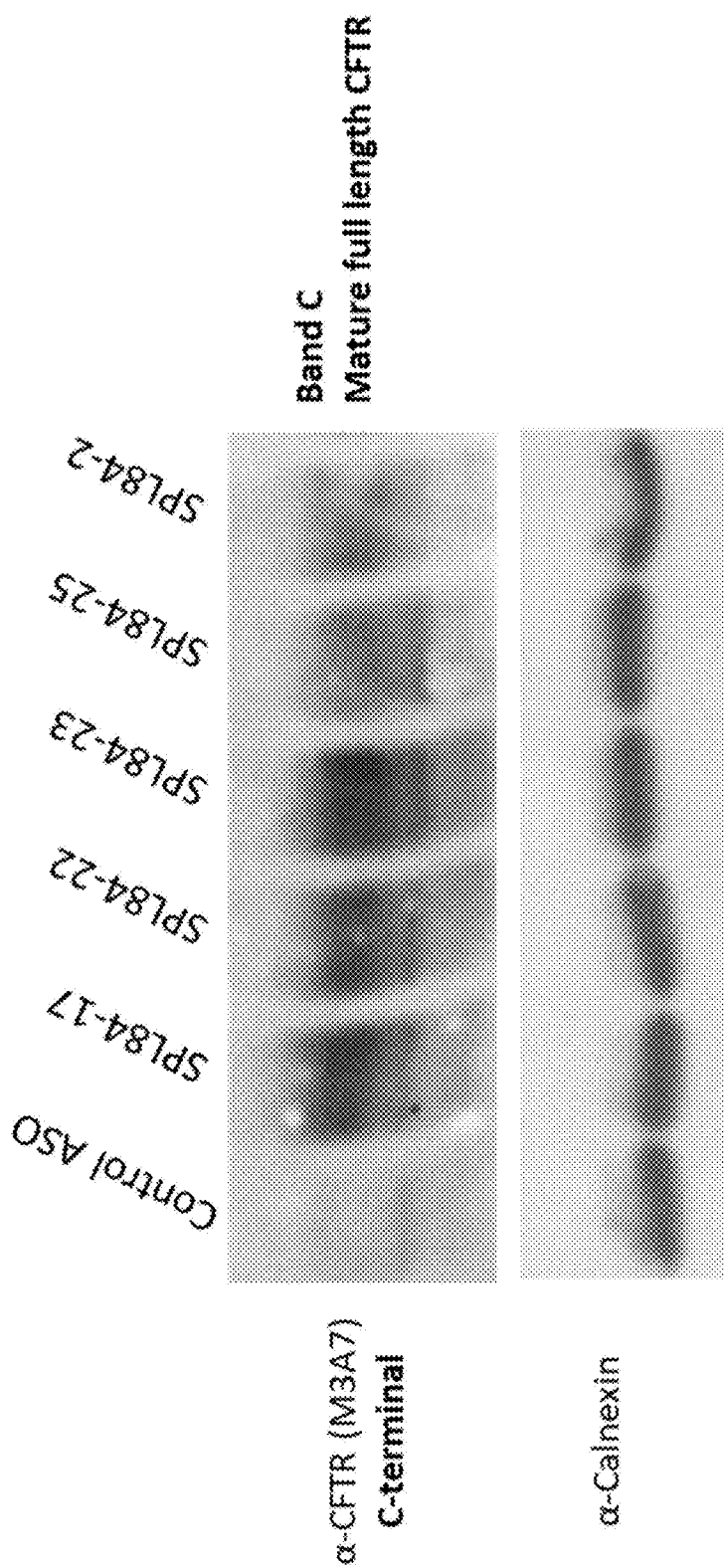
FIGS. 7A-7B are micrographs of western blot analyses showing the effect of different ASOs on the formation of full length mature CFTR protein. (7A) FRT 3849 mut cells were transfected with the indicated ASO. (7B) HEK 293T cells transiently expressing the CFTR cDNA mutated with the 3849+10Kb C-to-T mutation and containing the flanking intronic regions were transfected with the indicated ASO.
Figure 7B:
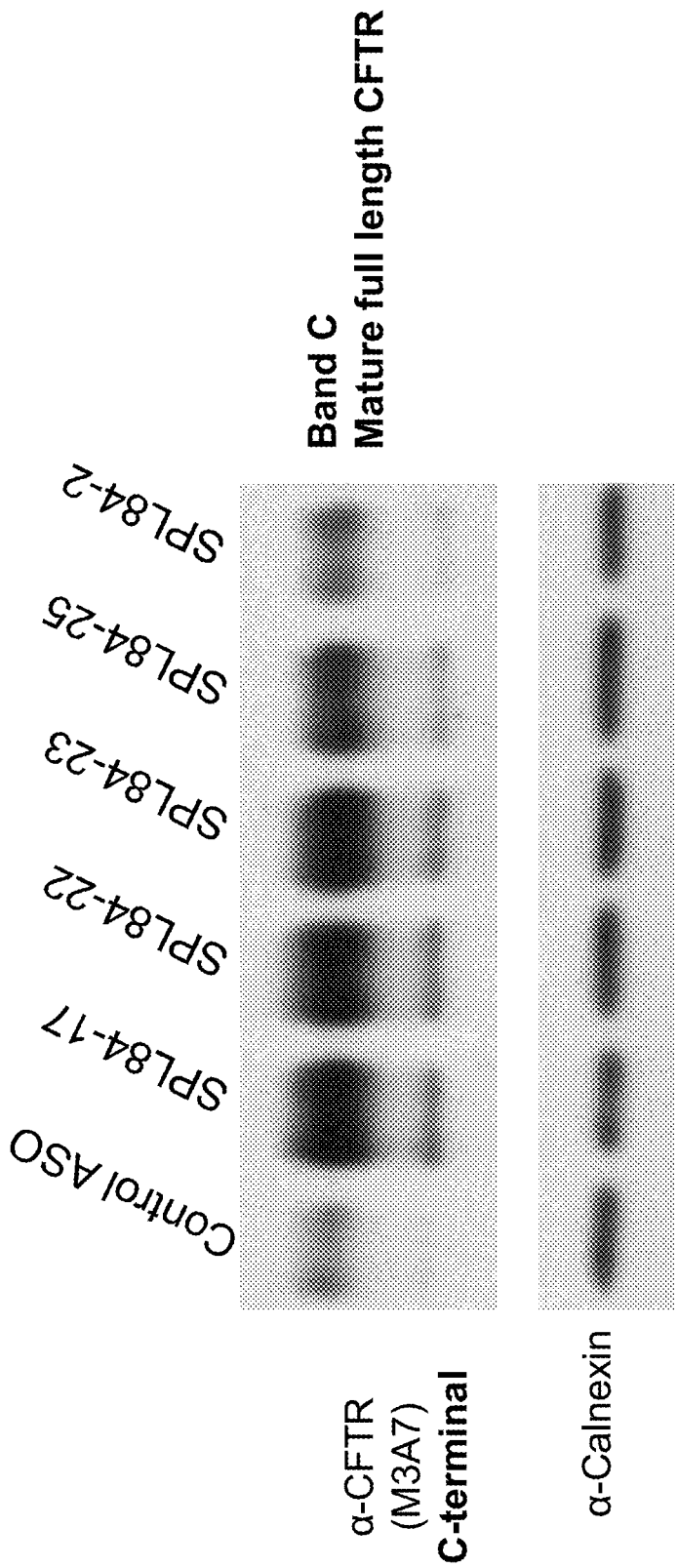

As illustrated in FIGS. 7A and 7B, the level of mature full-length protein was increased following transfection with 10 nM ASOs. These data provide direct evidence that the ASOs provided by the present invention have a pronounced and favorable effect not only on the pre-mRNA/mRNA level, but more importantly, on the protein level.

Example 6

Functional Analysis

FLIPR™ (Fluorescence Imaging Plate Reader) is a functional system for measuring changes in membrane potential by a fluorescent indicator. FLIPR can be used to test CFTR activation levels when the activation of CFTR is achieved by the addition of Forskolin (FSK) and the specificity for the CFTR channel is verified by the addition of CFTR specific inhibitor (inh-172). The experiments were performed 24 hours following transfection of 10 nM of each ASO to FRT mut cells.

FIG. 8A is a representative FLIPR trace demonstrating CFTR activation induced by ASO SPL84-17. FIG. 8B illustrates the average effect of several ASOs on CFTR function. (*, p value≤0.05; , p value≤0.01; *, p value≤0.001; ****, p value≤0.0001).

The data presented in FIGS. 8A and 8B clearly illustrates that the new ASOs provided by the present invention have a pronounced and favorable effect not only on the RNA and protein levels, but even more importantly, on the functional level.

Example 7

Efficacy in Primary Cells of a CF Patient

CFTR channel activity was analyzed in differentiated primary respiratory epithelial cells from CF patients. The Ussing chamber is employed to measure trans-epithelial currents indicative of the CFTR channel activity. This measurement is a strong predictor of patient response to the treatment ($R^2$=0.95).

Human Nasal Epithelial (HNE) cells from CF patients carrying at least one CFTR allele with the 3849+10Kb C-to-T mutation were provided. In order to increase the number of filter assays, conditionally reprogrammed and re-differentiated HNE cells were used. In these experiments the HNE cells were exposed to the ASOs for 15-23 days, while differentiating on filters, with no addition of a transfection reagent.

Ussing chamber experiments were performed on HNE cells from 5 CF patients. Four of them are heterozygous for the 3849 10+Kb C-to-T mutation and a minimal function mutation: Paris patient #2 and Israel patient #4 (3849+10 kb C-to-T/F508del), Israel patient #1 (3849+10 kb C-to-T/W1282X) and Israel patient #2 (3849+10Kb C-to-T/405+1G-to-A). In patients heterozygous for the 3849+10Kb C-to-T mutation, the maximum expected activity is 50% of WT, which is sufficient to confer full health conditions. An additional tested patient is homozygous for the 3849+10 kb C-to-T mutation (Paris patient #3).

First, 5 ASOs (SPL84-17, SPL84-22, SPL84-23, SPL84-2, and SPL84-25) were analyzed in cells from two patients (one heterozygote and one homozygote). In FIG. 9 the effects of the 5 ASOs in a compound heterozygote patient (Paris patient #2-3849+10 kb C-to-T/F508del), are presented. In order to measure CFTR activity levels in the most accurate way, the change after the addition of a specific CFTR inhibitor (inh-172) was used as an index. As can be seen in the representative traces (FIG. 9A) and in the median of CFTR inh-172 (FIG. 9B) all tested ASOs led to a significant activation of CFTR compared to the control ASO. In this patient, SPL84-23 had the strongest effect reaching 55% of WT when cells were exposed to SPL84-23. This level indicates a full restoration of the 3849 allele. The other 4 ASOs also led to a significant induction of the activity ranging from 34%-42.5% of WT.

The effect of each of the 5 ASOs was also analysed in HNEs from a patient homozygous for the 3849+10 kb C-to-T mutation (Paris #3). Consistent with the first tested heterozygote patient, ASO SPL84-23 showed full restoration of CFTR activity reaching activity levels of WT individuals. In this patient, three additional ASOs (SPL84-17, SPL84-22, and SPL84-2) also induced full restoration, indicating that these 3 ASOs also have a potential for high therapeutic efficacy. Nevertheless, the levels of CFTR activity between these ASOs varied, SPL84-17 and SPL84-22 showed higher levels of CFTR activity compared to SPL84-2 (231% and 186% compared to 151%, respectively). SPL84-25 also induced a high level of activation although lower than the effects of the other ASOs (93%) (FIG. 10).

Based on the results from the cells of these patients, the inventors chose to further analyse the effect of the 3 ASOs which showed the highest CFTR activity levels: SPL84-17, SPL84-22 and SPL84-23 (FIGS. 9 and 10).

Next, these 3 ASOs were tested in two additional heterozygote patients carrying different minimal function mutation on the second allele (W1282X and 405+1G-to-A). It is worth noting that the use of HNE cells enables access to patients with various genotypes, but still carrying one 3849+10 Kb C-to-T mutation. Consistent with the results from the first heterozygote patient (Paris #2), the 3 ASOs showed activation of CFTR in the additional tested patients, with a variable effect between patients.

The effect of ASO SPL84-23, which showed the highest effect in the tested heterozygotes, was tested in cells from an additional 3849+10 kb C-to-T/F508del patient (Israel #4). In this patient the exposure to the ASO led also to a significant activation of the CFTR channel to 38% of WT levels.

Summarizing the functional results from all heterozygote patients tested, SPL84-23 has the strongest effect across cells from patients with different genotypes, reaching full restoration of the CFTR activity (average of 42.5% of WT ranging from 23% to 73.5%). The other two ASOs, SPL84-17 and SPL84-22, also show a significant restoration of the 3849+10Kb C-to-T allele, with a more modest effect (average of 30% and 31% of WT, respectively) (FIG. 11).

Various data indicate that avoiding CF disease symptoms (e.g., lung function) requires only partial restoration of protein/RNA levels. As an indication, splice site variants that allow CFTR transcript levels to reach 10-25% of normal levels have been found in individuals that do not have CF lung disease. Thus, the results provide a solid indication for the potential of the ASOs as drug candidates with a significant clinical benefit.

Example 8

ASOs Effect on Splicing

To test whether the significant activation of CFTR by ASO SPL84-23 treatment results from reduction in the level of aberrantly spliced CFTR transcripts, the effect of ASO SPL84-23 on the splicing pattern was further analyzed by extracting RNA from the same filters used for the Ussing chamber measurements. As can be seen in FIG. 12A, the level of the aberrantly spliced CFTR transcripts, carrying the 84 bp cryptic exon, was significantly reduced in the HNE cells of both the heterozygotes and homozygote patients (as measured by qRT-PCR and calculating the relative fold change in CFTR aberrant transcript levels between control ASO and SPL84-23). In the homozygote cells, since all transcripts originate from the 3849+10 kb C-to-T mutated alleles, the absolute level of correctly and aberrantly spliced transcripts can be visualized on agarose gel using RT-PCR. The results demonstrate that SPL84-23 treatment resulted in a dramatic effect on the splicing pattern. In this patient, untreated cells or cells treated with the control ASO generated mainly aberrantly spliced CFTR with very low levels of correctly spliced transcripts. However, in SPL84-23 treated cells most of the RNA transcripts were correctly spliced (FIG. 12B).

Example 9

Chemical Modifications of AOs Effect CFTR Function in HNE Cells from a CF Patient The effect of an ASO with the same sequence and different chemical modifications was evaluated. 2'OMP is considered a second-generation ASO chemistry and the effect of another second-generation modification, 2'-Methoxy Ethyl (2'MOE), was tested. Both modifications have similar characteristics of: (1) slowing down degradation by protecting the ASOs from nucleases; and (2) having higher affinity to the target.

The effect of SPL84-23 having 2'OMPs or 2'MOE modification in primary human nasal epithelial cells from patients carrying the 3849+10 kb C to T mutation (free uptake) was compared using the Ussing chamber assay as described in Example 7.

CFTR function was measured in nasal epithelial cells from a patient homozygous for the 3849 mutation, following treatment of naked ASOs (free uptake, no transfection reagent) (FIG. 13). The ASOs were tested in 2 concentrations as indicated. SPL84-23 2'MOE showed a significant higher effect on the CFTR function compared to SPL84-23 2'OMP, in the two concentrations. Importantly, while SPL84-23 2'MOE completely rescued the CFTR function (to WT levels), in both 200 nM and 50 nM ASO concentrations, SPL84-23 2'OMP completely rescued the function only in the higher (200 nM) concentration.

Example 10

Optimization of ASO Improves Efficacy and Penetration

The inventors further optimized leading synthetic oligonucleotide candidates in order to improve their efficacy and penetration. The effects of chemistry and shortening of the ASO length were examined.

Changing the chemical modification from 2'OMe to IONIS 2nd generation 2'MOE and also ASO length from 17-20 bases were attempted.

Short versions of ASO84-23 were screened for their effect on splicing by free uptake on primary patient HNE cells (SPL84-23-1-SPL84-23-9). On average in the three 3849 heterozygote patients analyzed, the effect of SPL84-23-1 (19 mer) was comparable to SPL84-23 (FIG. 14).

Optimization of ASO length was further examined in primary HNE cells and in primary HBE cells (human bronchial epithelial cells) from a heterozygous a patient (3849/F508del).

SPL84-23-1 (19 mer) was shown to have a similar effect on the CFTR function as the longer SPL84-23 ASO in primary HNE cells (FIGS. 15A-15B), as well as in primary HBE cells (FIGS. 16A-16B).

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A synthetic oligonucleotide molecule complementary to a pre-mRNA transcript of a cystic fibrosis transmembrane conductance regulator (CFTR) gene having a 3849+10Kb C-to-T mutation, wherein the sequence of said synthetic oligonucleotide molecule consists of the sequence as set forth in SEQ ID NO: 1 or SEQ ID NO: 40 and characterized by increasing the percentage of correctly spliced mature CFTR mRNA by at least 10%; and decreasing the level of aberrantly spliced mature CFTR mRNA by at least 20%.

2. The synthetic oligonucleotide molecule of claim 1, comprising a chemical modification of the backbone of the oligonucleotide, a chemical modification of a sugar of the oligonucleotide, or a combination thereof.

3. The synthetic oligonucleotide molecule of claim 2, wherein the chemical modification comprises a phosphate-ribose backbone, a phosphate-deoxyribose backbone, a phosphorodiamidate morpholino backbone, a peptide nucleic acid backbone, an alternating locked nucleic acid backbone, a constrained ethyl (cET) backbone, a phosphorothioate backbone, an N3'-P5' phosphoroamidate, a 2'-deoxy-2'-fluoro-β-d-arabino nucleic acid, a cyclohexene nucleic acid backbone, a tricyclo-DNA (tcDNA) nucleic acid backbone, or a combination thereof.

4. The synthetic oligonucleotide molecule of claim 2, wherein the chemical modification comprises a 2'-O-methyl-phosphorothioate (2'OMP) modification or a 2'-Methoxy Ethyl (2'MOE) phosphorothioate modification.

5. A pharmaceutical composition comprising a synthetic oligonucleotide molecule complementary to a pre-mRNA transcript of a cystic fibrosis transmembrane conductance regulator (CFTR) gene having a 3849+10Kb C-to-T mutation and a pharmaceutically acceptable carrier, wherein the sequence of said synthetic oligonucleotide molecule consists of the sequence as set forth in SEQ ID NO: 1 or SEQ ID NO: 40 and characterized by increasing the percentage of correctly spliced mature CFTR mRNA by at least 10%; and decreasing the level of aberrantly spliced mature CFTR mRNA by at least 20%.

6. The pharmaceutical composition of claim 5, wherein said synthetic oligonucleotide comprises a chemical modification of the backbone of the oligonucleotide, a chemical modification of a sugar of the oligonucleotide, or a combination thereof.

7. The pharmaceutical composition of claim 6, wherein the chemical modification comprises a phosphate-ribose backbone, a phosphate-deoxyribose backbone, a phosphorodiamidate morpholino backbone, a peptide nucleic acid backbone, an alternating locked nucleic acid backbone, a constrained ethyl (CET) backbone, a phosphorothioate backbone, an N3'-P5' phosphoroamidate, a 2'-deoxy-2'-fluoro-β-d-arabino nucleic acid, a cyclohexene nucleic acid backbone, a tricyclo-DNA (tcDNA) nucleic acid backbone, a 2'-O-methyl-phosphorothioate (2'OMP) modification, a 2'-Methoxy Ethyl (2'MOE) phosphorothioate modification, or a combination thereof.

8. The pharmaceutical composition of claim 5, formulated for oral, nasal, inhalation, abdominal, subcutaneous, intraperitoneal or intravenous administration.

9. A method for treating Cystic Fibrosis in a subject in need thereof, comprising administering to said subject a therapeutically effective amount of a synthetic oligonucleotide complementary to a pre-mRNA transcript of a cystic fibrosis transmembrane conductance regulator (CFTR) gene having a 3849+10Kb C-to-T mutation, wherein the sequence of said synthetic oligonucleotide molecule consists of the sequence as set forth in SEQ ID NO: 1 or SEQ ID NO: 40, wherein said method is characterized by increasing the percentage of correctly spliced mature CFTR mRNA by at least 10%; and decreasing the level of aberrantly spliced mature CFTR mRNA by at least 20%.

10. The method of claim 9, wherein said synthetic oligonucleotide comprises a chemical modification of the backbone of the oligonucleotide, a chemical modification of a sugar of the oligonucleotide, or a combination thereof.

11. The method of claim 10, wherein the chemical modification comprises a phosphate-ribose backbone, a phosphate-deoxyribose backbone, a phosphorodiamidate morpholino backbone, a peptide nucleic acid backbone, an alternating locked nucleic acid backbone, a constrained ethyl (CET) backbone, a phosphorothioate backbone, an N3'-P5' phosphoroamidate, a 2'-deoxy-2'-fluoro-β-d-arabino nucleic acid, a cyclohexene nucleic acid backbone, a tricyclo-DNA (tcDNA) nucleic acid backbone, a 2'-O-methylphosphorothioate (2'OMP) modification, a 2'-Methoxy Ethyl (2'MOE) phosphorothioate modification, or a combination thereof.

12. The method of claim 9, wherein said synthetic oligonucleotide is administered orally, nasally, via inhalation, abdominally, subcutaneously, intra-peritoneally or intravenously.

13. The method of claim 9, wherein said subject is heterozygous for said 3849+10Kb C-to-T mutation.

* * * * *